US011360081B2

(12) United States Patent
Lee et al.

(10) Patent No.: US 11,360,081 B2
(45) Date of Patent: Jun. 14, 2022

(54) CELL-BASED METHOD FOR DETERMINING AN ACTIVITY OF BOTULINUM TOXIN

(71) Applicant: HUGEL, INC., Chuncheon-si (KR)

(72) Inventors: Chee Gun Lee, Yongin-si (KR); Ji Hyun Oum, Seongnam-si (KR); Vijayakumar Ajay, Seoul (KR); Xiangai Gui, Suwon-si (KR)

(73) Assignee: HUGEL INC., Seoul (KR)

( * ) Notice: Subject to any disclaimer, the term of this patent is extended or adjusted under 35 U.S.C. 154(b) by 0 days.

(21) Appl. No.: 17/029,892

(22) Filed: Sep. 23, 2020

(65) Prior Publication Data

US 2021/0063383 A1     Mar. 4, 2021

Related U.S. Application Data

(62) Division of application No. 16/245,415, filed on Jan. 11, 2019, now Pat. No. 10,823,725.

(30) Foreign Application Priority Data

Nov. 29, 2018 (KR) .......................... 10-2018-0150640
Nov. 29, 2018 (KR) .......................... 10-2018-0150997
Dec. 12, 2018 (KR) .......................... 10-2018-0159701

(51) Int. Cl.
*G01N 33/50* (2006.01)
*C07K 16/12* (2006.01)
*C12N 5/079* (2010.01)

(52) U.S. Cl.
CPC ..... *G01N 33/5058* (2013.01); *C07K 16/1282* (2013.01); *C12N 5/0618* (2013.01); *G01N 33/5014* (2013.01); *C07K 2317/565* (2013.01); *C12N 2500/32* (2013.01); *C12N 2500/36* (2013.01)

(58) Field of Classification Search
None
See application file for complete search history.

(56) References Cited

U.S. PATENT DOCUMENTS

| 8,198,034 B2 | 6/2012 | Fernandez-Salas et al. |
| 8,455,213 B2 | 6/2013 | Zhu et al. |
| 8,618,261 B2 | 12/2013 | Ester et al. |
| 8,658,363 B2 | 2/2014 | Yoshimura et al. |
| 2010/0203559 A1 | 8/2010 | Ester et al. |
| 2014/0248644 A1 | 9/2014 | Wang et al. |

FOREIGN PATENT DOCUMENTS

| EP | 3 330 372 A1 | 6/2018 |
| JP | 2007-526770 A | 9/2007 |
| JP | 4970057 B2 | 7/2012 |
| JP | 5284479 B2 | 9/2013 |
| KR | 10-2010-0139022 A | 12/2010 |
| KR | 10-1609894 B1 | 4/2016 |
| KR | 10-2017-0026624 A | 3/2017 |
| KR | 10-2017-0086699 A | 7/2017 |
| KR | 10-2017-0092583 A | 8/2017 |
| KR | 10-2018-0023871 | 7/2018 |
| KR | 10-2018-0023872 | 7/2018 |
| KR | 10-1898557 B1 | 9/2018 |
| KR | 10-1940500 | 1/2019 |
| KR | 10-1983216 | 5/2019 |
| WO | 2005/082096 A2 | 9/2005 |
| WO | 2010/105234 A1 | 9/2010 |
| WO | 2011/036812 A1 | 3/2011 |
| WO | 2014/207109 A1 | 12/2014 |
| WO | 2016/007508 A1 | 1/2016 |
| WO | 2016/097243 A1 | 6/2016 |

OTHER PUBLICATIONS

Jones et al., "Development of improved SNAP25 endopeptidase immuno-assays for botulinum type A and E toxins", Journal of Immunological Methods 329 (2008) 92-101.
Adler et al., "The Current Scientific and Legal Status of Alternative Methods to the LD50 Test for Botulinum Neurotoxin Potency Testing", ATLA, 2010, vol. 38, pp. 315-330 (total 16 pages).
Dong et al., "Using fluorescent sensors to detect botulinum neurotoxin activity in vitro and in living cells", PNAS, Oct. 12, 2014, vol. 101, No. 41, pp. 14701-14706 (total 6 pages).
Dunning et al., "Detection of Botulinum Neurotoxin Serotype A, B, and F Proteolytic Activity in Complex Matrices with Picomolar to Femtomolar Sensitivity", Applied and Environmental Microbiology, Nov. 2012, vol. 78, No. 21, pp. 7687-7697 (total 11 pages).
Fernández-Salas et al., "Botulinum Neurotoxin Serotype a Specific Cell-based Potency Assay to Replace the Mouse Bioassay", PLOS ONE, Nov. 2012, vol. 7, Issue 11, e49516, pp. 1-13 (total 13 pages).
Hong et al., "Development of a Highly Sensitive Cell-Based Assay for Detecting Botulinum Neurotoxin Type A through Neural Culture Media Optimization", Journal of Biomolecular Screening, Jan. 2016, 21(1), pp. 65-73 (total 16 pages).
Naumann et al., "Botulinum toxin type A in the treatment of focal, axillary and palmar hyperhidrosis and other hyperhidrotic conditions", European Journal of Neurology, 1999, vol. 6 (suppl 4), pp. S111-S115 (total 5 pages).
Wiegand et al., "125I-Labelled Botulinum A Neurotoxin: Pharrmacokinetics in Cats after Intramuscular Injection", Naunyn-Schmiedeberg's Archives of Pharmacology, 1976, vol. 292, pp. 161-165 (total 5 pages).
Habermann, "125I-Labeled Neurotoxin from Clostridium Botulinum A: Preparation, Binding to Synaptosomes and Ascent to the Spinal Cord", Naunyn-Schmiedeberg's Arch. Pharmacol., 1974, vol. 281, pp. 47-56 (total 10 pages).
Vajdos et al. (J Mol Biol. Jul. 5, 2002;320(2):415-28.
Brown et al. (J Immunol. May 1996; 156(9):3285-91.

(Continued)

*Primary Examiner* — Brian Gangle
(74) *Attorney, Agent, or Firm* — Sughrue Mion, PLLC

(57) ABSTRACT

A new cell line and an antibody for determining the activity of botulinum toxin are disclosed. Also disclosed is a method of determining the activity of botulinum toxin using the cell line and/or the antibody.

2 Claims, 34 Drawing Sheets

Specification includes a Sequence Listing.

(56) References Cited

OTHER PUBLICATIONS

Genbank: ATI97682.1, immunoglobulin heavy chain variable region, partial [Mus musculus], Oct. 16, 2017.
Genbank: AAT81540.1, immunoglobulin gamma 1 light chain variable region, partial [Mus musculus], Feb. 11, 2005.
Pellett, "Progress in Cell Based Assays for Botulinum Neurotoxin Detection", Curr Top Microbiol Immunol., May 6, 2013; 364: pp. 257-285. doi:10.1007/978-3-642-33570-9_12.

[Figure 1]
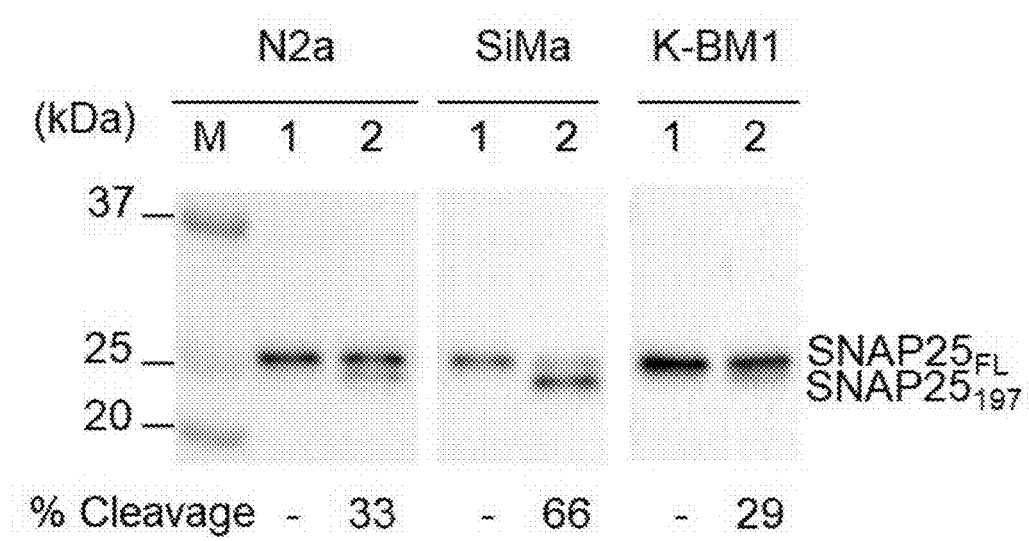

【Figure 2】

1st clonal selection of parental neuro-2a

SNAP25$_{FL}$
SNAP25$_{197}$
41  42  43

2nd clonal selection of clone 42 out of 6 positives

| SiMa | 2 | 17 | 22 | 23 | 25 | 27 | 29 | |
|---|---|---|---|---|---|---|---|---|
| − | + | + | + | + | + | + | + | + BoNT/A |
| 1 | 2 | 3 | 4 | 5 | 6 | 7 | 8 | 9 |

SNAP25$_{FL}$
SNAP25$_{197}$

SNAP25$_{197}$

3rd clonal selection of clone 2 out of 4 positives

| SiMa | | | 42F | | |
|---|---|---|---|---|---|
| − | + | + | + | + | − BoNT/A |
| 1 | 2 | 3 | 4 | 5 | 6 |

SNAP25$_{FL}$
SNAP25$_{197}$

[Figure 3]
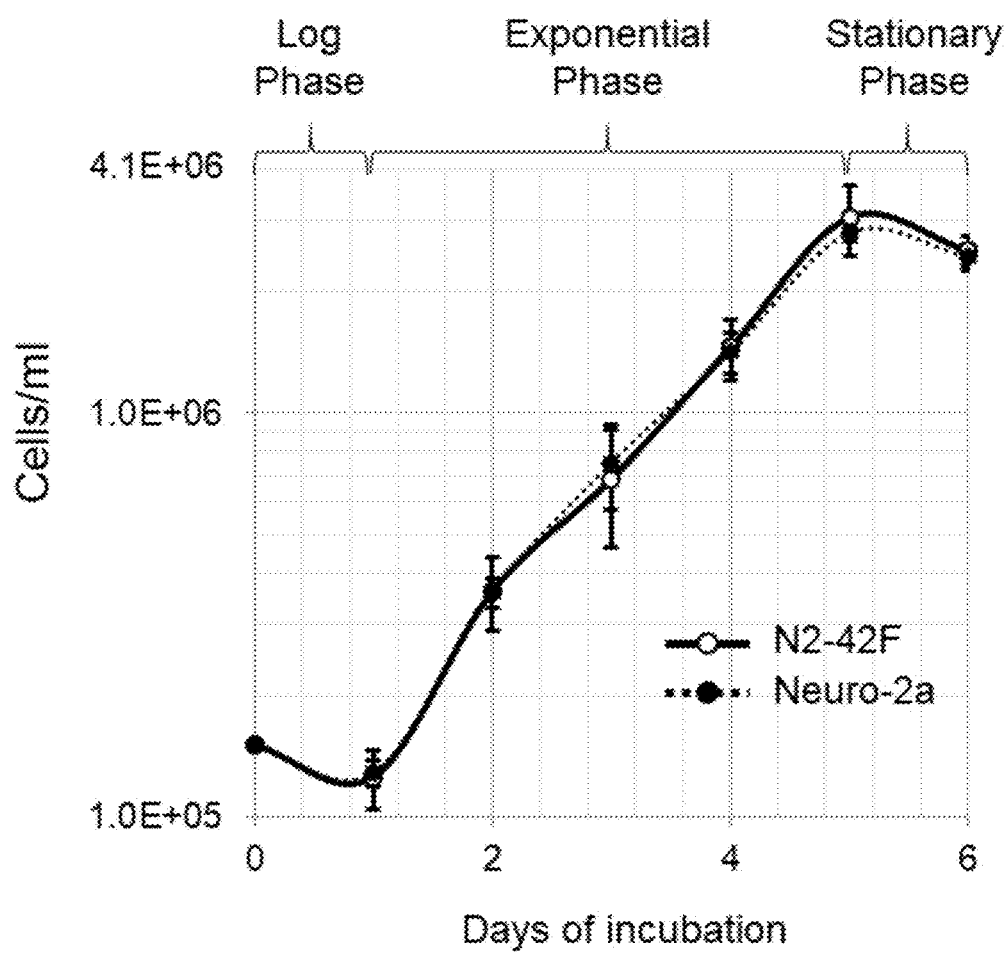

[Figure 4]
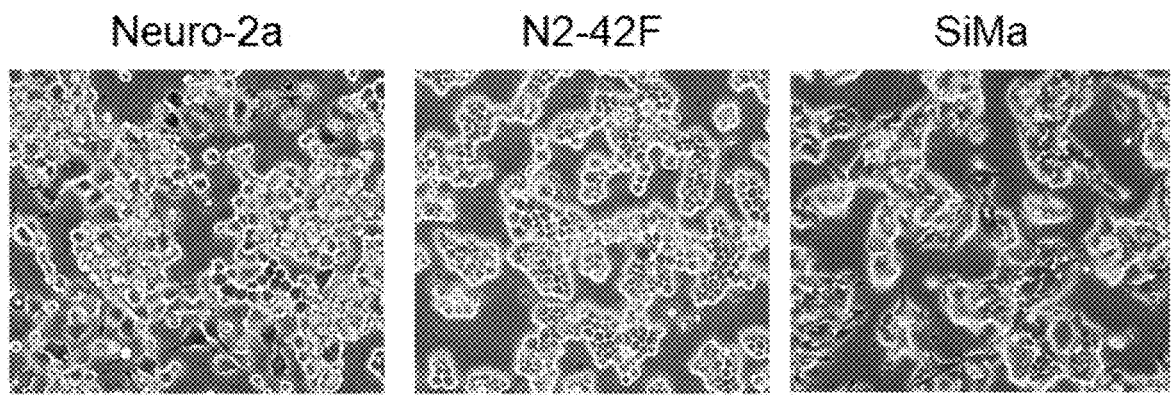

[Figure 5]
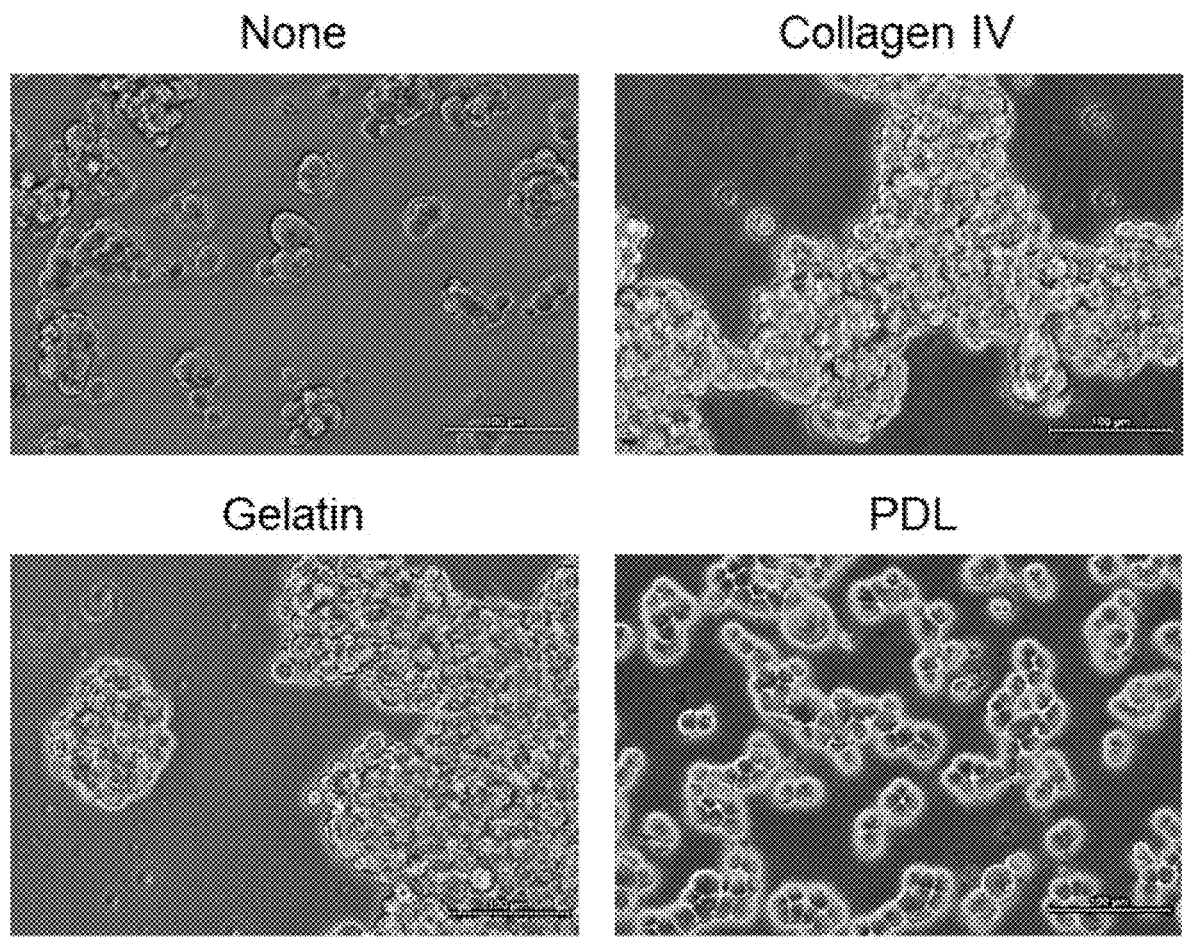

【Figure 6a】
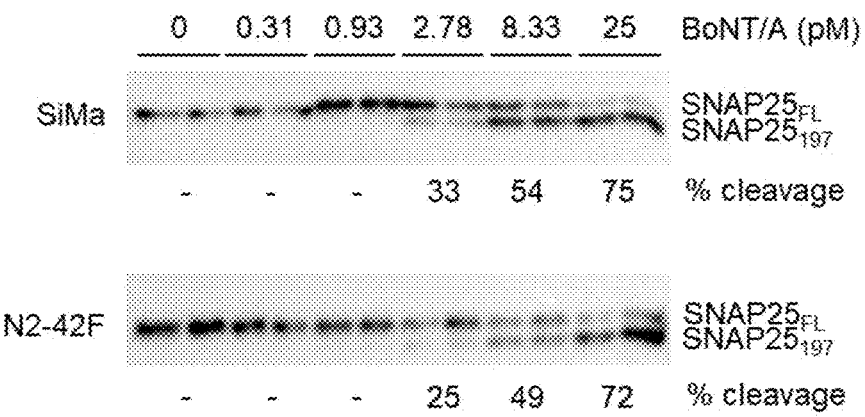
【Figure 6b】
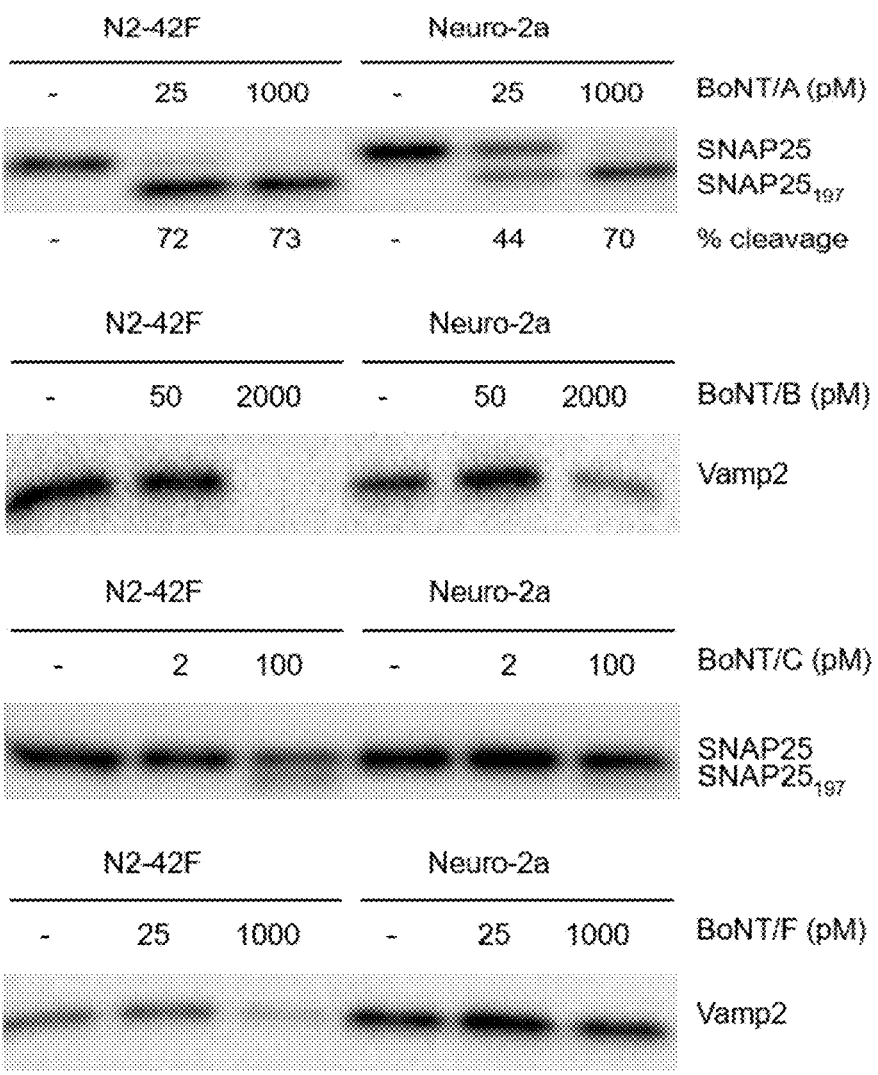

[Figure 7a]
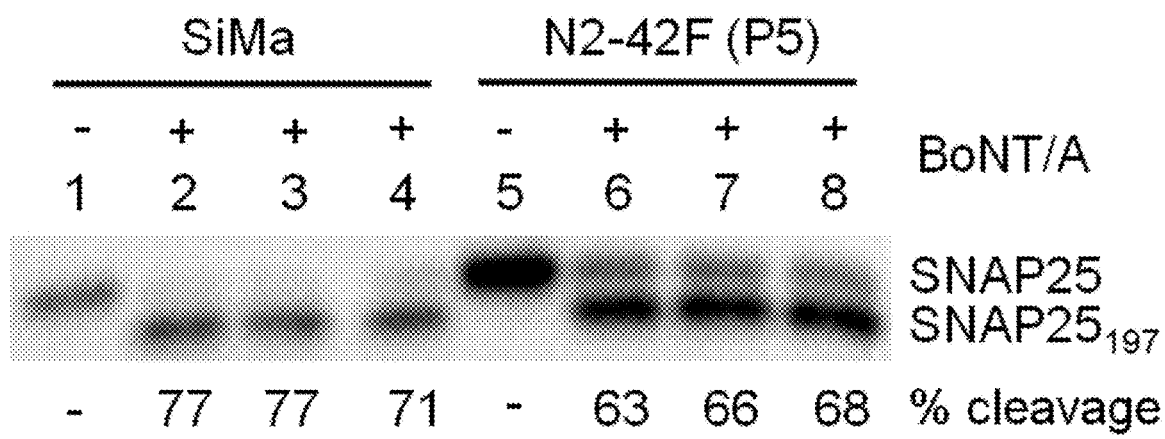
[Figure 7b]
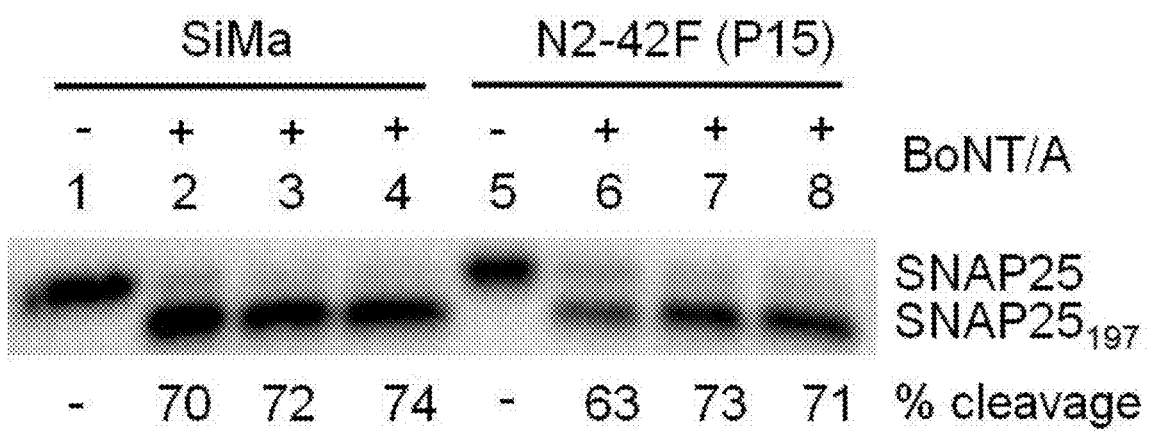

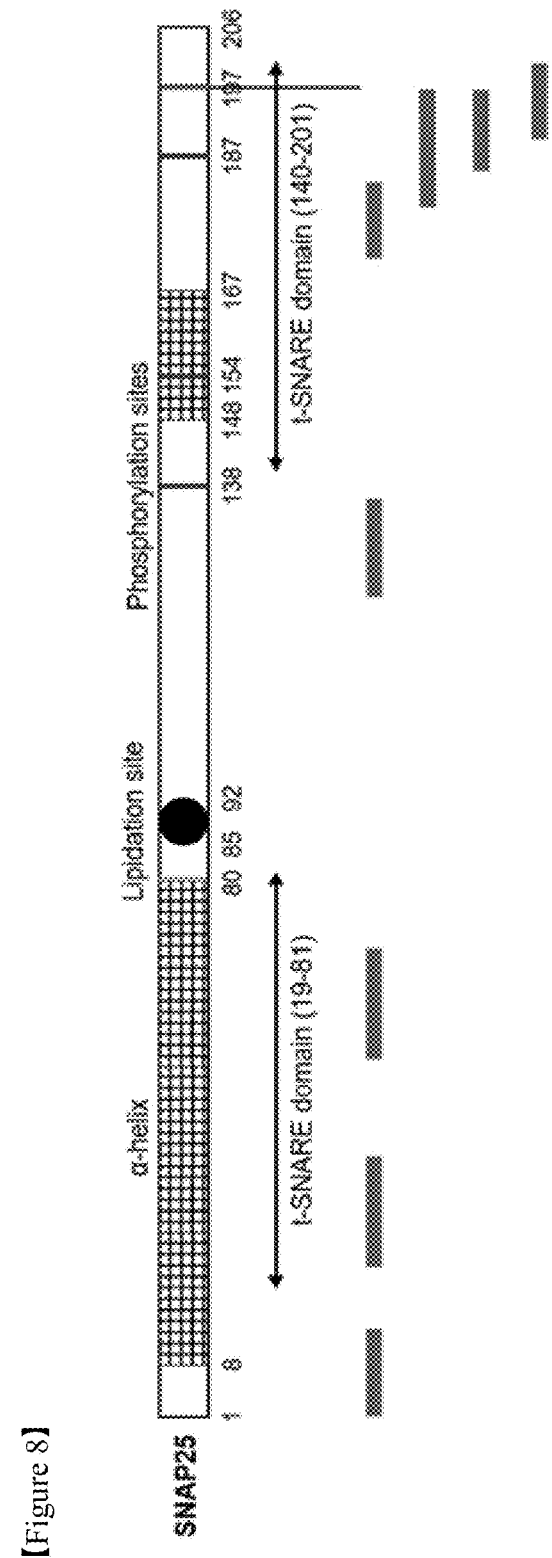
[Figure 8]

[Figure 9]
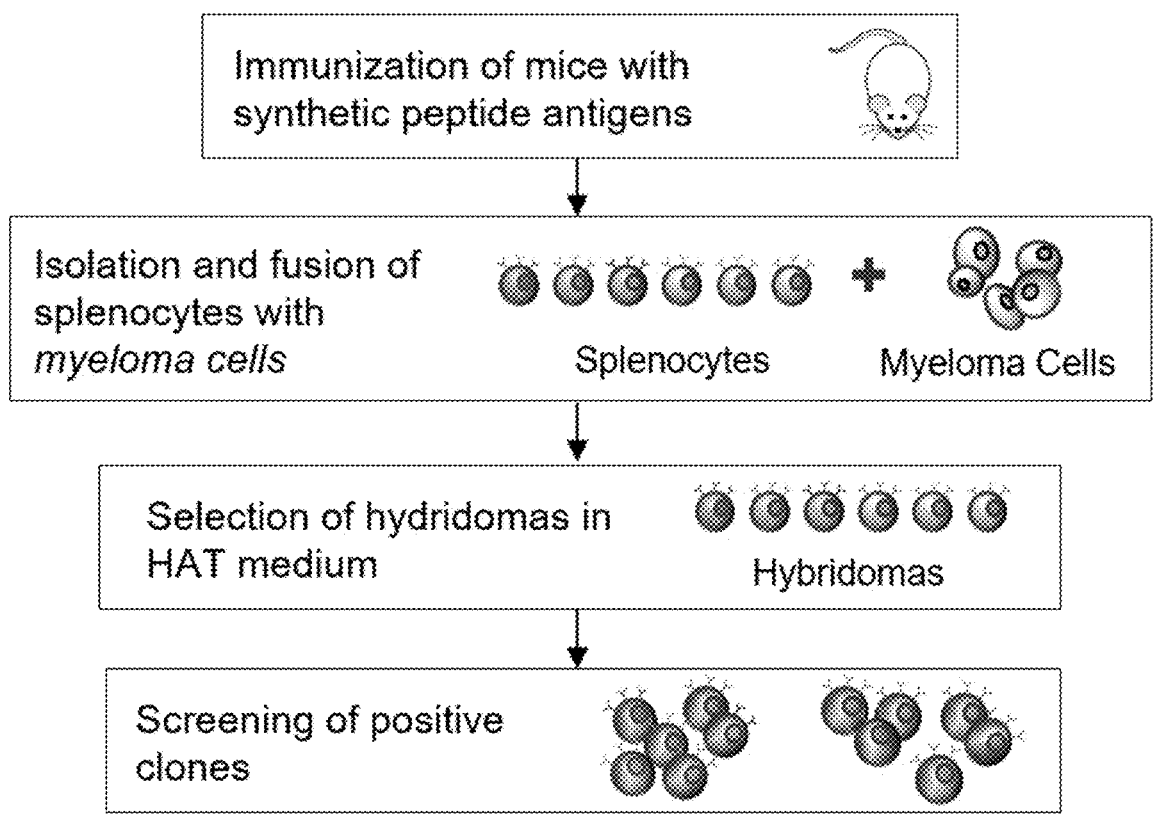

| | Fusion sup. test | | |
|---|---|---|---|
| A | 0.048 (1) | 0.065 (9) | 0.08 (17) |
| B | 0.050 (2) | 0.066 (10) | 0.069 (18) |
| C | 0.051 (3) | 0.072 (11) | 0.101 (19) |
| D | 0.100 (4) | 0.079 (12) | 0.125 (20) |
| E | 0.071 (5) | 0.08 (13) | 0.083 (21) |
| F | 0.248 (6) | 0.089 (14) | 0.084 (22) |
| G | 0.336 (7) | 0.075 (15) | 0.576 (23) |
| H | 0.139 (8) | 0.099 (16) | 0.107 (24) |

[Figure 11a]

| | 1 | 2 | 3 | 4 | 5 | 6 | 7 | 8 | 9 | 10 | 11 | 12 |
|---|---|---|---|---|---|---|---|---|---|---|---|---|
| A | 1.759 | 1.726 | 1.407 | 1.683 | 0.792 | 1.259 | 1.684 | 0.079 | 0.072 | 0.072 | 1.621 | 1.852 (1) |
| B | 1.642 | 1.663 | 1.713 | 1.498 | 1.629 | 1.738 | 1.652 | 1.572 | 1.739 | 1.759 | 0.062 | 0.081 |
| C | 1.507 | 1.679 | 1.413 | 1.417 | 1.636 | 1.645 | 1.694 | 1.491 | 1.718 | 0.056 | 1.693 | 0.081 |
| D | 1.718 | 1.772 | 1.645 | 0.063 | 1.709 | 1.788 | 1.740 | 0.056 | 0.063 | 0.256 | 0.064 | 0.099 |
| E | 1.728 | 1.755 | 1.849 | 1.667 | 0.066 | 1.877 (2) | 1.786 | 1.811 | 1.774 | 1.886 (3) | 0.063 | 1.632 |
| F | 1.877 (4) | 1.820 | 0.083 | 1.729 | 1.803 | 0.636 | 1.710 | 1.559 | 1.806 | 0.070 | 1.714 | 0.111 |
| G | 1.893 (5) | 1.820 | 1.732 | 1.727 | 1.735 | 1.796 | 0.065 | 1.707 | 1.779 | 0.096 | 0.111 | 0.080 |
| H | 1.843 | 1.838 | 0.743 | 1.679 | 1.845 | 0.343 | 1.728 | 0.085 | 1.685 | 0.096 | 0.099 | 1.709 |

[Figure 11b]
| Clones | 1 | 2 | 3 | 4 | 5 |
|---|---|---|---|---|---|
| #4 | 0.829 | 1.315 | 0.479 | 0.747 | 1.744 |
| #6 | 0.263 | 0.25 | 0.257 | 0.249 | 0.264 |
| #7 | 0.449 | 0.321 | 0.363 | 0.357 | 0.299 |
| #8 | 0.25 | 0.344 | 0.276 | 0.226 | 0.233 |
| #16 | 0.395 | 0.536 | 0.299 | 0.361 | 0.455 |
| #17 | 0.718 | 0.3 | 1.052 | 0.398 | 0.252 |
| #19 | 1.464 | 0.275 | 1.973 | 0.256 | 1.942 |
| #20 | 0.611 | 2.677 | 3.475 | 0.366 | 2.646 |
| #23 | 3.543 | 3.573 | 3.422 | 3.32 | 3.476 |
| #24 | 2.852 | 0.214 | 0.229 | 0.236 | 0.222 |
| Cont | 2.501 | 0.213 | 0.053 | 0.05 | 0.046 |
PC　　　NC
[Figure 11c]
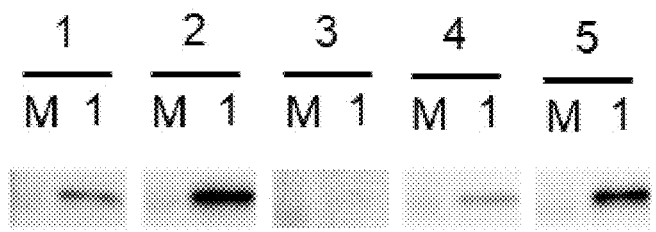

[Figure 12a]
| #4 | 1 | 2 | 3 | 4 | 5 | 6 | 7 | 8 | 9 | 10 | 11 | 12 |
|---|---|---|---|---|---|---|---|---|---|---|---|---|
| A |  | 0.060 | 1.517 | 1.685 | 0.066 | 1.617 | 1.684 |  | 0.050 |  | 0.050 | 0.058 |
| B | 1.612 | 1.495 | 0.048 | 1.683 | 0.051 | 0.388 | 1.618 | 1.617 | 0.048 | 0.049 | 0.048 | 0.060 |
| C | 1.529 | 1.489 | 0.050 | 1.491 | 1.517 | 1.533 | 1.567 | 0.061 | 0.051 | 0.051 | 0.048 | 0.056 |
| D | 0.193 | 1.435 | 1.442 | 1.645 | 0.047 | 1.571 | 1.415 | 1.621 | 1.534 | 1.571 | 0.048 | 0.054 |
| E | 0.066 | 1.419 | 1.531 | 1.612 | 0.047 | 1.695 | 0.051 | 1.596 | 0.052 | 0.052 | 0.053 | 1.542 |
| F | 1.497 | 1.501 | 1.501 |  | 1.642 | 1.656 | 0.052 | 0.053 | 0.051 | 0.052 | 0.053 | 0.170 |
| G |  | 1.452 | 0.052 | 0.192 | 1.603 | 0.054 | 1.654 | 1.686 | 0.052 | 1.627 | 1.665 | 0.065 |
| H | 1.724 | 1.619 | 1.596 | 1.685 | 1.630 | 0.070 | 1.628 | 0.056 | 0.056 | 1.532 | 0.383 | 1.995 |
[Figure 12b]
| Clones | 1 | 2 | 3 | 4 | 5 |
|---|---|---|---|---|---|
| #4 | 2.41 | 3.414 | 2.974 | 1.795 | 2.786 |
| #7 | 1.192 | 0.899 | 0.328 | 0.043 | 0.084 |
| #16 | 0.807 | 2.48 | 2.049 | 0.478 | 0.149 |
| #17 | 0.491 | 1.246 | 0.45 | 1.297 | 0.47 |
| #19 | 2.203 | 1.17 | 0.194 | 0.042 | 0.042 |
| #20 | 3.555 | 3.399 | 2.266 | 2.832 | 0.939 |
| #23 | 2.851 | 3.628 | 3.591 | 3.381 | 1.383 |
| #24 | 1.326 | 2.793 | 2.084 | 1.412 | 0.553 |
| Cont | 3.468 | 0.125 | 0.041 | 0.041 | 0.041 |
PC　　NC
[Figure 12c]
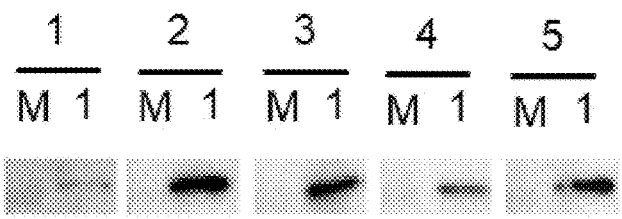

[Figure 13a]
|   | 1 | 2 | 3 | 4 | 5 | 6 | 7 | 8 | 9 | 10 | 11 | 12 |
|---|---|---|---|---|---|---|---|---|---|---|---|---|
| A | 1.577 | 1.765 | 1.9521 (1) | 1.816 | 1.812 | 1.206 | 1.822 | 1.762 | 1.226 | 0.072 | 1.732 | 1.9889 (2) |
| B | 1.617 | 1.519 | 1.692 | 1.509 | 1.770 | 1.701 | 1.585 | 1.585 | 1.9238 (3) | 1.930 | 0.055 | 1.8895 (4) |
| C | 0.865 | 1.068 | 0.965 | 0.955 | 0.924 | 0.841 | 1.009 | 0.051 | 1.043 | 1.154 | 1.045 | 1.139 |
| D | 1.620 | 1.653 | 1.744 | 1.500 | 1.527 | 1.754 | 1.616 | 1.348 | 1.713 | 0.051 | 1.557 | 0.071 |
| E | 1.291 | 1.617 | 1.643 | 1.622 | 1.508 | 1.511 | 1.789 | 1.612 | 1.614 | 1.722 | 1.676 | 1.740 |
| F | 1.686 | 0.054 | 1.725 | 1.844 | 1.640 | 1.479 | 1.847 | 1.380 | 1.524 | 0.052 | 1.256 | 0.063 |
| G | 1.820 | 1.749 | 1.626 | 1.691 | 0.052 | 1.682 | 1.652 | 1.572 | 0.105 | 0.207 | 1.571 | 0.058 |
| H | 1.6811 (5) | 1.802 | 1.806 | 1.794 | 1.758 | 1.704 | 1.713 | 1.627 | 1.828 | 0.052 | 0.053 | 1.846 |
[Figure 13b]
| Clones | 1 | 2 | 3 | 4 | 5 |
|---|---|---|---|---|---|
| #4 | 3.569 | 2.056 | 3.08 | 1.036 | 2.45 |
| #16 | 2.076 | 1.97 | 1.718 | 1.627 | 1.985 |
| #17 | 0.654 | 0.437 | 1.348 | 1.185 | 0.98 |
| #19 | 1.657 | 1.882 | 1.784 | 2.305 | 1.897 |
| #20 | 2.285 | 2.353 | 2.626 | 2.735 | 2.732 |
| #23 | 3.148 | 3.1 | 3.321 | 3.503 | 3.055 |
| Cont | 2.77 | 0.27 | 0.042 | 0.042 | 0.042 |
|  | PC | NC |  |  |  |
[Figure 13c]
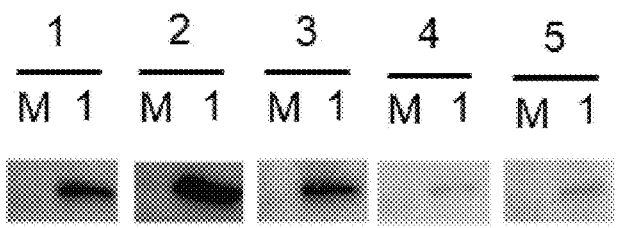

[Figure 14a]
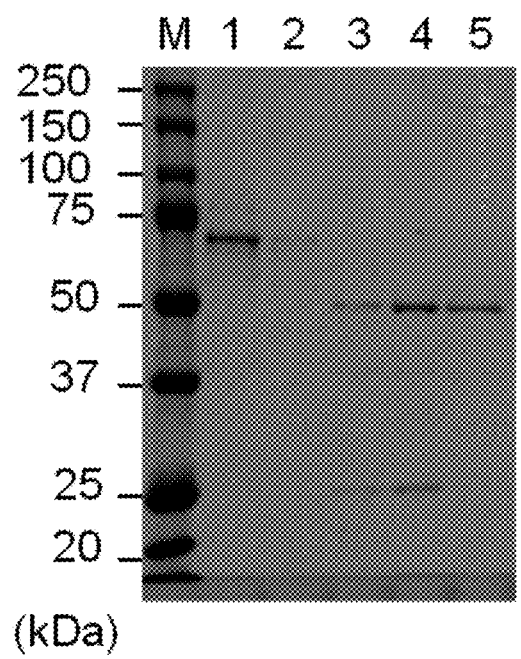
[Figure 14b]
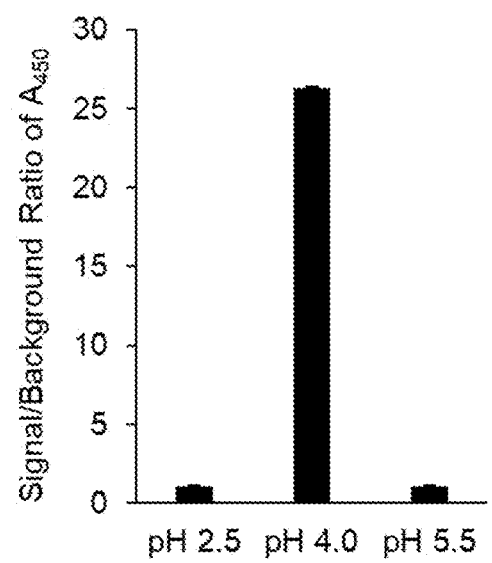

[Figure 15a]
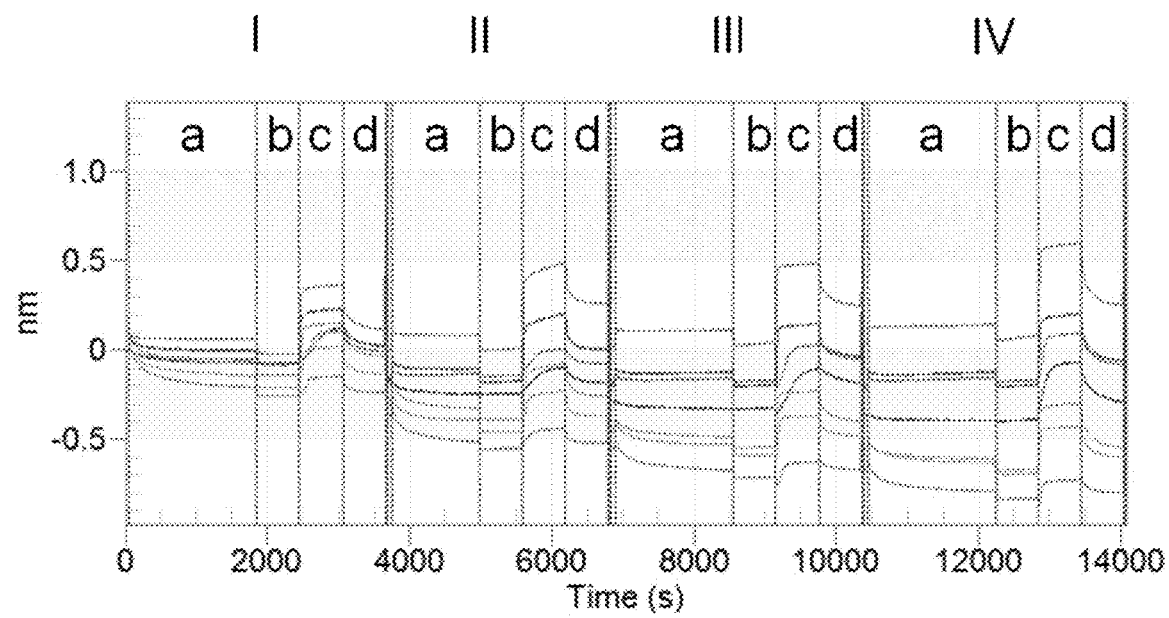
[Figure 15b]
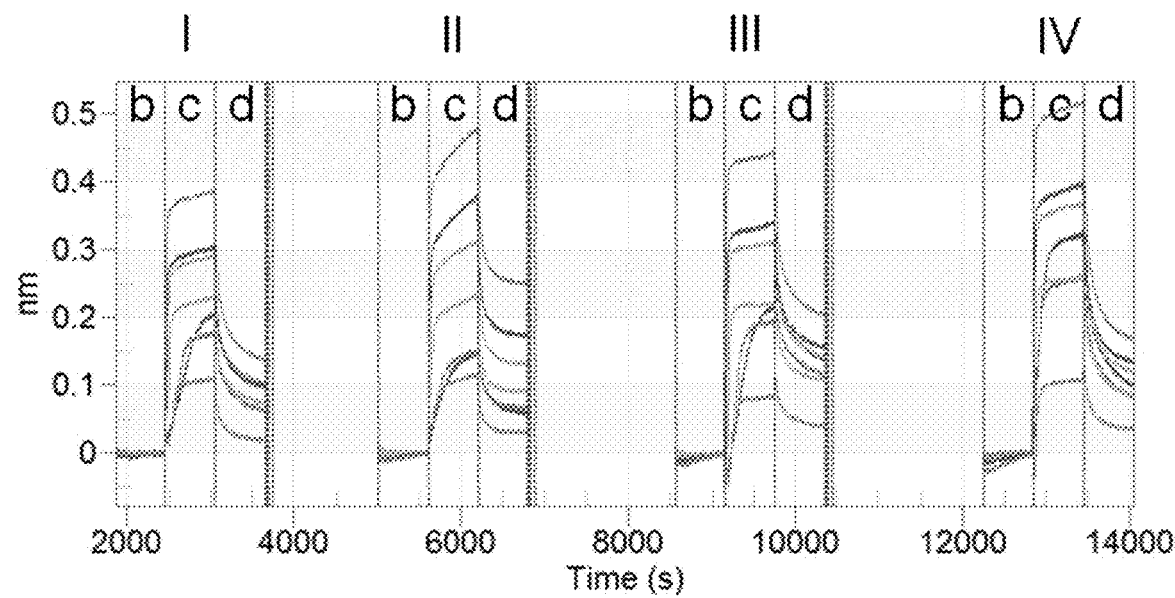

[Figure 16a]
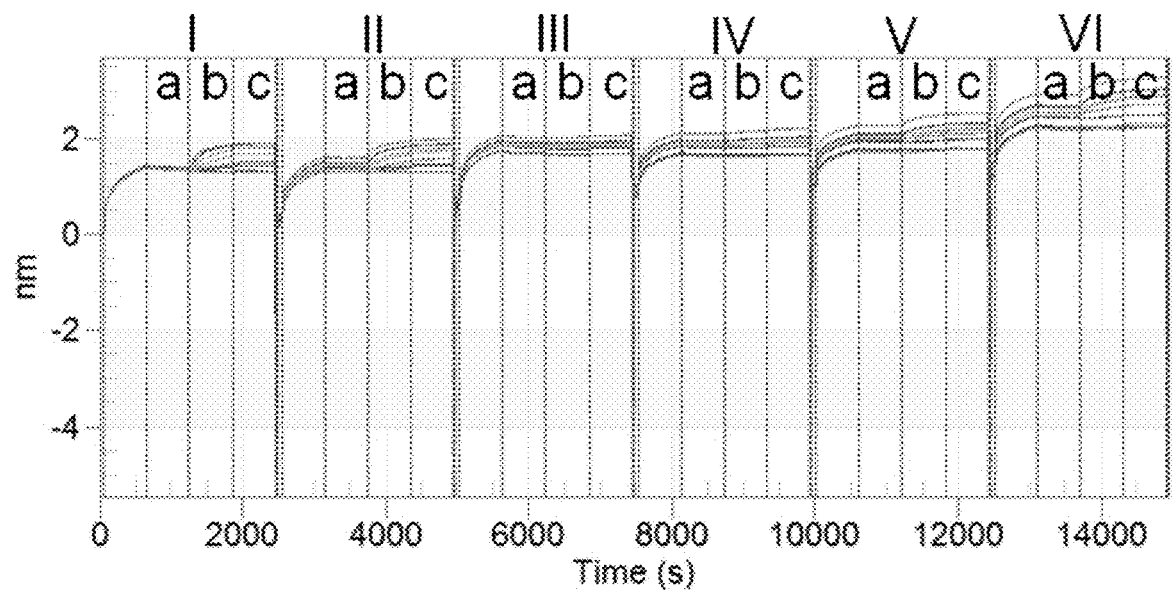
[Figure 16b]
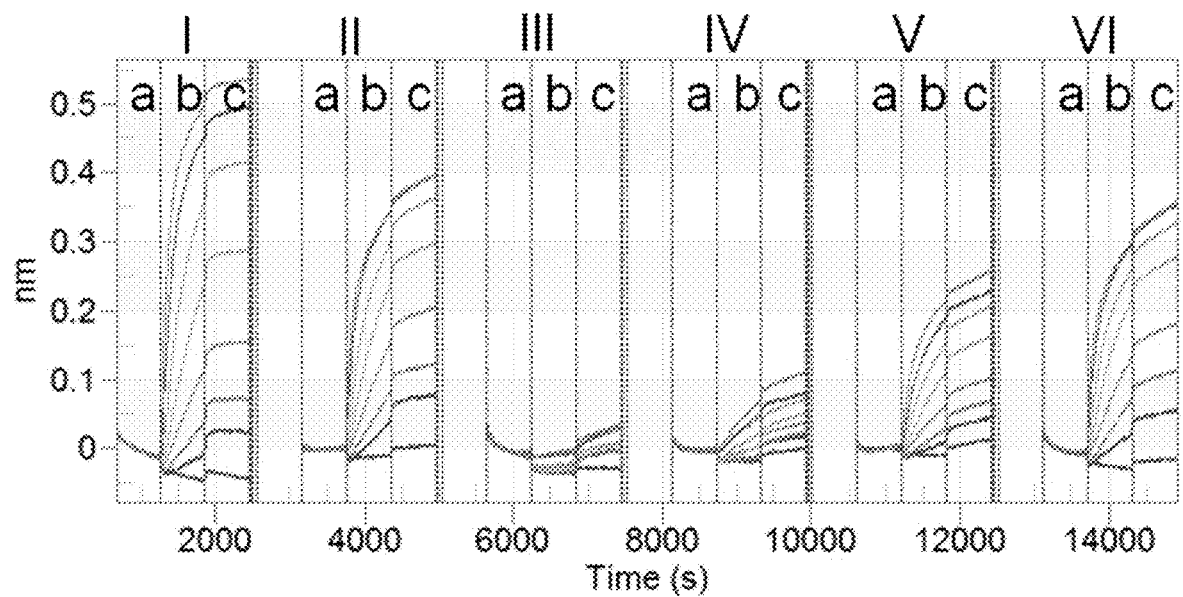

[Figure 17]
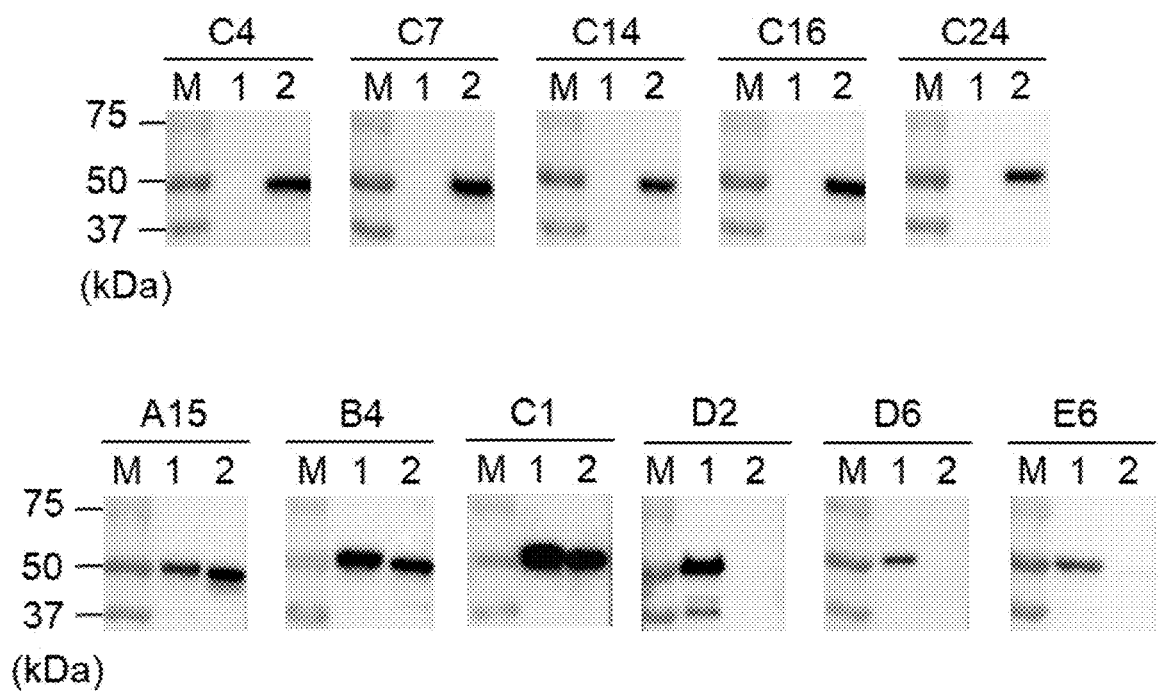

[Figure 18a]
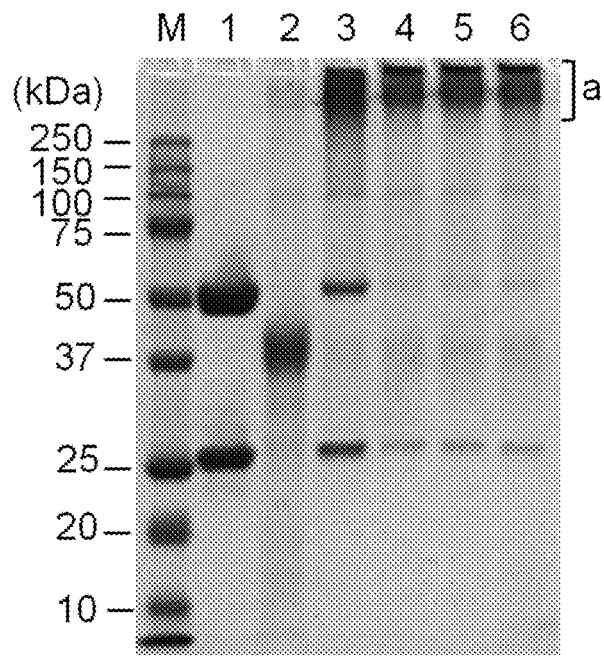
[Figure 18b]
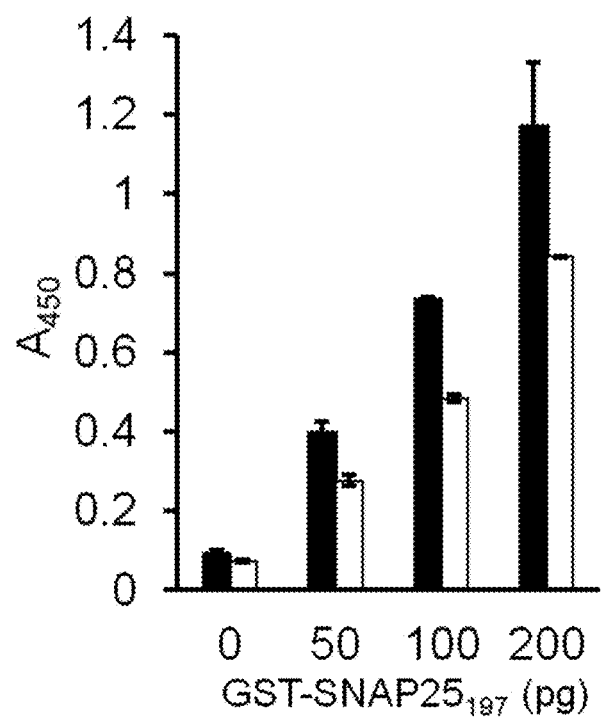

[Figure 19a]
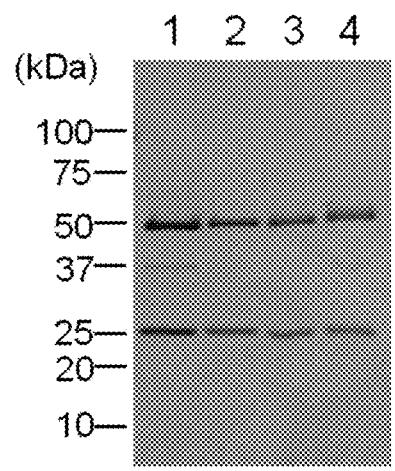
[Figure 19b]
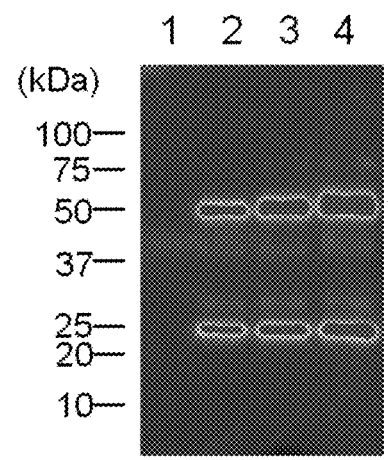

[Figure 19c]

[Figure 20a]
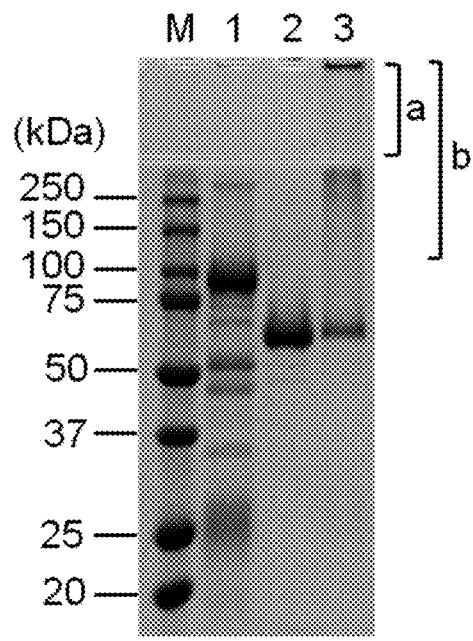
[Figure 20b]
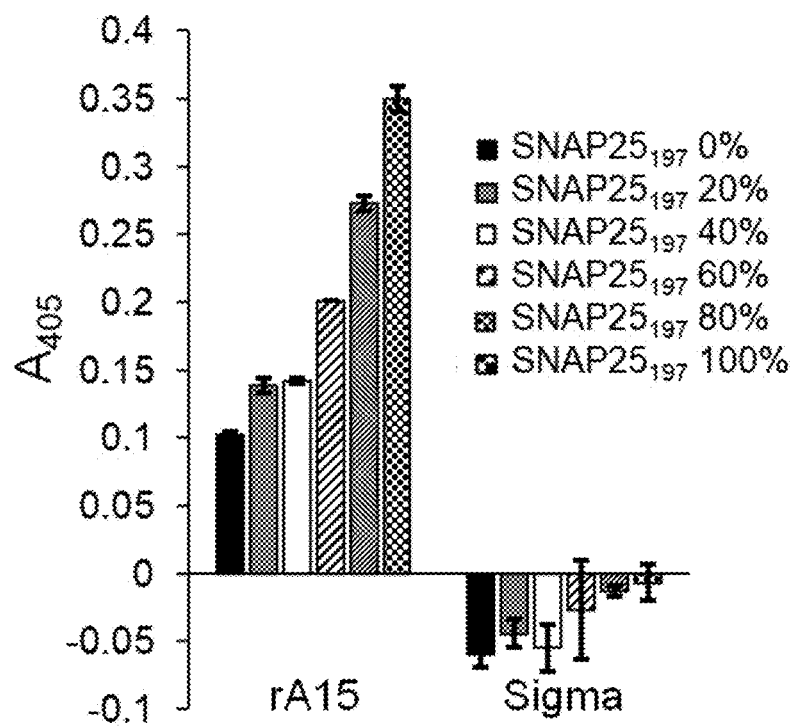

[Figure 21a]
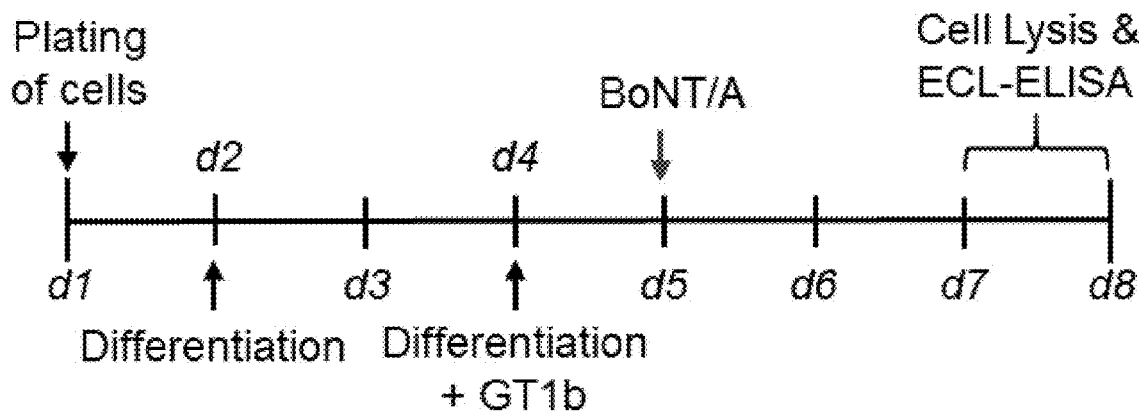
[Figure 21b]
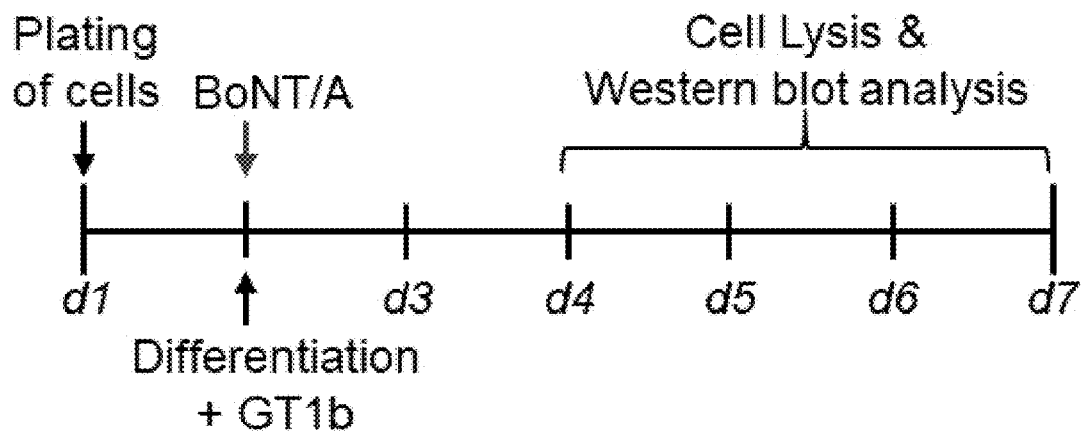
[Figure 21c]
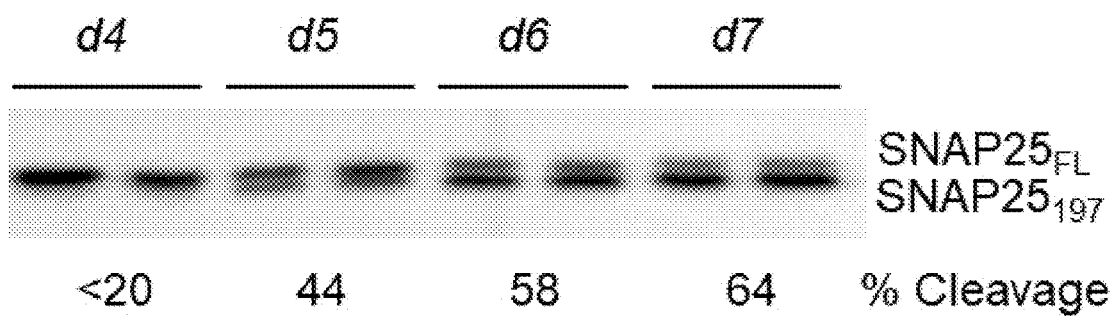

[Figure 22]
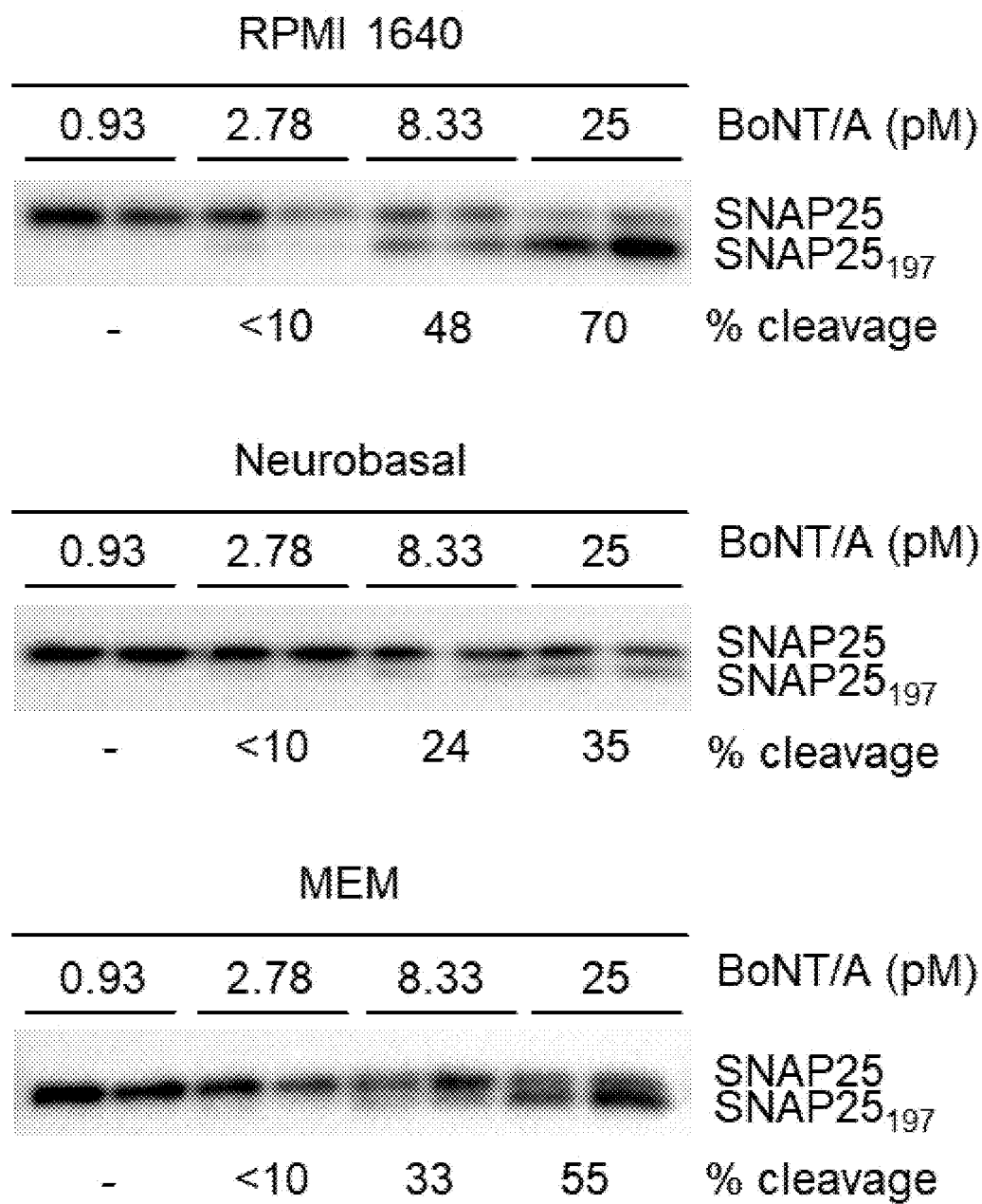

[Figure 23a]

| Sensitizer | EC50 (pM) |
|---|---|
| None | 2.51±0.39 |
| 1 mM ATP | - |
| 1 mM creatine | 2.13±0.30 |
| 1 mM lipoic acid | - |
| 5 mM arginine | 2.03±0.13 |

[Figure 23b]

| Arginine | EC50 (pM) |
|---|---|
| 0 | 2.94±0.18 |
| 2 mM | 2.60±0.31 |
| 5 mM | 1.65±0.10 |
| 10 mM | 2.34±0.41 |

[Figure 24a]
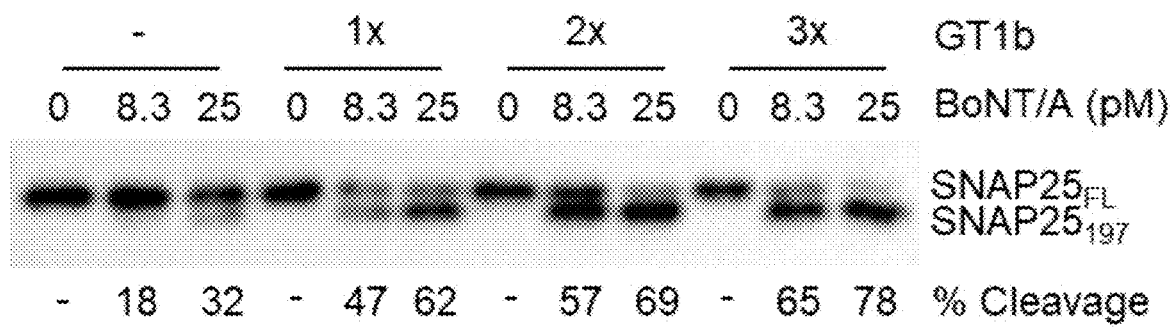
[Figure 24b]
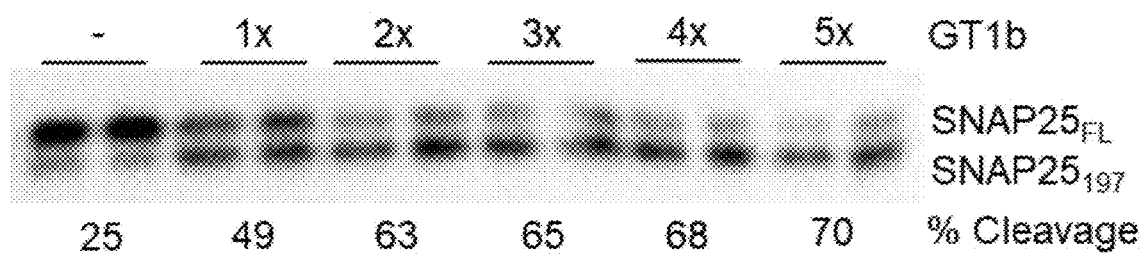
[Figure 24c]
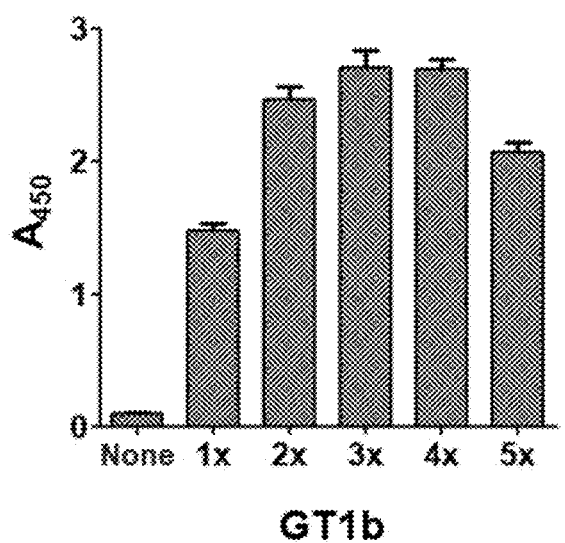

[Figure 25a]
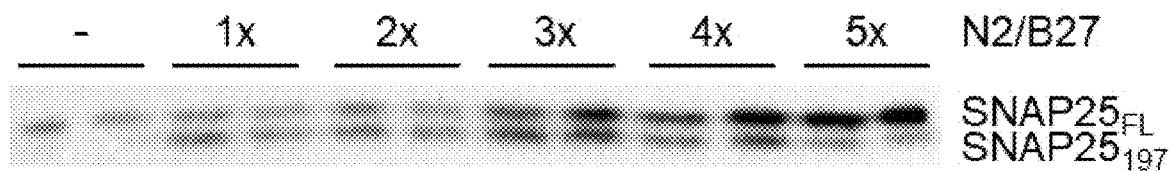
[Figure 25b]
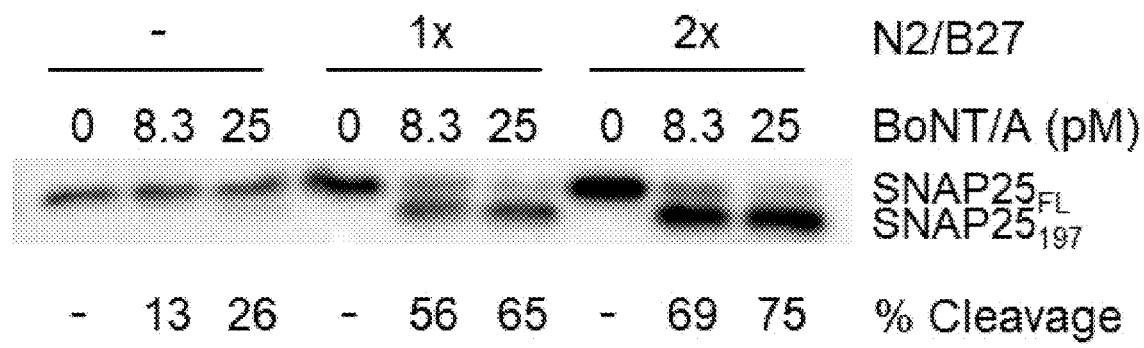

【Figure 27a】
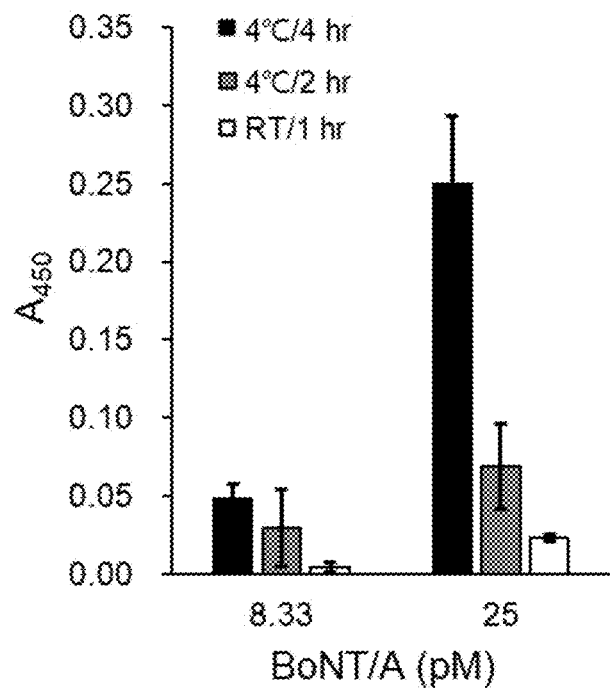
【Figure 27b】
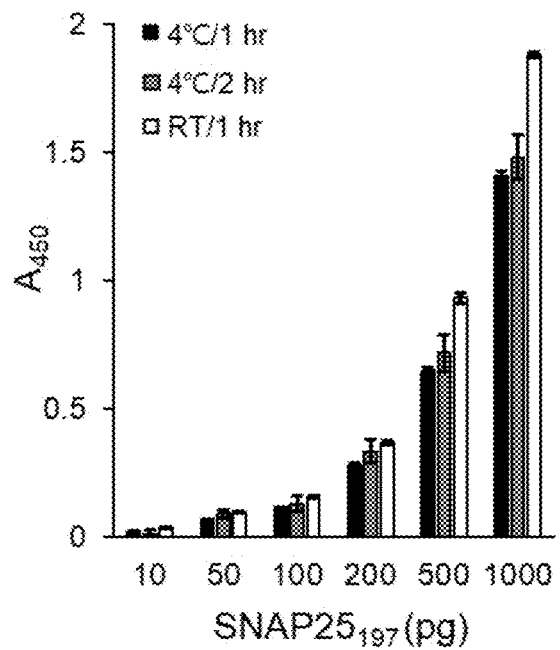

[Figure 28]
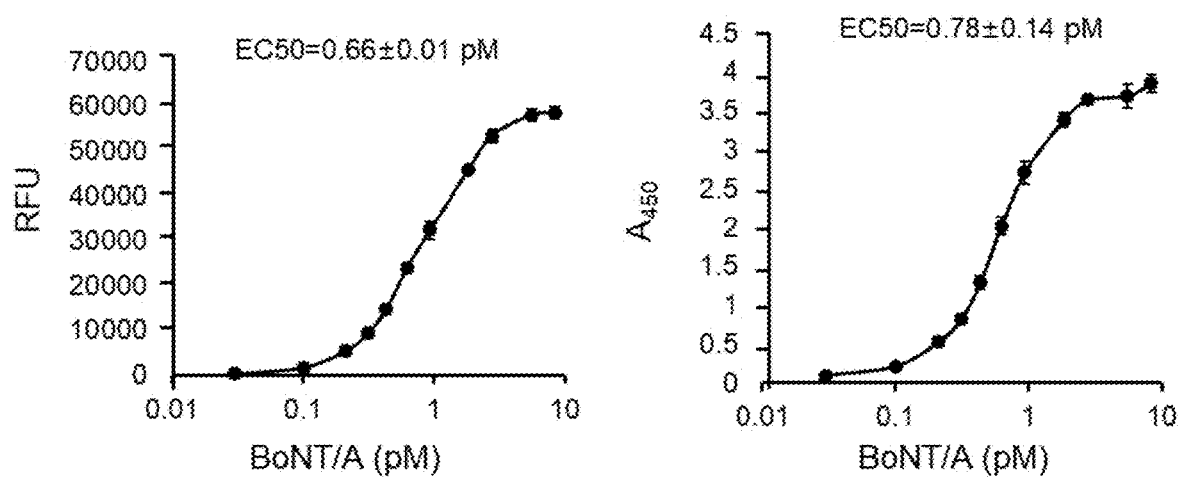

[Figure 29]

Day 1: N2-42F cell seeding in a 96-well microplate.

Day 2-6: Concomitant differentiation and BoNT/A intoxication.

Day 6: Sandwich ELISA and determination of bio-potency of BoNT/A.

Capture of both SNAP25$_{FL}$ and SNAP25$_{197}$

Detection of SNAP25$_{197}$

SEQUENCE LISTING

```
<160> NUMBER OF SEQ ID NOS: 91

<210> SEQ ID NO 1
<211> LENGTH: 13
<212> TYPE: PRT
<213> ORGANISM: clostridium botulinum

<400> SEQUENCE: 1

Met Ala Glu Asp Ala Asp Met Arg Asn Glu Leu Glu Glu
1               5                   10

<210> SEQ ID NO 2
<211> LENGTH: 13
<212> TYPE: PRT
<213> ORGANISM: clostridium botulinum

<400> SEQUENCE: 2

Met Ala Glu Asp Ala Asp Met Arg Asn Glu Leu Glu Glu
1               5                   10

<210> SEQ ID NO 3
<211> LENGTH: 20
<212> TYPE: PRT
<213> ORGANISM: clostridium botulinum

<400> SEQUENCE: 3

Asp Gln Leu Ala Asp Glu Ser Leu Glu Ser Thr Arg Arg Met Leu Gln
1               5                   10                  15

Leu Val Glu Glu
            20

<210> SEQ ID NO 4
<211> LENGTH: 20
<212> TYPE: PRT
<213> ORGANISM: clostridium botulinum

<400> SEQUENCE: 4

Asp Glu Gln Gly Glu Gln Leu Glu Arg Ile Glu Glu Gly Met Asp Gln
1               5                   10                  15

Ile Asn Lys Asp
            20

<210> SEQ ID NO 5
<211> LENGTH: 15
<212> TYPE: PRT
<213> ORGANISM: clostridium botulinum

<400> SEQUENCE: 5

Asp Glu Arg Glu Gln Met Ala Ile Ser Gly Gly Phe Ile Arg Arg
1               5                   10                  15

<210> SEQ ID NO 6
<211> LENGTH: 15
<212> TYPE: PRT
<213> ORGANISM: clostridium botulinum
```

<400> SEQUENCE: 6

Glu Ile Asp Thr Gln Asn Arg Gln Ile Asp Arg Ile Met Glu Lys
1               5                   10                  15

<210> SEQ ID NO 7
<211> LENGTH: 15
<212> TYPE: PRT
<213> ORGANISM: clostridium botulinum

<400> SEQUENCE: 7

Arg Ile Met Glu Lys Ala Asp Ser Asn Lys Thr Arg Ile Asp Glu
1               5                   10                  15

<210> SEQ ID NO 8
<211> LENGTH: 18
<212> TYPE: PRT
<213> ORGANISM: clostridium botulinum

<400> SEQUENCE: 8

Arg Ile Met Glu Lys Ala Asp Ser Asn Lys Thr Arg Ile Asp Glu Ala
1               5                   10                  15

Asn Gln

<210> SEQ ID NO 9
<211> LENGTH: 12
<212> TYPE: PRT
<213> ORGANISM: clostridium botulinum

<400> SEQUENCE: 9

Asp Ser Asn Lys Thr Arg Ile Asp Glu Ala Asn Gln
1               5                   10

<210> SEQ ID NO 10
<211> LENGTH: 13
<212> TYPE: PRT
<213> ORGANISM: clostridium botulinum

<400> SEQUENCE: 10

Lys Thr Arg Ile Asp Glu Ala Asn Gln Pro Ala Thr Lys
1               5                   10

<210> SEQ ID NO 11
<211> LENGTH: 9
<212> TYPE: PRT
<213> ORGANISM: Artificial Sequence
<220> FEATURE:
<223> OTHER INFORMATION: antibody CDR of clostridium botulinum

<400> SEQUENCE: 11

Gly Tyr Ser Ile Thr Ser Gly Tyr Tyr
1               5

<210> SEQ ID NO 12
<211> LENGTH: 8
<212> TYPE: PRT
<213> ORGANISM: Artificial Sequence
<220> FEATURE:
<223> OTHER INFORMATION: antibody CDR of clostridium botulinum

<400> SEQUENCE: 12

Gly Tyr Thr Phe Thr Asp Tyr Asn
1               5

```
<210> SEQ ID NO 13
<211> LENGTH: 8
<212> TYPE: PRT
<213> ORGANISM: Artificial Sequence
<220> FEATURE:
<223> OTHER INFORMATION: antibody CDR of clostridium botulinum

<400> SEQUENCE: 13

Gly Tyr Thr Phe Thr Asn Tyr Gly
1               5

<210> SEQ ID NO 14
<211> LENGTH: 7
<212> TYPE: PRT
<213> ORGANISM: Artificial Sequence
<220> FEATURE:
<223> OTHER INFORMATION: antibody CDR of clostridium botulinum

<400> SEQUENCE: 14

Ile Arg Tyr Asp Gly Ser Asn
1               5

<210> SEQ ID NO 15
<211> LENGTH: 8
<212> TYPE: PRT
<213> ORGANISM: Artificial Sequence
<220> FEATURE:
<223> OTHER INFORMATION: antibody CDR of clostridium botulinum

<400> SEQUENCE: 15

Ile Tyr Pro Tyr Asn Gly Asp Thr
1               5

<210> SEQ ID NO 16
<211> LENGTH: 8
<212> TYPE: PRT
<213> ORGANISM: Artificial Sequence
<220> FEATURE:
<223> OTHER INFORMATION: antibody CDR of clostridium botulinum

<400> SEQUENCE: 16

Ile Asn Thr Tyr Thr Gly Glu Pro
1               5

<210> SEQ ID NO 17
<211> LENGTH: 12
<212> TYPE: PRT
<213> ORGANISM: Artificial Sequence
<220> FEATURE:
<223> OTHER INFORMATION: antibody CDR of clostridium botulinum

<400> SEQUENCE: 17

Ala Arg Asp Arg Asp Ser Ser Tyr Tyr Phe Asp Tyr
1               5                   10

<210> SEQ ID NO 18
<211> LENGTH: 6
<212> TYPE: PRT
<213> ORGANISM: Artificial Sequence
<220> FEATURE:
<223> OTHER INFORMATION: antibody CDR of clostridium botulinum

<400> SEQUENCE: 18

Val Arg Ser Gly Asp Tyr
1               5

<210> SEQ ID NO 19
```

<211> LENGTH: 7
<212> TYPE: PRT
<213> ORGANISM: Artificial Sequence
<220> FEATURE:
<223> OTHER INFORMATION: antibody CDR of clostridium botulinum

<400> SEQUENCE: 19

Ala Arg Gly Tyr Tyr Asp Tyr
1               5

<210> SEQ ID NO 20
<211> LENGTH: 6
<212> TYPE: PRT
<213> ORGANISM: Artificial Sequence
<220> FEATURE:
<223> OTHER INFORMATION: antibody CDR of clostridium botulinum

<400> SEQUENCE: 20

Asp His Ile Asn Asn Trp
1               5

<210> SEQ ID NO 21
<211> LENGTH: 11
<212> TYPE: PRT
<213> ORGANISM: Artificial Sequence
<220> FEATURE:
<223> OTHER INFORMATION: antibody CDR of clostridium botulinum

<400> SEQUENCE: 21

Gln Ser Leu Leu Asp Ser Asn Gly Lys Thr Tyr
1               5                   10

<210> SEQ ID NO 22
<211> LENGTH: 11
<212> TYPE: PRT
<213> ORGANISM: Artificial Sequence
<220> FEATURE:
<223> OTHER INFORMATION: antibody CDR of clostridium botulinum

<400> SEQUENCE: 22

Gln Ser Leu Leu Asp Ser Asp Gly Lys Thr Tyr
1               5                   10

<210> SEQ ID NO 23
<211> LENGTH: 3
<212> TYPE: PRT
<213> ORGANISM: Artificial Sequence
<220> FEATURE:
<223> OTHER INFORMATION: antibody CDR of clostridium botulinum

<400> SEQUENCE: 23

Asp Thr Thr
1

<210> SEQ ID NO 24
<211> LENGTH: 3
<212> TYPE: PRT
<213> ORGANISM: Artificial Sequence
<220> FEATURE:
<223> OTHER INFORMATION: antibody CDR of clostridium botulinum

<400> SEQUENCE: 24

Leu Val Ser
1

<210> SEQ ID NO 25
<211> LENGTH: 9

```
<212> TYPE: PRT
<213> ORGANISM: Artificial Sequence
<220> FEATURE:
<223> OTHER INFORMATION: antibody CDR of clostridium botulinum

<400> SEQUENCE: 25

Gln Gln Tyr Trp Ser Ala Pro Pro Thr
1               5

<210> SEQ ID NO 26
<211> LENGTH: 9
<212> TYPE: PRT
<213> ORGANISM: Artificial Sequence
<220> FEATURE:
<223> OTHER INFORMATION: antibody CDR of clostridium botulinum

<400> SEQUENCE: 26

Trp Gln Gly Thr Leu Phe Pro Tyr Thr
1               5

<210> SEQ ID NO 27
<211> LENGTH: 9
<212> TYPE: PRT
<213> ORGANISM: Artificial Sequence
<220> FEATURE:
<223> OTHER INFORMATION: antibody CDR of clostridium botulinum

<400> SEQUENCE: 27

Trp Gln Gly Thr His Phe Pro Arg Thr
1               5

<210> SEQ ID NO 28
<211> LENGTH: 9
<212> TYPE: PRT
<213> ORGANISM: Artificial Sequence
<220> FEATURE:
<223> OTHER INFORMATION: antibody CDR of clostridium botulinum

<400> SEQUENCE: 28

Gly Tyr Ser Ile Thr Ser Asp Tyr Ala
1               5

<210> SEQ ID NO 29
<211> LENGTH: 8
<212> TYPE: PRT
<213> ORGANISM: Artificial Sequence
<220> FEATURE:
<223> OTHER INFORMATION: antibody CDR of clostridium botulinum

<400> SEQUENCE: 29

Gly Phe Thr Phe Asn Thr Asn Ala
1               5

<210> SEQ ID NO 30
<211> LENGTH: 8
<212> TYPE: PRT
<213> ORGANISM: Artificial Sequence
<220> FEATURE:
<223> OTHER INFORMATION: antibody CDR of clostridium botulinum

<400> SEQUENCE: 30

Gly Tyr Thr Phe Thr Asn Tyr Thr
1               5

<210> SEQ ID NO 31
<211> LENGTH: 8
<212> TYPE: PRT
```

<213> ORGANISM: Artificial Sequence
<220> FEATURE:
<223> OTHER INFORMATION: antibody CDR of clostridium botulinum

<400> SEQUENCE: 31

Gly Tyr Thr Phe Asn Thr Tyr Ala
1               5

<210> SEQ ID NO 32
<211> LENGTH: 8
<212> TYPE: PRT
<213> ORGANISM: Artificial Sequence
<220> FEATURE:
<223> OTHER INFORMATION: antibody CDR of clostridium botulinum

<400> SEQUENCE: 32

Gly Phe Thr Phe Ser Asn Tyr Gly
1               5

<210> SEQ ID NO 33
<211> LENGTH: 8
<212> TYPE: PRT
<213> ORGANISM: Artificial Sequence
<220> FEATURE:
<223> OTHER INFORMATION: antibody CDR of clostridium botulinum

<400> SEQUENCE: 33

Gly Phe Thr Phe Asn Thr Tyr Ala
1               5

<210> SEQ ID NO 34
<211> LENGTH: 7
<212> TYPE: PRT
<213> ORGANISM: Artificial Sequence
<220> FEATURE:
<223> OTHER INFORMATION: antibody CDR of clostridium botulinum

<400> SEQUENCE: 34

Ile Ser Tyr Ser Val Gly Thr
1               5

<210> SEQ ID NO 35
<211> LENGTH: 10
<212> TYPE: PRT
<213> ORGANISM: Artificial Sequence
<220> FEATURE:
<223> OTHER INFORMATION: antibody CDR of clostridium botulinum

<400> SEQUENCE: 35

Ile Arg Ser Lys Ser Asn Asn Tyr Ala Thr
1               5                   10

<210> SEQ ID NO 36
<211> LENGTH: 10
<212> TYPE: PRT
<213> ORGANISM: Artificial Sequence
<220> FEATURE:
<223> OTHER INFORMATION: antibody CDR of clostridium botulinum

<400> SEQUENCE: 36

Ile Arg Ser Lys Ser Asp Asn Tyr Ala Thr
1               5                   10

<210> SEQ ID NO 37
<211> LENGTH: 8
<212> TYPE: PRT
<213> ORGANISM: Artificial Sequence

```
<220> FEATURE:
<223> OTHER INFORMATION: antibody CDR of clostridium botulinum

<400> SEQUENCE: 37

Ile Asn Pro Ser Ser Asp Tyr Thr
1               5

<210> SEQ ID NO 38
<211> LENGTH: 10
<212> TYPE: PRT
<213> ORGANISM: Artificial Sequence
<220> FEATURE:
<223> OTHER INFORMATION: antibody CDR of clostridium botulinum

<400> SEQUENCE: 38

Ile Arg Ser Lys Ser Asn Asn Tyr Thr Thr
1               5                   10

<210> SEQ ID NO 39
<211> LENGTH: 8
<212> TYPE: PRT
<213> ORGANISM: Artificial Sequence
<220> FEATURE:
<223> OTHER INFORMATION: antibody CDR of clostridium botulinum

<400> SEQUENCE: 39

Ile Asn Ser Asn Gly Gly Thr Thr
1               5

<210> SEQ ID NO 40
<211> LENGTH: 10
<212> TYPE: PRT
<213> ORGANISM: Artificial Sequence
<220> FEATURE:
<223> OTHER INFORMATION: antibody CDR of clostridium botulinum

<400> SEQUENCE: 40

Ala Arg Lys Gly Glu Tyr Gly Phe Ala Tyr
1               5                   10

<210> SEQ ID NO 41
<211> LENGTH: 11
<212> TYPE: PRT
<213> ORGANISM: Artificial Sequence
<220> FEATURE:
<223> OTHER INFORMATION: antibody CDR of clostridium botulinum

<400> SEQUENCE: 41

Val Tyr Gly Arg Ser Tyr Gly Gly Leu Ser Tyr
1               5                   10

<210> SEQ ID NO 42
<211> LENGTH: 11
<212> TYPE: PRT
<213> ORGANISM: Artificial Sequence
<220> FEATURE:
<223> OTHER INFORMATION: antibody CDR of clostridium botulinum

<400> SEQUENCE: 42

Val Tyr Gly Arg Ser Tyr Gly Gly Leu Gly Tyr
1               5                   10

<210> SEQ ID NO 43
<211> LENGTH: 13
<212> TYPE: PRT
<213> ORGANISM: Artificial Sequence
<220> FEATURE:
```

<223> OTHER INFORMATION: antibody CDR of clostridium botulinum

<400> SEQUENCE: 43

Val Arg Gln Val Thr Thr Ala Val Gly Gly Phe Ala Tyr
1               5                   10

<210> SEQ ID NO 44
<211> LENGTH: 16
<212> TYPE: PRT
<213> ORGANISM: Artificial Sequence
<220> FEATURE:
<223> OTHER INFORMATION: antibody CDR of clostridium botulinum

<400> SEQUENCE: 44

Ala Arg Arg Ile Phe Tyr Asn Gly Arg Thr Tyr Ala Ala Met Asp Tyr
1               5                   10                  15

<210> SEQ ID NO 45
<211> LENGTH: 17
<212> TYPE: PRT
<213> ORGANISM: Artificial Sequence
<220> FEATURE:
<223> OTHER INFORMATION: antibody CDR of clostridium botulinum

<400> SEQUENCE: 45

Val Gly Gln Ile Leu Tyr Tyr Tyr Val Gly Ser Pro Ala Trp Phe Ala
1               5                   10                  15

Tyr

<210> SEQ ID NO 46
<211> LENGTH: 9
<212> TYPE: PRT
<213> ORGANISM: Artificial Sequence
<220> FEATURE:
<223> OTHER INFORMATION: antibody CDR of clostridium botulinum

<400> SEQUENCE: 46

Ala Arg Asp Arg Asp Ala Met Asp Tyr
1               5

<210> SEQ ID NO 47
<211> LENGTH: 10
<212> TYPE: PRT
<213> ORGANISM: Artificial Sequence
<220> FEATURE:
<223> OTHER INFORMATION: antibody CDR of clostridium botulinum

<400> SEQUENCE: 47

Lys Ser Val Ser Thr Ser Gly Tyr Ser Tyr
1               5                   10

<210> SEQ ID NO 48
<211> LENGTH: 10
<212> TYPE: PRT
<213> ORGANISM: Artificial Sequence
<220> FEATURE:
<223> OTHER INFORMATION: antibody CDR of clostridium botulinum

<400> SEQUENCE: 48

Lys Ser Val Ser Ser Ser Gly Tyr Ser Tyr
1               5                   10

<210> SEQ ID NO 49
<211> LENGTH: 11
<212> TYPE: PRT
<213> ORGANISM: Artificial Sequence

```
<220> FEATURE:
<223> OTHER INFORMATION: antibody CDR of clostridium botulinum

<400> SEQUENCE: 49

Gln Ser Ile Val Asn Ser His Gly Asn Thr Tyr
1               5                   10

<210> SEQ ID NO 50
<211> LENGTH: 3
<212> TYPE: PRT
<213> ORGANISM: Artificial Sequence
<220> FEATURE:
<223> OTHER INFORMATION: antibody CDR of clostridium botulinum

<400> SEQUENCE: 50

Leu Ala Ser
1

<210> SEQ ID NO 51
<211> LENGTH: 3
<212> TYPE: PRT
<213> ORGANISM: Artificial Sequence
<220> FEATURE:
<223> OTHER INFORMATION: antibody CDR of clostridium botulinum

<400> SEQUENCE: 51

Lys Val Ser
1

<210> SEQ ID NO 52
<211> LENGTH: 9
<212> TYPE: PRT
<213> ORGANISM: Artificial Sequence
<220> FEATURE:
<223> OTHER INFORMATION: antibody CDR of clostridium botulinum

<400> SEQUENCE: 52

Gln His Ser Arg Glu Leu Pro Leu Thr
1               5

<210> SEQ ID NO 53
<211> LENGTH: 9
<212> TYPE: PRT
<213> ORGANISM: Artificial Sequence
<220> FEATURE:
<223> OTHER INFORMATION: antibody CDR of clostridium botulinum

<400> SEQUENCE: 53

Gln His Ser Arg Glu Leu Pro Trp Thr
1               5

<210> SEQ ID NO 54
<211> LENGTH: 9
<212> TYPE: PRT
<213> ORGANISM: Artificial Sequence
<220> FEATURE:
<223> OTHER INFORMATION: antibody CDR of clostridium botulinum

<400> SEQUENCE: 54

Phe Gln Gly Ser His Val Pro Trp Thr
1               5

<210> SEQ ID NO 55
<211> LENGTH: 8
<212> TYPE: PRT
<213> ORGANISM: Artificial Sequence
<220> FEATURE:
```

<223> OTHER INFORMATION: antibody CDR of clostridium botulinum

<400> SEQUENCE: 55

Gly Phe Thr Phe Ser Asn Tyr Gly
1               5

<210> SEQ ID NO 56
<211> LENGTH: 8
<212> TYPE: PRT
<213> ORGANISM: Artificial Sequence
<220> FEATURE:
<223> OTHER INFORMATION: antibody CDR of clostridium botulinum

<400> SEQUENCE: 56

Gly Ile Asn Ile Lys Asp Tyr Tyr
1               5

<210> SEQ ID NO 57
<211> LENGTH: 8
<212> TYPE: PRT
<213> ORGANISM: Artificial Sequence
<220> FEATURE:
<223> OTHER INFORMATION: antibody CDR of clostridium botulinum

<400> SEQUENCE: 57

Ile Ser Ser Gly Gly Ser Tyr Thr
1               5

<210> SEQ ID NO 58
<211> LENGTH: 8
<212> TYPE: PRT
<213> ORGANISM: Artificial Sequence
<220> FEATURE:
<223> OTHER INFORMATION: antibody CDR of clostridium botulinum

<400> SEQUENCE: 58

Ile Asp Pro Gly Asn Gly Asp Ala
1               5

<210> SEQ ID NO 59
<211> LENGTH: 13
<212> TYPE: PRT
<213> ORGANISM: Artificial Sequence
<220> FEATURE:
<223> OTHER INFORMATION: antibody CDR of clostridium botulinum

<400> SEQUENCE: 59

Ala Arg His Glu Gly Gly Gly Asn Pro Tyr Phe Asp Tyr
1               5                   10

<210> SEQ ID NO 60
<211> LENGTH: 5
<212> TYPE: PRT
<213> ORGANISM: Artificial Sequence
<220> FEATURE:
<223> OTHER INFORMATION: antibody CDR of clostridium botulinum

<400> SEQUENCE: 60

Asn Glu Ile Ala Tyr
1               5

<210> SEQ ID NO 61
<211> LENGTH: 11
<212> TYPE: PRT
<213> ORGANISM: Artificial Sequence
<220> FEATURE:
<223> OTHER INFORMATION: antibody CDR of clostridium botulinum

<400> SEQUENCE: 61

Gln Ser Leu Val His Ser Asn Gly Asn Thr Tyr
1               5                   10

<210> SEQ ID NO 62
<211> LENGTH: 11
<212> TYPE: PRT
<213> ORGANISM: Artificial Sequence
<220> FEATURE:
<223> OTHER INFORMATION: antibody CDR of clostridium botulinum

<400> SEQUENCE: 62

Gln Ser Leu Leu Asp Ser Asp Gly Lys Thr Tyr
1               5                   10

<210> SEQ ID NO 63
<211> LENGTH: 3
<212> TYPE: PRT
<213> ORGANISM: Artificial Sequence
<220> FEATURE:
<223> OTHER INFORMATION: antibody CDR of clostridium botulinum

<400> SEQUENCE: 63

Lys Val Ser
1

<210> SEQ ID NO 64
<211> LENGTH: 3
<212> TYPE: PRT
<213> ORGANISM: Artificial Sequence
<220> FEATURE:
<223> OTHER INFORMATION: antibody CDR of clostridium botulinum

<400> SEQUENCE: 64

Leu Val Ser
1

<210> SEQ ID NO 65
<211> LENGTH: 9
<212> TYPE: PRT
<213> ORGANISM: Artificial Sequence
<220> FEATURE:
<223> OTHER INFORMATION: antibody CDR of clostridium botulinum

<400> SEQUENCE: 65

Ser Gln Asn Thr Leu Val Pro Trp Thr
1               5

<210> SEQ ID NO 66
<211> LENGTH: 9
<212> TYPE: PRT
<213> ORGANISM: Artificial Sequence
<220> FEATURE:
<223> OTHER INFORMATION: antibody CDR of clostridium botulinum

<400> SEQUENCE: 66

Trp Gln Gly Thr His Phe Pro Phe Thr
1               5

<210> SEQ ID NO 67
<211> LENGTH: 120
<212> TYPE: PRT
<213> ORGANISM: Artificial Sequence
<220> FEATURE:
<223> OTHER INFORMATION: antibody of clostridium botulinum

<400> SEQUENCE: 67

Glu Val Lys Leu Val Glu Ser Gly Gly Leu Val Lys Pro Gly Gly
1               5                   10                  15

Ser Leu Lys Leu Ser Cys Ala Ala Ser Gly Phe Thr Phe Ser Asn Tyr
                20                  25                  30

Gly Met Ser Trp Val Arg Gln Thr Pro Glu Lys Arg Leu Glu Trp Val
            35                  40                  45

Ala Thr Ile Ser Ser Gly Gly Ser Tyr Thr Tyr Tyr Pro Asp Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg His Glu Gly Gly Asn Pro Tyr Phe Asp Tyr Trp Gly Gln
            100                 105                 110

Gly Thr Thr Leu Thr Val Ser Ser
        115                 120

<210> SEQ ID NO 68
<211> LENGTH: 112
<212> TYPE: PRT
<213> ORGANISM: Artificial Sequence
<220> FEATURE:
<223> OTHER INFORMATION: antibody of clostridium botulinum

<400> SEQUENCE: 68

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Asn
                85                  90                  95

Thr Leu Val Pro Trp Thr Phe Gly Gly Gly Thr Lys Leu Glu Ile Lys
            100                 105                 110

<210> SEQ ID NO 69
<211> LENGTH: 112
<212> TYPE: PRT
<213> ORGANISM: Artificial Sequence
<220> FEATURE:
<223> OTHER INFORMATION: antibody of clostridium botulinum

<400> SEQUENCE: 69

Glu Val Gln Leu Gln Gln Ser Gly Ala Glu Leu Val Arg Pro Gly Ala
1               5                   10                  15

Ser Val Lys Leu Ser Cys Thr Ala Ser Gly Ile Asn Ile Lys Asp Tyr
                20                  25                  30

Tyr Met His Trp Met Lys Gln Arg Pro Glu Gln Asp Leu Glu Trp Ile
            35                  40                  45

Gly Trp Ile Asp Pro Gly Asn Gly Asp Ala Glu Tyr Ala Pro Lys Phe
        50                  55                  60

```
Gln Gly Lys Ala Thr Met Thr Ala Asp Thr Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Asn Glu Ile Ala Tyr Trp Gly Gln Gly Thr Leu Val Thr Val Ser Ala
            100                 105                 110
```

<210> SEQ ID NO 70
<211> LENGTH: 112
<212> TYPE: PRT
<213> ORGANISM: Artificial Sequence
<220> FEATURE:
<223> OTHER INFORMATION: antibody of clostridium botulinum

<400> SEQUENCE: 70

```
Asp Ile Val Met Thr Gln Ser Pro Leu Thr Leu Ser Val Thr Ile Gly
  1               5                  10                  15

Gln Pro Ala Ser Ile Ser Cys Lys Ser Ser Gln Ser Leu Leu Asp Ser
                 20                  25                  30

Asp Gly Lys Thr Tyr Leu Asn Trp Leu Leu Gln Arg Pro Gly Gln Ser
             35                  40                  45

Pro Lys Arg Leu Ile Tyr Leu Val Ser Lys Leu Asp Ser Gly Val Pro
 50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Trp Gln Gly
                 85                  90                  95

Thr His Phe Pro Phe Thr Phe Gly Ser Gly Thr Lys Leu Glu Ile Lys
            100                 105                 110
```

<210> SEQ ID NO 71
<211> LENGTH: 117
<212> TYPE: PRT
<213> ORGANISM: Artificial Sequence
<220> FEATURE:
<223> OTHER INFORMATION: antibody of clostridium botulinum

<400> SEQUENCE: 71

```
Asp Val Lys Leu Gln Glu Ser Gly Pro Gly Leu Val Lys Pro Ser Gln
  1               5                  10                  15

Ser Leu Ser Leu Thr Cys Thr Val Thr Gly Tyr Ser Ile Thr Ser Asp
                 20                  25                  30

Tyr Ala Trp Asn Trp Ile Arg Gln Phe Pro Gly Asn Lys Leu Glu Trp
             35                  40                  45

Met Gly Tyr Ile Ser Tyr Ser Val Gly Thr Arg Tyr Asn Pro Ser Leu
 50                  55                  60

Lys Ser Arg Ile Ser Ile Thr Arg Asp Thr Ser Lys Asn Gln Phe Phe
 65                  70                  75                  80

Leu Leu Leu Lys Ser Val Thr Asn Glu Asp Thr Ala Thr Tyr Phe Cys
                 85                  90                  95

Ala Arg Lys Gly Glu Tyr Gly Phe Ala Tyr Trp Gly Gln Gly Thr Leu
            100                 105                 110

Val Thr Val Ser Ala
        115
```

<210> SEQ ID NO 72
<211> LENGTH: 111
<212> TYPE: PRT
<213> ORGANISM: Artificial Sequence

```
<220> FEATURE:
<223> OTHER INFORMATION: antibody of clostridium botulinum

<400> SEQUENCE: 72

Asp Ile Val Met Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Leu Thr Phe Gly Ala Gly Thr Lys Leu Glu Leu Lys
            100                 105                 110

<210> SEQ ID NO 73
<211> LENGTH: 120
<212> TYPE: PRT
<213> ORGANISM: Artificial Sequence
<220> FEATURE:
<223> OTHER INFORMATION: antibody of clostridium botulinum

<400> SEQUENCE: 73

Gln Val Gln Leu Val Glu Thr Gly Gly Gly Leu Val Gln Pro Lys Gly
1               5                   10                  15

Ser Leu Lys Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Leu
65                  70                  75                  80

Leu Tyr Leu Gln Met Asn Asn Leu Lys Thr Glu Asp Thr Ala Met Tyr
                85                  90                  95

Tyr Cys Val Tyr Gly Arg Ser Tyr Gly Leu Ser Tyr Trp Gly Gln Gln
            100                 105                 110

Gly Thr Leu Val Thr Val Ser Ala
        115                 120

<210> SEQ ID NO 74
<211> LENGTH: 111
<212> TYPE: PRT
<213> ORGANISM: Artificial Sequence
<220> FEATURE:
<223> OTHER INFORMATION: antibody of clostridium botulinum

<400> SEQUENCE: 74

Asp Ile Val Met Thr Gln Ser Pro Ala Ser Leu Ala Val Ser Leu Gly
1               5                   10                  15

Gln Arg Ala Thr Ile Ser Cys Arg Ala Ser Lys Ser Val Ser Ser Ser
            20                  25                  30

Gly Tyr Ser Tyr Met His Trp Tyr Gln Gln Lys Pro Gly Gln Pro Pro
        35                  40                  45
```

```
Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Leu Thr Phe Gly Ala Gly Thr Lys Leu Glu Leu Lys
            100                 105                 110
```

<210> SEQ ID NO 75
<211> LENGTH: 120
<212> TYPE: PRT
<213> ORGANISM: Artificial Sequence
<220> FEATURE:
<223> OTHER INFORMATION: antibody of clostridium botulinum

<400> SEQUENCE: 75

```
Glu Val Lys Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Asn
                20                  25                  30

Ala Met Asn Trp Val Arg Gln Ala Pro Gly Lys Gly Leu Glu Trp Val
            35                  40                  45

Ala Arg Ile Arg Ser Lys Ser Asp Asn Tyr Ala Thr Tyr Tyr Ala Asp
    50                  55                  60

Ser Val Lys Asp Arg Phe Thr Ile Ser Arg Asp Asp Ser Pro Ser Met
65                  70                  75                  80

Leu Tyr Leu Gln Met Asn Asn Leu Lys Thr Glu Asp Thr Ala Met Tyr
                85                  90                  95

Tyr Cys Val Tyr Gly Arg Ser Tyr Gly Gly Leu Gly Tyr Trp Gly Gln
            100                 105                 110

Gly Thr Leu Val Thr Val Ser Ala
        115                 120
```

<210> SEQ ID NO 76
<211> LENGTH: 111
<212> TYPE: PRT
<213> ORGANISM: Artificial Sequence
<220> FEATURE:
<223> OTHER INFORMATION: antibody of clostridium botulinum

<400> SEQUENCE: 76

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
                20                  25                  30

Gly Tyr Ser Tyr Val His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Leu Thr Phe Gly Ala Gly Thr Lys Leu Glu Leu Lys
            100                 105                 110
```

<210> SEQ ID NO 77

<211> LENGTH: 122
<212> TYPE: PRT
<213> ORGANISM: Artificial Sequence
<220> FEATURE:
<223> OTHER INFORMATION: antibody of clostridium botulinum

<400> SEQUENCE: 77

Glu Val Lys Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gln Val Thr Thr Ala Val Gly Gly Phe Ala Tyr Trp
            100                 105                 110

Gly Gln Gly Thr Leu Val Thr Val Ser Glu
        115                 120

<210> SEQ ID NO 78
<211> LENGTH: 111
<212> TYPE: PRT
<213> ORGANISM: Artificial Sequence
<220> FEATURE:
<223> OTHER INFORMATION: antibody of clostridium botulinum

<400> SEQUENCE: 78

Asp Ile Val Met Thr Gln Ser Pro Ala Ser Leu Ala Val Ser Leu Gly
1               5                   10                  15

Gln Arg Thr Thr Ile Ser Cys Arg Ala Ser Lys Ser Val Ser Ser Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Leu Thr Phe Gly Ala Gly Thr Lys Leu Glu Leu Arg
            100                 105                 110

<210> SEQ ID NO 79
<211> LENGTH: 123
<212> TYPE: PRT
<213> ORGANISM: Artificial Sequence
<220> FEATURE:
<223> OTHER INFORMATION: antibody of clostridium botulinum

<400> SEQUENCE: 79

Glu Val Gln Leu Gln Gln Ser Gly Ala Glu Leu Ala Arg Pro Gly Ala
1               5                   10                  15

Ser Val Gln Met Ser Cys Lys Ala Phe Gly Tyr Thr Phe Thr Asn Tyr
            20                  25                  30

Thr Met His Trp Val Arg Gln Arg Pro Gly Gln Gly Leu Glu Trp Ile
            35                  40                  45

Gly Phe Ile Asn Pro Ser Ser Asp Tyr Thr Asn Tyr Asn Gln Lys Phe
 50                  55                  60

Lys Asp Lys Ala Thr Leu Ser Ala Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Arg Ile Phe Tyr Asn Gly Arg Thr Tyr Ala Ala Met Asp Tyr
            100                 105                 110

Trp Gly Gln Gly Thr Ser Val Thr Val Ser Ser
            115                 120

<210> SEQ ID NO 80
<211> LENGTH: 111
<212> TYPE: PRT
<213> ORGANISM: Artificial Sequence
<220> FEATURE:
<223> OTHER INFORMATION: antibody of clostridium botulinum

<400> SEQUENCE: 80

Asp Ile Val Met Thr Gln Ser Pro Ala Ser Leu Ala Val Ser Leu Gly
 1               5                  10                  15

Gln Arg Ala Thr Ile Ser Cys Arg Ala Ser Lys Ser Val Ser Ser Ser
             20                  25                  30

Gly Tyr Ser Tyr Met His Trp Tyr Gln Gln Lys Pro Gly Gln Pro Pro
         35                  40                  45

Lys Leu Leu Ile Tyr Leu Ala Ser Asn Leu Glu Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ser Arg
                 85                  90                  95

Glu Leu Pro Leu Thr Phe Gly Ala Gly Thr Lys Leu Glu Leu Lys
            100                 105                 110

<210> SEQ ID NO 81
<211> LENGTH: 126
<212> TYPE: PRT
<213> ORGANISM: Artificial Sequence
<220> FEATURE:
<223> OTHER INFORMATION: antibody of clostridium botulinum

<400> SEQUENCE: 81

Glu Val Lys Leu Val Glu Ser Gly Gly Gly Leu Val Gln Pro Lys Gly
 1               5                  10                  15

Ser Leu Lys Leu Ser Cys Ala Ala Ser Gly Tyr Thr Phe Asn Thr Tyr
             20                  25                  30

Ala Met Asn Trp Val Arg Gln Ala Pro Gly Lys Gly Leu Glu Trp Val
         35                  40                  45

Ala Arg Ile Arg Ser Lys Ser Asn Asn Tyr Thr Thr Tyr Tyr Ala Asp
 50                  55                  60

Ser Val Lys Asp Arg Phe Thr Ile Ser Arg Asp Asp Ser Gln Ser Met
 65                  70                  75                  80

Leu Tyr Leu Gln Ile Asn Asn Leu Lys Thr Glu Asp Thr Ala Met Tyr
                 85                  90                  95

Tyr Cys Val Gly Gln Ile Leu Tyr Tyr Val Gly Ser Pro Ala Trp
            100                 105                 110

Phe Ala Tyr Trp Gly Gln Gly Thr Leu Val Thr Val Ser Ala
            115                 120                 125

<210> SEQ ID NO 82
<211> LENGTH: 111
<212> TYPE: PRT
<213> ORGANISM: Artificial Sequence
<220> FEATURE:
<223> OTHER INFORMATION: antibody of clostridium botulinum

<400> SEQUENCE: 82

Asp Ile Val Met Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Phe Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Trp Thr Phe Gly Gly Gly Thr Lys Leu Glu Ile Lys
            100                 105                 110

<210> SEQ ID NO 83
<211> LENGTH: 119
<212> TYPE: PRT
<213> ORGANISM: Artificial Sequence
<220> FEATURE:
<223> OTHER INFORMATION: antibody of clostridium botulinum

<400> SEQUENCE: 83

Asp Val Lys Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Arg Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Ser Tyr Tyr Cys
                85                  90                  95

Ala Arg Asp Arg Asp Ser Ser Tyr Tyr Phe Asp Tyr Trp Gly Gln Gly
            100                 105                 110

Thr Ala Leu Thr Val Ser Ser
        115

<210> SEQ ID NO 84
<211> LENGTH: 107
<212> TYPE: PRT
<213> ORGANISM: Artificial Sequence
<220> FEATURE:
<223> OTHER INFORMATION: antibody of clostridium botulinum

<400> SEQUENCE: 84

Asp Ile Val Met Thr Gln Ser Ser Ser Tyr Leu Ser Val Ser Leu Gly
1               5                   10                  15

Gly Arg Val Thr Ile Thr Cys Lys Ala Ser Asp His Ile Asn Asn Trp
            20                  25                  30

Leu Ala Trp Tyr Gln Gln Lys Pro Gly Asn Ala Pro Arg Leu Leu Ile
        35                  40                  45

Ser Asp Thr Thr Ser Leu Glu Thr Gly Val Pro Ser Arg Phe Ser Gly
50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Ala Pro Pro
                85                  90                  95

Thr Phe Gly Gly Gly Thr Lys Leu Glu Ile Lys
            100                 105

<210> SEQ ID NO 85
<211> LENGTH: 116
<212> TYPE: PRT
<213> ORGANISM: Artificial Sequence
<220> FEATURE:
<223> OTHER INFORMATION: antibody of clostridium botulinum

<400> SEQUENCE: 85

Glu Val Gln Leu Glu Glu Ser Gly Gly Leu Val Gln Pro Gly Gly
1               5                   10                  15

Ser Leu Lys Leu Ser Cys Ala Ala Ser Gly Phe Thr Phe Ser Asn Tyr
            20                  25                  30

Gly Met Ser Trp Val Arg Gln Thr Pro Asp Lys Arg Leu Glu Leu Val
        35                  40                  45

Ala Thr Ile Asn Ser Asn Gly Gly Thr Thr Tyr Tyr Pro Asp Ser Val
50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Ser Ala Met Tyr Tyr Cys
                85                  90                  95

Ala Arg Asp Arg Asp Ala Met Asp Tyr Trp Gly Gln Gly Thr Ser Val
            100                 105                 110

Thr Val Ser Ser
        115

<210> SEQ ID NO 86
<211> LENGTH: 112
<212> TYPE: PRT
<213> ORGANISM: Artificial Sequence
<220> FEATURE:
<223> OTHER INFORMATION: antibody of clostridium botulinum

<400> SEQUENCE: 86

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Asn Ser
            20                  25                  30

His Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
            85                  90                  95

Ser His Val Pro Trp Thr Phe Gly Gly Gly Thr Lys Leu Glu Ile Lys
            100                 105                 110

<210> SEQ ID NO 87
<211> LENGTH: 113
<212> TYPE: PRT
<213> ORGANISM: Artificial Sequence
<220> FEATURE:
<223> OTHER INFORMATION: antibody of clostridium botulinum

<400> SEQUENCE: 87

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Tyr Ile Tyr Pro Tyr Asn Gly Asp Thr Gly Tyr Asn Gln Lys Phe
    50                  55                  60

Lys Ser Lys Ala Thr Leu Thr Val Asp Asn Ser Ser Thr Ala Tyr
65                  70                  75                  80

Met Glu Leu Arg Ser Leu Thr Ser Glu Asp Ser Ala Val Tyr Tyr Cys
                85                  90                  95

Val Arg Ser Gly Asp Tyr Trp Gly Gln Gly Thr Thr Leu Thr Val Ser
            100                 105                 110

Ser

<210> SEQ ID NO 88
<211> LENGTH: 112
<212> TYPE: PRT
<213> ORGANISM: Artificial Sequence
<220> FEATURE:
<223> OTHER INFORMATION: antibody of clostridium botulinum

<400> SEQUENCE: 88

Asp Val Leu Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asn Gly Lys Thr Tyr Leu Asn Trp Leu Leu Gln Arg Pro Gly Gln Ser
        35                  40                  45

Pro Ser Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr Leu Phe Pro Tyr Thr Phe Gly Gly Gly Thr Lys Leu Glu Ile Lys
            100                 105                 110

<210> SEQ ID NO 89
<211> LENGTH: 114
<212> TYPE: PRT
<213> ORGANISM: Artificial Sequence
<220> FEATURE:
<223> OTHER INFORMATION: antibody of clostridium botulinum

```
<400> SEQUENCE: 89

Gln Ile Gln Leu Ala Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Ser Trp Val Lys Gln Ala Pro Gly Lys Gly Leu Lys Trp Met
        35                  40                  45

Gly Trp Ile Asn Thr Tyr Thr Gly Glu Pro Tyr Ala Ala Asp Phe
    50                  55                  60

Lys Gly Arg Phe Ala Phe Ser Leu Glu Thr Ser Ala Ser Thr Ala Phe
65                  70                  75                  80

Leu Gln Ile Asn Asn Leu Lys Asn Glu Asp Thr Ala Thr Tyr Phe Cys
                85                  90                  95

Ala Arg Gly Tyr Tyr Asp Tyr Trp Gly Gln Gly Thr Thr Leu Thr Val
            100                 105                 110

Ser Ser

<210> SEQ ID NO 90
<211> LENGTH: 112
<212> TYPE: PRT
<213> ORGANISM: Artificial Sequence
<220> FEATURE:
<223> OTHER INFORMATION: antibody of clostridium botulinum

<400> SEQUENCE: 90

Asp Val Leu Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Arg Thr Phe Gly Gly Gly Thr Lys Leu Glu Ile Lys
            100                 105                 110

<210> SEQ ID NO 91
<211> LENGTH: 13
<212> TYPE: PRT
<213> ORGANISM: clostridium botulinum

<400> SEQUENCE: 91

Cys Asp Ser Asn Lys Thr Arg Ile Asp Glu Ala Asn Gln
1               5                   10
```

CELL-BASED METHOD FOR DETERMINING AN ACTIVITY OF BOTULINUM TOXIN

CROSS REFERENCE TO RELATED APPLICATIONS

This application is a divisional of application Ser. No. 16/245,415 filed Jan. 11, 2019, which claims priority based on Korean Patent Application No. 10-2018-0150640 filed Nov. 29, 2018, Korean Patent Application No. 10-2018-0150997 filed Nov. 29, 2018; and Korean Patent Application No. 10-2018-0159701 filed Dec. 12, 2018, the contents of which are incorporated herein by reference in their entireties.

SEQUENCE LISTING

The content of the electronically submitted sequence listing, file name: Sequence_Listing_As_Filed.txt; size: 40,187 bytes; and date of creation: Nov. 10, 2021, filed herewith, is incorporated herein by reference in its entirety.

TECHNICAL FIELD

The present invention relates to a cell-based method for determining an activity of botulinum toxin.

BACKGROUND ART

At present the mouse $LD_{50}$ bioassay ($mLD_{50}$) is a generally accepted method for detection of BoNT/A remaining in food, clinical or environmental samples. Especially, pharmaceutical industry uses $mLD_{50}$ as a standard assay to measure BoNT/A potency for aesthetic or clinical applications. However, the BoNT/A potency estimated by mLD50 are known to vary to a great extent depending on testing institutes/facilities and researchers, it is challenging to accurately and reproducibly quantify the biological potency of BoNT/A.

ZEBET meeting was held on April 27-28, in Berlin, Germany, to promote alternative approaches to $mLD_{50}$ in order to standardize the measurement of BoNT/A and also to minimize the number of test animals involved and the pain caused to them (Altern Lab Anim. 2010 August; 38(4):315-30). Consequently, many research institutes and industries in the world have embarked diverse researches to develop cell-based potency assays (CBPAs) or cell-based bioassay (CBB) which could substitute for $mLD_{50}$ with satisfactory specificity, sensitivity and reproducibility. In order to successfully establish CBPA or CBB, they have been attempting to acquire (1) monoclonal or polyclonal antibodies specific for $SNAP25_{197}$ and (2) neuronal cell lines that exhibit high sensitivities to low levels of BoNT/A (~pM).

As early as in 2004, Dr. Chapman and his coworkers invented a fluorescent reporter assay that utilized epigenetically expressed SNAP25 fused to two fluorescent proteins (Proc Natl Acad Sci USA. 2004 Oct. 12; 101(41):14701-6), which is the technology platform of BoCell™ (BioSentinel Inc). Although it is the first of its kind that enables the detection of BoNT/A endopeptidase activity in mammalian cells growing in the 96-well culture plate, BoCell™ assay is about 2-3 orders of magnitude less sensitive than mouse bioassay (Appl Environ Microbiol vol. 78,21 (2012): 7687-97).

As briefed above, there have been worldwide efforts to develop CBPAs to replace mLD50, ultimately eliminating the animal testing. Although several institutes have developed CPBA, there remain few drawbacks to overcome. Invention of much improved CBPA will not only facilitate development of diverse BoNT/A-related products but also strengthen the competitiveness of the products by giving higher levels of confidence to consumers with regards to the quality control. On the basis of this premise, we have taken multi-facet approaches to develop a more reliable CBPA.

Therefore, the present invention is directed to a cell, antibodies, and a method for determining an activity of botulinum toxin. Firstly, we employed a very stringent strategy to produce monoclonal antibodies with much higher binding affinity and specificity toward SNAP25. Of several antibodies obtained using synthetic peptides, B4 IgG and C16 IgG were selected as capture and detection antibody for CBPA, respectively. B4 IgG has a high affinity and equal specificity toward full-length SNAP25 and its cleaved form, $SNAP25_{197}$, generated by BoNT/A, whereas C16 IgG is highly specific for $SNAP25_{197}$ with no significant binding to $SNAP25_{FL}$. Secondly, through comparative analysis of 13 different neuronal cell lines, followed by an extensive clonal selection, a novel cell line, N2-42F, was established. In addition to BoNT/A sensitivity that can be compared to that of SiMa, ~24 hr of PDT and stable attachment to poly-d-lysine (PDL)-coated culture plate make N2-42F cells a very attractive and reliable host for CBPA. Thirdly, CBPA was optimized using N2-42F cells, B4 IgG as capture antibody, and C16 IgG as detection antibody, with which as low as 0.5 U potency of BoNT/A was measured per assay. Passage stability and stable maintenance/storage of N2-42F cells, and exclusive use of monoclonal antibodies as both capture and detection antibodies make this novel CBPA very reliable and reproducible.

DISCLOSURE

Technical Problem

The present invention has been made in order to solve the above-described problems occurring in the prior art, and it is an object of the present invention to provide a cell, antibodies, and a method for determining an activity of botulinum toxin.

However, the technical object to be achieved by the present invention is not limited to the above-mentioned technical object, and other objects that are not mentioned above can be clearly understood by those skilled in the art from the following description.

Technical Solution

Hereinafter, various embodiments described herein will be described with reference to figures. In the following description, numerous specific details are set forth, such as specific configurations, compositions, and processes, etc., in order to provide a thorough understanding of the present invention. However, certain embodiments may be practiced without one or more of these specific details, or in combination with other known methods and configurations. In other instances, known processes and preparation techniques have not been described in particular detail in order to not unnecessarily obscure the present invention. Reference throughout this specification to "one embodiment" or "an embodiment" means that a particular feature, configuration, composition, or characteristic described in connection with the embodiment is included in at least one embodiment of the present invention. Thus, the appearances of the phrase "in one embodiment" or "an embodiment" in various places throughout this specification are not necessarily referring to the same embodiment of the present invention. Additionally, the particular features, configurations, compositions, or characteristics may be combined in any suitable manner in one or more embodiments.

Unless otherwise specified in the specification, all the scientific and technical terms used in the specification have the same meanings as commonly understood by those skilled in the technical field to which the present invention pertains.

Allergan Inc., the manufacturer of Botox®, successfully produced monoclonal antibodies specific for $SNAP25_{197}$ and also identified a human neuroblastoma SiMa as an ideal host cell line highly sensitive to BoNT/A (PLoS One. 2012; 7(11):e49516). Using these reagents, they developed a novel CBPA to assess the stability and potency of BoNT/A, which was approved by FDA to replace mLD50 for the first time in 2010 (U.S. Pat. No. 8,455,213B2 and US2010/0204559A1). MERZ Pharma, the German manufacturer of Botulinum Toxin, developed CBA-ELISA in 2014 (WO 2014/207109A1) and obtained FDA approval in 2015. CBA-ELISA employs in-situ fixation of differentiated neuronal cells, followed by membrane permeabilization and immunological detection of endogenous SNAP25 (Synaptosomal nerve-associated protein 25).

Allergan's CBPA and MERZ's CBA-ELISA exhibit excellent sensitivities with sub-picomolar concentrations of $EC_{50}$ (i.e. <1.0 U/well) that are equivalent to mouse bioassay. Allergan's and MERZ's technology platform commonly utilize a commercial rabbit polyclonal antibody (Sigma 59684) to detect SNAP25 under their optimal conditions. Differentiated human neuroblastoma SiMa cells are exclusively used in Allergan's CBPA, while human differentiated induced pluripotent stem cells (iPS) are used as host in the standardized and optimized MERZ's CBA-ELISA. SiMa grows slowly with over 70 hrs of population doubling time (PDT). Similarly, the generation of human neuronal differentiated iPS cells is time-consuming, and moreover their storage is as difficult as generation. Thus, CBPA would become more reliable if a neuronal cell line is not only highly sensitive to BoNT/A but can be easily maintained and stored with a faster PDT. Moreover, a research group led by Dr. David Beebe at the University of Wisconsin has cast a question on the suitability of SiMa cell since it does not exhibit motor neuron-like characteristics (J Biomol Screen. 2016 January; 21(1):65-73). They developed an alternative CBPA using a motor neuron-like cell line NG108-15 that exhibited $EC_{50}$ of ~7.9 pM. Since CBPA relies on the Western blot analysis to comparatively determine endogenous levels of $SNAP25_{197}$ and $SNAP25_{FL}$, its utilization as a high-throughput assay appears to be challenging at present.

In one embodiment of the present invention, "botulinum toxin" is a neurotoxic protein produced by the bacterium *Clostridium botulinum*. The genus *Clostridium* has more than 127 species, grouped according to their morphology and functions. The anaerobic, gram-positive bacteria *Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The symptoms of botulism typically appear 18 to 36 hours after eating the foodstuffs infected with a *Clostridium botulinum* culture or spores. The botulinum toxin can apparently pass unattenuated through the lining of the gut and shows a high affinity for cholinergic motor neurons. Symptoms of botulinum toxin intoxication can progress from difficulty in walking, swallowing, and speaking to paralysis of the respiratory muscles and death.

Botulinum toxin type A is known as the most lethal natural biological agent to man. About 50 picograms of a commercially available botulinum toxin type A (purified neurotoxin complex) is an LD50 (i.e., 1unit). Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. One unit (U) of botulinum toxin is defined as the LD50 upon intraperitoneal injection into female Swiss Webster mice weighing 18 to 20 grams each.

Immunologically distinct 7 botulinum neurotoxins have been generally characterized as botulinum neurotoxin serotypes A, B, C1, D, E, F and G, each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than botulinum toxin type B. Additionally, botulinum toxin type B has been determined to be non-toxic in primates at a dose of 480 U/kg which is about 12 times the primate LD50 for botulinum toxin type A. Botulinum toxin apparently binds with high affinity to cholinergic motor neurons, is translocated into the neuron and blocks the release of acetylcholine. Additional uptake can take place through low affinity receptors, as well as by phagocytosis and pinocytosis.

Regardless of serotype, the molecular mechanism of toxin intoxication appears to be similar and to involve at least 3 steps. In the first step of the process, the toxin binds to the presynaptic membrane of the target neuron through a specific interaction between the heavy chain (the H chain or HC), and a cell surface receptor. The receptor is thought to be different for each type of botulinum toxin and for tetanus toxin. The carboxyl end segment of the HC appears to be important for targeting of the botulinum toxin to the cell surface.

In the second step, the botulinum toxin crosses the plasma membrane of the target cell. The botulinum toxin is first engulfed by the cell through receptor-mediated endocytosis, and an endosome containing the botulinum toxin is formed. The toxin then escapes the endosome into the cytoplasm of the cell. This step is thought to be mediated by the amino end segment of the heavy chain, the HN, which triggers a conformational change of the toxin in response to a pH of about 5.5 or lower. Endosomes are known to possess a proton pump which decreases intra-endosomal pH. The conformational shift exposes hydrophobic residues in the toxin, which permits the botulinum toxin to embed itself in the endosomal membrane. The botulinum toxin (or at least the light chain of the botulinum toxin) then translocates through the endosomal membrane into the cytoplasm.

The last step of the mechanism of botulinum toxin activity appears to involve reduction of the disulfide bond joining the heavy chain and the light chain. The entire toxic activity of botulinum and tetanus toxins is contained in the light chain of the holotoxin; the light chain is a zinc ($Zn^{++}$) endopeptidase which selectively cleaves proteins essential for recognition and docking of neurotransmitter-containing vesicles with the cytoplasmic surface of the plasma membrane, and fusion of the vesicles with the plasma membrane.

Tetanus neurotoxin, botulinum toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Serotype A and E cleave SNAP-25. Serotype C1 was originally thought to cleave syntaxin, but was found to cleave syntaxin and SNAP-25. Each of the botulinum toxins specifically cleaves a different bond, except type B (and tetanus toxin) which cleave the same bond. Each of these cleavages blocks the process of vesicle-membrane docking, thereby preventing exocytosis of vesicle content.

Botulinum toxins have been used in clinical settings for the treatment of neuromuscular disorders characterized by hyperactive skeletal muscles (i.e. motor disorders). In 1989, a botulinum toxin type A complex was approved by the U.S. Food and Drug Administration for the treatment of blepharospasm, strabismus and hemifacial spasm. Subsequently, a botulinum toxin type A was also approved by the FDA for the treatment of cervical dystonia and for the treatment of glabellar lines, and a botulinum toxin type B was approved for the treatment of cervical dystonia. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about 3 months, although significantly longer periods of therapeutic activity have been reported.

Although all the botulinum toxins serotypes apparently inhibit release of the neurotransmitter acetylcholine at the neuromuscular junction, they do so by affecting different neurosecretory proteins and cleaving these proteins at different sites. For example, botulinum types A and E both cleave the 25 kDa synaptosomal associated protein (SNAP-25), but they target different amino acid sequences within this protein. Botulinum toxin types B, D, F and G act on vesicle-associated membrane protein (VAMP, also called synaptobrevin), with each serotype cleaving the protein at a different site. Finally, botulinum toxin type C1 appears to cleave both syntaxin and SNAP-25. These differences in mechanism of action may affect the relative potency and/or duration of action of the various botulinum toxin serotypes. Particularly, a substrate for a botulinum toxin can be found in a variety of different cell types.

The molecular weight of the botulinum toxin, for all seven of the known botulinum toxin serotypes, is about 150 kDa. Interestingly, the botulinum toxins are released by Clostridial bacterium as complexes comprising the 150 kDa botulinum toxin protein molecule along with associated non-toxin proteins. Thus, the botulinum toxin type A complex can be produced by Clostridial bacterium as 900 kDa, 500 kDa or 300 kDa forms. Botulinum toxin types B and C1 are apparently produced as only a 700 kDa or 500 kDa complex. Botulinum toxin type D is produced as 300 kDa or 500 kDa complexes. Finally, botulinum toxin types E and F are produced as only approximately 300 kDa complexes. The complexes (i.e. molecular weight greater than about 150 kDa) are believed to contain a non-toxin hemagglutinin proteins, a non-toxin, and non-toxic non-hemagglutinin protein. These two non-toxin proteins (which along with the botulinum toxin molecule comprise the relevant neurotoxin complex) may act to provide stability against denaturation to the botulinum toxin molecule and protection against digestive acids when a botulinum toxin is ingested. Additionally, it is possible that the larger (greater than about 150 kDa molecular weight) botulinum toxin complexes result in a slower rate of diffusion of the botulinum toxin away from a site of intramuscular injection of a botulinum toxin complex.

In vitro studies have indicated that botulinum toxin inhibits potassium cation-induced release of both acetylcholine and norepinephrine from primary cell cultures of brainstem tissue. In addition, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, CGRP, substance P, and glutamate. Thus, when adequate concentrations are used, the stimulus-evoked release of most neurotransmitters can be blocked by botulinum toxin.

Botulinum toxin type A can be obtained by establishing and growing cultures of Clostridium botulinum in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can, therefore, be recovered from bacterial cultures in predominantly their active form. In contrast, botulinum toxin serotypes C1, D, and E are synthesized by nonproteolytic strains and are therefore typically inactivated when recovered from culture. Serotypes B and F are produced by both proteolytic and nonproteolytic strains, and thus can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Moreover, it is known that botulinum toxin type B has, upon intramuscular injection, a shorter duration of activity and is also less potent than botulinum toxin type A at the same dose level.

High-quality crystalline botulinum toxin type A can be produced from the Hall A strain of Clostridium botulinum with characteristics of $\geq 3 \times 10^7$ U/mg, an A260/A278 of less than 0.60 and a distinct pattern of banding on gel electrophoresis. The known Schantz process can be used to obtain crystalline botulinum toxin type A. Generally, the botulinum toxin type A complex can be isolated and purified from an anaerobic fermentation by cultivating Clostridium botulinum type A in a suitable medium. The known process can also be used, upon separation out of the non-toxin proteins, to obtain pure botulinum toxins, such as for example: purified botulinum toxin type A with an approximately 150 kDa molecular weight with a specific potency of $1-2 \times 10^8$ LD50 U/mg or greater; purified botulinum toxin type B with an approximately 156 kDa molecular weight with a specific potency of $1-2 \times 10^8$ LD50 U/mg or greater, and; purified botulinum toxin type F with an approximately 155 kDa molecular weight with a specific potency of $1-2 \times 10^7$ LD50 U/mg or greater.

Botulinum toxins and/or botulinum toxin complexes are commercially available from compound manufacturers known in the art, and pure botulinum toxin can also be used to prepare a pharmaceutical composition.

As with enzymes generally, the biological activities of the botulinum toxins (which are intracellular peptidases) are dependent, at least in part, upon their three dimensional conformation. Thus, botulinum toxin type A is detoxified by heat, various chemicals surface stretching and surface drying. Additionally, it is known that dilution of a botulinum toxin complex obtained by the known culturing, fermentation and purification to the very low toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the botulinum toxin may be used months or years after the toxin containing pharmaceutical composition is formulated, the toxin should be stabilized with a suitable stabilizing agent. Thus, as disclosed in the present invention, the development of optimal stabilizer technology is necessary to control the in vivo release of botulinum toxin to a slow release form.

It has been reported that botulinum toxin type A has been used in clinical settings as follows:

The usual duration of an intramuscular injection of botulinum toxin administered in vivo is typically about 3 to 4 months. However, in some cases, botulinum toxin subtype A can have an efficacy for up to 12 months (*European J. Neurology* 6 (Supp 4): S111-S1150:1999), and in some circumstances for as long as 27 months, when used to treat glands, such as in the treatment of hyperhydrosis.

In addition to having pharmacologic actions at the peripheral location, botulinum toxins may also have inhibitory effects in the central nervous system. Work by Weigand et al, *Nauny-Schmiedeberg's Arch. Pharmacol.* 1976; 292, 161-165, and Habermann, *Nauny-Schmiedeberg's Arch. Pharmacol.* 1974; 281, 47-56 showed that botulinum toxin is able to ascend to the spinal area by retrograde transport. As such, a botulinum toxin injected at a peripheral location, for example intramuscularly, may be retrograde transported to the spinal cord.

A botulinum toxin has also been proposed for or has been used to treat skin bone and tendon wounds (U.S. Pat. No. 6,447,787); intrathecal pain (see U.S. Pat. No. 6,113,915); various autonomic nerve disorders, including sweat gland disorders (see e.g. U.S. Pat. No. 5,766,605 and Goldman (2000), Aesthetic Plastic Surgery July-August 24(4):280-282); tension headache (U.S. Pat. No. 6,458,365); migraine headache (U.S. Pat. No. 5,714,468); post-operative pain and visceral pain (U.S. Pat. No. 6,464,986); hair growth and hair retention (U.S. Pat. No. 6,299,893); psoriasis and dermatitis (U.S. Pat. No. 5,670,484); injured muscles (U.S. Pat. No. 6,423,319); various cancers (U.S. Pat. Nos. 6,139,845 and 6,063,768), smooth muscle disorders (U.S. Pat. No. 5,437,291); nerve entrapment syndromes (US Patent Application 2003-0224019); acne (WO 03/011333); neurogenic inflammation (U.S. Pat. No. 6,063,768); optic disorders (see U.S. Pat. No. 6,265,379); pancreatic disorders (see U.S. Pat. Nos. 6,143,306 and 6,261,572); prostate disorders, including prostatic hyperplasia, prostate cancer and urinary incontinence (see U.S. Pat. Nos. 6,365,164 and 6,667,041 and Doggweiler R., et al *Botulinum toxin type A causes diffuse* and *highly selective atrophy of rat prostate*, Neurourol Urodyn 1998; 17(4):363); fibromyalgia (U.S. Pat. No. 6,623,742), and piriformis muscle syndrome (see Childers et al. (2002), American Journal of Physical Medicine & Rehabilitation, 81:751-759).

U.S. Pat. No. 5,989,545 discloses that a modified clostridial neurotoxin or fragment thereof, preferably a botulinum toxin, chemically conjugated or recombinantly fused to a particular targeting moiety can be used to treat pain by administration of the agent to the spinal cord. Additionally, it has been disclosed that targeted botulinum toxins (i.e. with a non-native binding moiety) can be used to treat various conditions (see WO 96/33273; WO 99/17806; WO 98/07864; WO 00/57897; WO 01/21213; WO 00/10598).

In addition, a botulinum toxin has been injected into the pectoral muscle to control pectoral spasm (Senior M., Botox and the management of pectoral spasm after subpectoral implant insertion, Plastic and Recon Surg, July 2000, 224-225). Controlled release toxin implants are known (see U.S. Pat. Nos. 6,306,423 and 6,312,708) as is transdermal botulinum toxin administration (U.S. patent application Ser. No. 10/194,805). It is known that a botulinum toxin can be used to: weaken the chewing or biting muscle of the mouth so that self inflicted wounds and resulting ulcers can be healed (Payne M., et al, Botulinum toxin as a novel treatment for self mutilation in Lesch-Nyhan syndrome, Ann Neurol 2002 September; 52 (3 Supp 1):S157); permit healing of benign cystic lesions or tumors (Blugerman G., et al., Multiple eccrine hidrocystomas: A new therapeutic option with botulinum toxin, Dermatol Surg 2003 May; 29(5):557-9); treat anal fissure (Jost W., Ten years' experience with botulinum toxin in anal fissure, Int J Colorectal Dis 2002 September; 17(5):298-302); and treat certain types of atopic dermatitis (Heckmann M., et al., Botulinum toxin type A injection in the treatment of lichen simplex: An open pilot study, J Am Acad Dermatol 2002 April; 46(4):617-9).

Additionally, a botulinum toxin may have the effect of reducing induced inflammatory pain in a rat formalin model (Aoki K., et al, Mechanisms of the antinociceptive effect of subcutaneous Botox: Inhibition of peripheral and central nociceptive processing, Cephalalgia 2003 September; 23(7): 649). Furthermore, it has been reported that botulinum toxin nerve blockage can cause a reduction of epidermal thickness (Li Y, et al., Sensory and motor denervation influences epidermal thickness in rat foot glabrous skin, Exp Neurol 1997; 147:452-462). Finally, it is known to administer a botulinum toxin to the foot to treat excessive foot sweating (Katsambas A., et al., Cutaneous diseases of the foot: Unapproved treatments, Clin Dermatol 2002 November-December; 20(6):689-699; Sevim, S., et al., Botulinum toxin-A therapy for palmar and plantar hyperhidrosis, Acta Neurol Belg 2002 December; 102(4):167-70), spastic toes (Suputtitada, A., Local botulinum toxin type A injections in the treatment of spastic toes, Am J Phys Med Rehabil 2002 October; 81(10):770-5), idiopathic toe walking (Tacks, L., et al., Idiopathic toe walking: Treatment with botulinum toxin A injection, Dev Med Child Neurol 2002; 44 (Suppl 91):6), and foot dystonia (Rogers J., et al., Injections of botulinum toxin A in foot dystonia, Neurology 1993 April; 43 (4 Suppl 2)).

Tetanus toxin, as wells as derivatives (i.e. with a non-native targeting moiety), fragments, hybrids and chimeras thereof can also have therapeutic utility. The tetanus toxin bears many similarities to the botulinum toxins. Thus, both the tetanus toxin and the botulinum toxins are polypeptides made by closely related species of *Clostridium* (*Clostridium tetani* and *Clostridium botulinum*, respectively). Additionally, both the tetanus toxin and the botulinum toxins are dichain proteins composed of a light chain (molecular weight: about 50 kDa) covalently bound by a single disulfide bond to a heavy chain (molecular weight: about 100 kDa). Hence, the molecular weight of tetanus toxin and of each of the 7 botulinum toxins (non-complexed) is about 150 kDa. Furthermore, for both the tetanus toxin and the botulinum toxins, the light chain bears the domain which exhibits intracellular biological (protease) activity, while the heavy chain comprises the receptor binding (immunogenic) and cell membrane translocational domains.

Further, both the tetanus toxin and the botulinum toxins exhibit a high, specific affinity for ganglioside receptors on the surface of presynaptic cholinergic neurons. Receptor-mediated endocytosis of tetanus toxin in peripheral cholinergic neurons results in retrograde axonal transport, blocking the release of inhibitory neurotransmitters from central synapses, and causing a spastic paralysis. Contrarily, it has been believed that receptor-mediated endocytosis of botulinum toxin in peripheral cholinergic neurons hardly results in retrograde transport, inhibition of acetylcholine exocytosis from the central synapses, and a flaccid paralysis. However, very recent report has suggested that botulinum toxin also can undergo retrograde transport along axons and possibly inhibit the release of acetylcholine in central synapse (Bomba-Warczak et al., Interneuronal Transfer and Distal Action of Tetanus Toxin and Botulinum Neurotoxins A and Din Central Neurons, Cell Reports, 2016 August; 16, 1974-1987).

Finally, the tetanus toxin and the botulinum toxins resemble each other in both biosynthesis and molecular architecture. Thus, there is an overall 34% identity between the protein sequences of tetanus toxin and botulinum toxin type A, and a sequence identity as high as 62% for some functional domains (Binz T. et al., The Complete Sequence of Botulinum Neurotoxin Type A and Comparison with Other Clostridial Neurotoxins, J Biological Chemistry 265 (16); 9153-9158:1990).

In one embodiment of the present invention, "acetylcholine" is an ester of choline and acetic acid, which is the first known neurotransmitter. It is distributed throughout neurons, and has a chemical formula of $C_7H_{16}NO_2$ and a molecular weight of 146.21 kDa.

Typically, only a single type of small molecule neurotransmitter is released by each type of neuron in the mammalian nervous system, although there is evidence which suggests that several neuromodulators can be released by the same neuron. The neurotransmitter acetylcholine is secreted by neurons in many areas of the brain, specifically by the large pyramidal cells of the motor cortex, several different neurons in the basal ganglia, the motor neurons that innervate the skeletal muscles, the preganglionic neurons of the autonomic nervous system (both sympathetic and parasympathetic), the bag 1 fibers of the muscle spindle fiber, the postganglionic neurons of the parasympathetic nervous system, and some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephrine. In most instances, acetylcholine has an excitatory effect. However, acetylcholine is known to have inhibitory effects at some of the peripheral parasympathetic nerve endings (for example, inhibition of heart rate by the vagal nerve).

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, when the denervated cells are permeabilized (as by electroporation) or directly injected with the toxin. Botulinum toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

In one embodiment of the present invention, "activity of botulinum toxin" means the potency of toxin. One unit (U) of botulinum toxin is defined as the amount of botulinum toxin that kills 50% of a group of mice weighing 18 to 20 g each, when measured by mouse LD50 bioassay (mLD50), a standard assay method. Botulinum toxin, particularly botulinum toxin serotype A, is the most lethal natural biological agent known to man, and is 1.8 billion times more lethal than diphtheria toxin, 600 million times more lethal than sodium cyanide, 30 million times more lethal than cobra toxin and 12 million times more lethal than cholera toxin. Thus, a difference in potency of about 20% in botulinum toxin results in a significant difference in effect, such as 360 million times diphtheria toxin, or 2.4 million times cholera toxin.

Botulinum toxin formulations got medical or cosmetic purposes are generally distributed as lyophilized formulations or liquid formulations, and have a problem in that because botulinum toxin itself is a protein, the activity thereof becomes very unstable by temperature, pH, light, physical impact, or gas (air, nitrogen, oxygen, etc.). When the potency of botulinum toxin is reduced as described above, it hardly exhibits its expected effect, and hence it is necessarily required to accurately predict the potency of botulinum toxin in a preparation step or a use step.

In one embodiment of the present invention, "antibody" is a term known in the art and refers to a specific protein molecule that is directed against an antigenic site. For the purpose of the present invention, the antibody means an antibody that binds specifically to SNAP25 protein. This antibody may be produced according to a conventional method. The antibodies of the present invention include a partial peptide that may be produced from the protein, and the partial peptide of the present invention comprises at least 7 amino acids, preferably at least 9 amino acids, more preferably at least 12 amino acids. The form of antibody according to the present invention is not specifically limited, and polyclonal antibodies, monoclonal antibodies, or portions thereof which have antigen binding ability are included in the antibodies of the present invention, and all immunoglobulin antibodies are included in the antibodies of the present invention. Furthermore, the antibodies of the present invention also include special antibodies such as humanized antibodies. The antibodies of the present invention include not only a complete antibody having light chains and heavy chains, but also a functional fragment of the antibody molecule. The expression "functional fragment of the antibody molecule" refers to a fragment having at least antigen binding ability, and examples of the functional fragment include Fab, F(ab'), F(ab') 2, Fv and the like.

In one embodiment of the present invention, the term "kit" means a set of compositions and accessories required for a specific purpose. With the respect of the purpose of the present invention, the kit of the present invention comprises either an antibody that binds specifically to $SNAP25_{FL}$ or $SNAP25_{197}$, or a composition containing the antibody, or a cell culture dish coated with the antibody, in order to measure the activity of botulinum toxin.

In one embodiment of the present invention, there is provided a cell line, clonally selected from Neuro-2a which is a parental neuronal cell line.

The present inventors have selected Neuro-2a cells having sensitivity to botulinum toxin, which is similar to that of the SiMa cell line, from 13 different neuronal cell lines, and finally selected N2-42F (accession number: KCTC 13712BP), which consistently shows high sensitivity to botulinum toxin, from the Neuro-2a cells through a clonal selection process, thereby completing the present invention.

The cell line of the present invention may be used to determine the activity of botulinum toxin or to detect botulinum toxin.

The cell line of the present invention maintains its sensitivity to botulinum toxin even if the passage continues, and thus can be used very suitably in a cell-based assay platform.

The cell line for determining the activity of botulinum toxin according to the present invention means homogeneous single cells isolated from a parental neuronal cell line corresponding to a population including various types of cells, and refers to cells having common genetic features, for example, high or low gene expression levels of a specific gene, or the like.

The cell line for determining the activity of botulinum toxin may be isolated from the parental neuronal cell line through a method such as clonal selection, or produced by regulating the expression levels of the genes. Regulation of the expression levels of the genes can be achieved by a conventional method for regulating gene expression, for example, transformation, promoter manipulation, or the like.

The parental neuronal cell line of the present invention may include any immortalized cell line derived from nerve, and may be preferably Neuro-2a cells, more preferably Neuro-2a cells (accession number: KCTC AC28106), but is not limited thereto. The Neuro-2a cells are murine neuronal cells that may generally be used to measure LD50, and the doubling time is 34 to 100 hours in conventional SiMa cells which are used to determine the activity of botulinum toxin, but is only 24 hours in the Neuro-2a cells, indicating that the Neuro-2a cells are very suitable not only for cell-based determination of the activity of botulinum toxin, but also for detection of botulinum toxin. Furthermore, the Neuro-2a cells correspond to a population containing various types of cells when observed with a microscope, and thus have the advantage of being very suitable for selection of only single cells more sensitive to botulinum toxin therefrom.

The cell line of the present invention, clonally selected from the parental neuronal cell line Neuro-2a, may be N2-42F (accession number: KCTC 13712BP), but is not limited thereto.

The cell line of the present invention for determining the activity of botulinum toxin may be used to detect botulinum toxin or determine the activity thereof. The cell line is sensitive to botulinum toxin, and thus can detect the presence or absence of botulinum toxin in a sample of interest, and can also measure the degree of toxicity of botulinum toxin depending on the concentration of botulinum toxin.

The botulinum toxin of the present invention is a neurotoxic protein produced by the bacterium *Clostridium botulinum*, and can be classified into a total of seven serotypes: A, B, C (C1, C2), D, E, F and G. The botulinum toxin affects different neurosecretory proteins depending on the serotypes and cleaves these proteins at different sites. Specifically, both botulinum toxin serotypes A and E can cleave SNAP25 (synaptosomal nerve-associated protein 25), and botulinum toxin serotypes B, D, F and G can cleave VAMP (vesicle-associated membrane protein), and botulinum toxin serotype C1 can cleave both syntaxin and SNAP25, thereby inducing neurotoxicity. Preferably, the botulinum toxin may be botulinum toxin serotype A or botulinum toxin serotype B, more preferably botulinum toxin serotype A, but is not limited thereto.

Since the botulinum toxin serotypes A and B of the present invention are purified and widely used for treatment of dystonia, aesthetic applications, and the like, and thus when the cell line of the present invention for determining the activity of botulinum toxin is used to measure the potency of botulinum toxin, there is an advantage in that the concentration at which side effects can occur can be determined, thereby solving the problems which can occur when the botulinum toxin is used for the above-described applications.

In another embodiment of the present invention, there is provided a cell-based method for determining the activity of botulinum toxin.

The method of the present invention comprises the steps of: culturing the cell line according to the present invention;

treating the cultured cell line with the botulinum toxin; and measuring the sensitivity of the botulinum toxin-treated cell line to the botulinum toxin.

The cell-based method for determining the activity of botulinum toxin of the present invention can be achieved by treating the cell line for determining the activity of the botulinum toxin with the botulinum toxin, and measuring the sensitivity of the cell line to the botulinum toxin. Thus, the description of the contents related to the cell line for determining the activity of the botulinum toxin, the botulinum toxin, the neurosecretory proteins cleaved by the botulinum toxin, the parental neuronal cell line, and the like, will be omitted in order to avoid excessive complexity of the specification due to repeated description thereof.

In the step of culturing the cell line in the present invention, the culturing of the cell line may be performed in a culture plate coated with poly-D-lysine. When the plate coated with poly-D-lysine is used, the cell line according to the present invention can be distributed uniformly, attached firmly, and maintained at a healthy cell state, compared to when using a plate which is generally used for culturing of a cell line or a plate coated with gelatin or collagen.

The step of measuring the sensitivity of the cell line to the botulinum toxin in the present invention may comprise measuring the cleavage of endogenous neurosecretory protein caused by the botulinum toxin. Specifically, in the case of botulinum toxin serotype A and serotype E, the cleavage of SNAP25 may be measured, and in the case of botulinum toxin serotypes B, D, F and G, the cleavage of VAMP may be measured, and in the case of botulinum toxin serotype C1, the cleavage of syntaxin and/or SNAP25 may be measured.

The measurement of the cleavage in the present invention may be achieved through a method of detecting a protein using an antibody specific for the cleaved peptide of the endogenous neurosecretory protein, or the like.

The antibody of the present invention means a protein molecule that can recognizes the whole or cleaved peptide of the neurosecretory protein as an antigen and can bind specifically to the neurosecretory protein, and examples thereof include polyclonal antibodies, monoclonal antibodies, and recombinant antibodies.

The method of detecting the protein, which is used in the present invention, may be any conventional method for detecting protein, and examples thereof include, but are not limited to, Western blotting assay, ELISA (enzyme linked immunosorbent assay), RIA (radioimmunoassay), radioimmunodiffusion, Ouchterlony immunodiffusion, rocket immunoelectrophoresis, immunohistostaining, immunoprecipitation assay, complement fixation assay, fluorescence activated cell sorter (FACS), protein chip assay, and the like.

In still another embodiment of the present invention, there is provided a cell-based method for detecting botulinum toxin.

The method of the present invention comprises the steps of: culturing the cell line according to the present invention; treating the cultured cell line with a sample of interest; and measuring the sensitivity of the sample-treated cell line to the botulinum toxin.

The cell-based method for detecting the botulinum toxin according to the present invention may be achieved by treating the cell line with the sample of interest instead of the botulinum toxin used in the cell-based method for determining the activity of the botulinum toxin, and measuring the sensitivity of the cell line to the botulinum toxin. Thus, the description of the contents related to the cell line for determining the activity of the botulinum toxin, the botulinum toxin, the neurosecretory proteins cleaved by the botulinum toxin, the parental neuronal cell line, the coated plate, the protein detection method, the antibody, and the like, will be omitted in order to avoid excessive complexity of the specification due to repeated description thereof.

The sample of interest which is used in the present invention is a sample expected to contain botulinum toxin, and examples thereof may include biological samples, including cell culture supernatants, blood, saliva, sputum, cerebrospinal fluids, secretions, lymphatic fluids, dialysis fluids, body fluids, urine and the like, and chemical samples containing compounds.

In still another embodiment of the present invention, there is provided an antibody that binds specifically to SNAP25, wherein the SNAP25 is SNAP25$_{FL}$ or SNAP25$_{197}$, and the antibody comprises: a heavy-chain CDR1 region which is any one selected from the group consisting of SEQ ID NOs: 11 to 13, 28 to 33, and 55 to 56; a heavy-chain CDR2 region which is any one selected from the group consisting of SEQ ID NOs: 14 to 16, 34 to 39, and 57 to 58; a heavy-chain CDR3 region which is any one selected from the group consisting of SEQ ID NOs: 17 to 19, 40 to 46, and 59 to 60; a light-chain CDR1 region which is any one selected from the group consisting of SEQ ID NOs: 20 to 22, 47 to 49, and 61 to 62; a light-chain CDR2 region which is any one selected from the group consisting of SEQ ID NOs: 23 to 24, 50 to 51, and 63 to 64; and a light-chain CDR3 region which is any one selected from the group consisting of SEQ ID NOs: 25 to 27, 52 to 54, and 65 to 66.

More specifically, the antibody is preferably an antibody that binds specifically to SNAP25$_{FL}$ and comprises: a heavy-chain CDR1 region represented by SEQ ID NO: 11; a heavy-chain CDR2 region represented by SEQ ID NO: 14; a heavy-chain CDR3 region represented by SEQ ID NO: 17; a light-chain CDR1 region represented by SEQ ID NO: 20; a light-chain CDR2 region represented by SEQ ID NO: 23; and a light-chain CDR3 region represented by SEQ ID NO: 25. More specifically, the antibody may be an antibody represented by SEQ ID NOs: 83 and 84, but is not limited thereto.

Moreover, the antibody is preferably an antibody that binds specifically to SNAP25$_{FL}$ and comprises: a heavy-chain CDR1 region represented by SEQ ID NO: 12; a heavy-chain CDR2 region represented by SEQ ID NO: 15; a heavy-chain CDR3 region represented by SEQ ID NO: 18; a light-chain CDR1 region represented by SEQ ID NO: 21; a light-chain CDR2 region represented by SEQ ID NO: 24; and a light-chain CDR3 region represented by SEQ ID NO: 26. More specifically, the antibody may be an antibody represented by SEQ ID NOs: 87 and 88, but is not limited thereto.

In addition, the antibody is preferably an antibody that binds specifically to SNAP25$_{FL}$ and comprises: a heavy-chain CDR1 region represented by SEQ ID NO: 13; a heavy-chain CDR2 region represented by SEQ ID NO: 16; a heavy-chain CDR3 region represented by SEQ ID NO: 19; a light-chain CDR1 region represented by SEQ ID NO: 22; a light-chain CDR2 region represented by SEQ ID NO: 24; and a light-chain CDR3 region represented by SEQ ID NO: 27. More specifically, the antibody may be an antibody represented by SEQ ID NOs: 89 and 90, but is not limited thereto.

In addition, the antibody is preferably an antibody that binds specifically to SNAP25$_{197}$ and comprises: a heavy-chain CDR1 region represented by SEQ ID NO: 28; a heavy-chain CDR2 region represented by SEQ ID NO: 34; a heavy-chain CDR3 region represented by SEQ ID NO: 40; a light-chain CDR1 region represented by SEQ ID NO: 47;

a light-chain CDR2 region represented by SEQ ID NO: 50; and a light-chain CDR3 region represented by SEQ ID NO: 52. More specifically, the antibody may be an antibody represented by SEQ ID NOs: 71 and 72, but is not limited thereto.

In addition, the antibody is preferably an antibody that binds specifically to SNAP25$_{197}$ and comprises: a heavy-chain CDR1 region represented by SEQ ID NO: 29; a heavy-chain CDR2 region represented by SEQ ID NO: 35; a heavy-chain CDR3 region represented by SEQ ID NO: 41; a light-chain CDR1 region represented by SEQ ID NO: 48; a light-chain CDR2 region represented by SEQ ID NO: 50; and a light-chain CDR3 region represented by SEQ ID NO: 52. More specifically, the antibody may be an antibody represented by SEQ ID NOs: 73 and 74, but is not limited thereto.

In addition, the antibody is preferably an antibody that binds specifically to SNAP25$_{197}$ and comprises: a heavy-chain CDR1 region represented by SEQ ID NO: 29; a heavy-chain CDR2 region represented by SEQ ID NO: 36; a heavy-chain CDR3 region represented by SEQ ID NO: 42; a light-chain CDR1 region represented by SEQ ID NO: 47; a light-chain CDR2 region represented by SEQ ID NO: 50; and a light-chain CDR3 region represented by SEQ ID NO: 52. More specifically, the antibody may be an antibody represented by SEQ ID NOs: 75 and 76, but is not limited thereto.

In addition, the antibody is preferably an antibody that binds specifically to SNAP25$_{197}$ and comprises: a heavy-chain CDR1 region represented by SEQ ID NO: 33; a heavy-chain CDR2 region represented by SEQ ID NO: 35; a heavy-chain CDR3 region represented by SEQ ID NO: 43; a light-chain CDR1 region represented by SEQ ID NO: 48; a light-chain CDR2 region represented by SEQ ID NO: 50; and a light-chain CDR3 region represented by SEQ ID NO: 52. More specifically, the antibody may be an antibody represented by SEQ ID NOs: 77 and 78, but is not limited thereto.

In addition, the antibody is preferably an antibody that binds specifically to SNAP25$_{197}$ and comprises: a heavy-chain CDR1 region represented by SEQ ID NO: 30; a heavy-chain CDR2 region represented by SEQ ID NO: 37; a heavy-chain CDR3 region represented by SEQ ID NO: 44; a light-chain CDR1 region represented by SEQ ID NO: 48; a light-chain CDR2 region represented by SEQ ID NO: 50; and a light-chain CDR3 region represented by SEQ ID NO: 52. More specifically, the antibody may be an antibody represented by SEQ ID NOs: 79 and 80, but is not limited thereto.

In addition, the antibody is preferably an antibody that binds specifically to SNAP25$_{197}$ and comprises: a heavy-chain CDR1 region represented by SEQ ID NO: 31; a heavy-chain CDR2 region represented by SEQ ID NO: 38; a heavy-chain CDR3 region represented by SEQ ID NO: 45; a light-chain CDR1 region represented by SEQ ID NO: 47; a light-chain CDR2 region represented by SEQ ID NO: 50; and a light-chain CDR3 region represented by SEQ ID NO: 53. More specifically, the antibody may be an antibody represented by SEQ ID NOs: 81 and 82, but is not limited thereto.

In addition, the antibody is preferably an antibody that binds specifically to SNAP25$_{197}$ and comprises: a heavy-chain CDR1 region represented by SEQ ID NO: 32; a heavy-chain CDR2 region represented by SEQ ID NO: 39; a heavy-chain CDR3 region represented by SEQ ID NO: 46; a light-chain CDR1 region represented by SEQ ID NO: 49; a light-chain CDR2 region represented by SEQ ID NO: 51; and a light-chain CDR3 region represented by SEQ ID NO: 54. More specifically, the antibody may be an antibody represented by SEQ ID NOs: 85 and 86, but is not limited thereto.

In addition, the antibody is preferably an antibody that binds specifically to SNAP25$_{FL}$ and SNAP25$_{197}$ and comprises: a heavy-chain CDR1 region represented by SEQ ID NO: 55; a heavy-chain CDR2 region represented by SEQ ID NO: 57; a heavy-chain CDR3 region represented by SEQ ID NO: 59; a light-chain CDR1 region represented by SEQ ID NO: 61; a light-chain CDR2 region represented by SEQ ID NO: 63; and a light-chain CDR3 region represented by SEQ ID NO: 65. More specifically, the antibody may be an antibody represented by SEQ ID NOs: 67 and 68, but is not limited thereto.

In addition, the antibody is preferably an antibody that binds specifically to SNAP25$_{FL}$ and SNAP25$_{197}$ and comprises: a heavy-chain CDR1 region represented by SEQ ID NO: 56; a heavy-chain CDR2 region represented by SEQ ID NO: 58; a heavy-chain CDR3 region represented by SEQ ID NO: 60; a light-chain CDR1 region represented by SEQ ID NO: 62; a light-chain CDR2 region represented by SEQ ID NO: 64; and a light-chain CDR3 region represented by SEQ ID NO: 66. More specifically, the antibody may be an antibody represented by SEQ ID NOs: 69 and 70, but is not limited thereto.

In still another embodiment of the present invention, there is provided an antibody composition comprising the antibody, or a culture dish coated with the antibody, or a kit comprising the antibody composition or the culture dish.

In still another embodiment of the present invention, there is provided a hybridoma cell capable of producing the antibody, wherein the hybridoma cell is a fusion of a spleen cell and myeloma cell of a mouse injected with any one or more peptides selected from the group consisting of SEQ ID NOs: 1 to 10.

In still another embodiment of the present invention, there is provided a method for determining the activity of botulinum toxin, comprising the steps of: (a) treating a neuronal cell with the botulinum toxin; and (b) measuring SNAP25$_{FL}$ or SNAP25$_{197}$ in the neuronal cell by any one or more antibodies selected from among antibodies represented by SEQ ID NOs: 67 to 90, wherein the botulinum toxin is botulinum toxin type A.

In still another embodiment of the present invention, there is provided a method for detecting botulinum toxin, comprising the steps of: (a) treating a neuronal cell with a sample of interest; (b) measuring SNAP25$_{197}$ in the neuronal cell by any one or more antibodies selected from among antibodies represented by SEQ ID NOs: 67 to 82, SEQ ID NO: 85, or SEQ ID NO: 86; and (c) determining that when SNAP25$_{197}$ is measured, the botulinum toxin is present in the sample, wherein the botulinum toxin is botulinum toxin type A.

In still another embodiment of the present invention, there is provided a cell-based method for analyzing the potency of neurotoxin, comprising the steps of: (a) culturing a Neuro-2a-derived neuronal cell line; (b) treating the neuronal cell line with the neurotoxin; (c) treating the neuronal cell line or a sample, obtained from the neuronal cell line, with an antibody that binds specifically to SNAP25$_{FL}$ and SNAP25$_{197}$; and (d) treating the neuronal cell line of step (c) with an antibody that binds specifically to SNAP25$_{197}$ without binding to SNAP25$_{FL}$, wherein the Neuro-2a-derived cell line is a N2-42F cell line (accession number: KCTC 13712BP), the neurotoxin is botulinum toxin, and the neurotoxin in step (b) is diluted with a medium containing GT1b (ganglioside GT1b trisodium salt) and used to treat the cell line.

The antibody used in step (c) of the cell-based method for analyzing the potency of the neurotoxin comprises: a heavy-chain CDR1 region consisting of SEQ ID NO: 55 or 56; a heavy-chain CDR2 region consisting of SEQ ID NO: 57 or 58; a heavy-chain CDR3 region consisting of SEQ ID NO: 59 or 60; a light-chain CDR1 region consisting of SEQ ID NO: 61 or 62; a light-chain CDR2 region consisting of SEQ ID NO: 63 or 64; and a light-chain CDR3 region consisting of SEQ ID NO: 65 or 66. More specifically, the antibody used in step (c) of the cell-based method for analyzing the potency of the neurotoxin comprises: a heavy-chain CDR1 region composed of SEQ ID NO: 55; a heavy-chain CDR2 region consisting of SEQ ID NO: 57; a heavy-chain CDR3 region consisting of SEQ ID NO: 59; a light-chain CDR1 region consisting of SEQ ID NO: 61; a light-chain CDR2 region consisting of SEQ ID NO: 63; and a light-chain CDR3 region consisting of SEQ ID NO: 65. In addition, the antibody used in step (c) of the cell-based method for analyzing the potency of the neurotoxin comprises: a heavy-chain CDR1 region consisting of SEQ ID NO: 56; a heavy-chain CDR2 region consisting of SEQ ID NO: 58; a heavy-chain CDR3 region consisting of SEQ ID NO: 60; a light-chain CDR1 region consisting of SEQ ID NO: 62; a light-chain CDR2 region consisting of SEQ ID NO: 64; and a light-chain CDR3 region consisting of SEQ ID NO: 66.

In addition, the antibody used in step (d) of the cell-based method for analyzing the potency of the neurotoxin comprises: a heavy-chain CDR1 region composed of any one selected from the group consisting of SEQ ID NOs: 28 to 33; a heavy-chain CDR2 region composed of any one selected from the group consisting of SEQ ID NOs: 34 to 39; a heavy-chain CDR3 region composed of any one selected from the group consisting of SEQ ID NOs: 40 to 46; a light-chain CDR1 region composed of any one selected from the group consisting of SEQ ID NOs: 47 to 49; a light-chain CDR2 region composed of any one selected from the group consisting of SEQ ID NOs: 50 to 51; and a light-chain CDR3 region composed of any one selected from the group consisting of SEQ ID NOs: 52 to 54. More specifically, the antibody used in step (d) of the cell-based method for analyzing the potency of the neurotoxin comprises: a heavy-chain CDR1 region consisting of SEQ ID NO: 28; a heavy-chain CDR2 region consisting of SEQ ID NO: 34; a heavy-chain CDR3 region consisting of SEQ ID NO: 40; a light-chain CDR1 region consisting of SEQ ID NO: 47; a light-chain CDR2 region consisting of SEQ ID NO: 50; and a light-chain CDR3 region consisting of SEQ ID NO: 52. In addition, the antibody used in step (d) of the cell-based method for analyzing the potency of the neurotoxin comprises: a heavy-chain CDR1 region consisting of SEQ ID NO: 29; a heavy-chain CDR2 region consisting of SEQ ID NO: 35; a heavy-chain CDR3 region consisting of SEQ ID NO: 41; a light-chain CDR1 region consisting of SEQ ID NO: 48; a light-chain CDR2 region consisting of SEQ ID NO: 50; and a light-chain CDR3 region consisting of SEQ ID NO: 52. In addition, the antibody used in step (d) of the cell-based method for analyzing the potency of the neurotoxin comprises: a heavy-chain CDR1 region consisting of SEQ ID NO: 29; a heavy-chain CDR2 region consisting of SEQ ID NO: 36; a heavy-chain CDR3 region consisting of SEQ ID NO: 42; a light-chain CDR1 region consisting of SEQ ID NO: 47; a light-chain CDR2 region consisting of SEQ ID NO: 50; and a light-chain CDR3 region consisting of SEQ ID NO: 52. Furthermore, the antibody used in step (d) of the cell-based method for analyzing the potency of the neurotoxin comprises: a heavy-chain CDR1 region consisting of SEQ ID NO: 33; a heavy-chain CDR2 region consisting of SEQ ID NO: 35; a heavy-chain CDR3 region consisting of SEQ ID NO: 43; a light-chain CDR1 region consisting of SEQ ID NO: 48; a light-chain CDR2 region consisting of SEQ ID NO: 50; and a light-chain CDR3 region consisting of SEQ ID NO: 52. Moreover, the antibody used in step (d) of the cell-based method for analyzing the potency of the neurotoxin comprises: a heavy-chain CDR1 region consisting of SEQ ID NO: 30; a heavy-chain CDR2 region consisting of SEQ ID NO: 37; a heavy-chain CDR3 region consisting of SEQ ID NO: 44; a light-chain CDR1 region consisting of SEQ ID NO: 48; a light-chain CDR2 region consisting of SEQ ID NO: 50; and a light-chain CDR3 region consisting of SEQ ID NO: 52. In addition, the antibody used in step (d) of the cell-based method for analyzing the potency of the neurotoxin comprises: a heavy-chain CDR1 region consisting of SEQ ID NO: 31; a heavy-chain CDR2 region consisting of SEQ ID NO: 38; a heavy-chain CDR3 region consisting of SEQ ID NO: 45; a light-chain CDR1 region consisting of SEQ ID NO: 47; a light-chain CDR2 region consisting of SEQ ID NO: 50; and a light-chain CDR3 region consisting of SEQ ID NO: 53. In addition, the antibody used in step (d) of the cell-based method for analyzing the potency of the neurotoxin comprises: a heavy-chain CDR1 region consisting of SEQ ID NO: 32; a heavy-chain CDR2 region consisting of SEQ ID NO: 39; a heavy-chain CDR3 region consisting of SEQ ID NO: 46; a light-chain CDR1 region consisting of SEQ ID NO: 49; a light-chain CDR2 region consisting of SEQ ID NO: 51; and a light-chain CDR3 region consisting of SEQ ID NO: 54.

In still another embodiment of the present invention, there is provided a cell culture medium for treating a neuronal cell with neurotoxin, containing GT1b (ganglioside GT1b trisodium salt). The concentration of GT1b in the cell culture medium may be 25 to 75 μg/ml, and the cell culture medium further contains creatine and arginine. Furthermore, the concentration of creatine in the cell culture medium may be 0.1 to 10 mM, and the concentration of arginine in the cell culture medium may be 0.5 to 50 mM. In addition, the cell culture medium may be RPMI 1640 (Roswell Park Memorial Institute 1640) medium.

Hereinafter, each step of the present invention will be described in detail.

Advantageous Effects

Recently, there has been a rapid increase in the demand for botulinum toxin for medical and cosmetic purposes, but there is no stable and reproducible cell-based assay method for measuring the potency of botulinum toxin. Because botulinum toxin is a very potent neurotoxin protein, the development of highly specific and sensitive cells and antibodies is particularly required for accurate cell-based measurement of the potency of the botulinum toxin.

The present invention relates to an antibody for determining the activity of botulinum toxin and an antibody composition comprising the same. A novel cell line according to the present invention has a significantly short doubling time compared to conventional SiMa cells which are used to determine the activity of botulinum toxin or to detect botulinum toxin, and also has significantly high sensitivity to botulinum toxin compared to the parental cell line, indicating that it is very suitable for cell-based determination or detection of the activity of botulinum toxin. Furthermore, the cell line according to the present invention can be attached to and cultured stably in a culture dish coated with poly-d-lysine (PDL), and thus can be very effectively used for cell-based determination or detection of the activity of botulinum toxin.

An anti-botulinum toxin antibody according to the present invention is a monoclonal antibody having binding specificity for ① $SNAP25_{FL}$, ② $SNAP25_{197}$, or ③ $SNAP25_{FL}$ and $SNAP25_{197}$, and has significantly excellent specificity and sensitivity. Thus, it is expected to be actively used in the pharmaceutical and cosmetic fields.

Moreover, the present invention relates to an optimal cell-based potency assay (CBPA) which uses N2-42F cells and a monoclonal antibody having a significantly high binding affinity and specificity for SNAP25, and this CBPA can measure the potency of 0.5 U or less of botulinum toxin. The CBPA employing the cells and antibody of the present invention is expected to become a highly reliable and reproducible cell-based potency assay for botulinum toxin.

DESCRIPTION OF DRAWINGS

FIG. 1 shows the results of Western blot analysis performed to measure sensitivity to botulinum toxin A (BoNT/A) in neuronal cells according to one example of the present invention. Lane M represents a protein size marker; lane 1 represents the expression level of SNAP25 protein in a total cell lysate not intoxicated with BoNT/A; and lane 2 represents the expression level of SNAP25 protein in a total cell lysate intoxicated with BoNT/A. In addition, N2a represents Neuro-2a cells, and K-BM1 represents KP-N-RT-BM-1 cells.

FIG. 2 shows the results of Western blot analysis performed to examine the degree of cleavage of SNAP25 confirmed in a three-step clonal selection process according to one example of the present invention. In $2^{nd}$ clonal selection, only clone 42 showing the significant cleavage of SNAP25 caused by BoNT/A was selected from among 6 clones including clone 42, and in $3^{rd}$ clonal selection, clone 24 (42F) consistently shows the cleavage of SNAP25 by BoNT/A in a plurality of the same experiments.

FIG. 3 is a graph showing the results of measuring the doubling time between N2-42F cells and their parental Neruo-2a cells according to one example of the present invention.

FIG. 4 shows 20× images of Neruo-2a (which is a parental cell line), SiMa cells and clone N2-42F imaged using Leica DMi8, when reached 60% confluence, in order to confirm the morphology of the cells according to one example of the present invention.

FIG. 5 shows images of N2-42F cultured in plates coated with each of collagen type IV, gelatin and poly-D-lysine, according to one example of the present invention.

FIGS. 6a and 6b show the results of Western blot analysis performed to examine the degree of cleavage of SNAP25, which appears when SiMa cells and N2-42F were treated with various concentrations of BoNT/A, according to one example of the present invention, and the degree of cleavage of SANP25 or Vamp2, which appears when N2-42F and Neuro-2a were treated with various types of botulinum toxin.

FIGS. 7a and 7b shows the results of Western blot analysis performed to examine the passage stability of N2-42F obtained through the clonal selection process of the present invention, according to one example of the present invention.

FIG. 8 is a schematic view showing the positions of SNAP25 antigen peptides for producing a monoclonal or polyclonal antibody using synthetic peptides according to one example of the present invention.

FIG. 9 is a schematic view showing a process for forming hybridoma cells for producing a monoclonal antibody, and a process for screening clones, according to one example of the present invention.

FIGS. 10a and 10b show the results of initially screening hybridoma cells using ELISA in order to produce a monoclonal antibody according to one example of the present invention.

FIGS. 11a to 11c show the results of re-screening cells for single-cell clone production from the initial hybridoma cell screening results according to one example of the present invention.

FIGS. 12a to 12c show the results of second re-selection for producing single-cell clones according to one example of the present invention.

FIGS. 13a to 13c show the results of third re-selection for producing single-cell clones according to one example of the present invention.

FIGS. 14a and 14b shows the pattern of IgG isolated from rabbit serum protein for producing a polyclonal antibody according to one example of the present invention. In FIG. 14a, lane M represents a size marker; lane 1 represents flow-through; lane 2 represents a pool of eluted IgG at pH 5.5; lane 3 represents a pool of eluted IgG at pH 4.0; lane 4 represents a pool of eluted IgG at pH 2.5; and lane 5 represents a pool of eluted IgG at pH 11.5.

FIGS. 15a and 15b show the results of kinetic analysis of monoclonal antibodies produced in the present invention, according to one example of the present invention. In FIG. 15, IgGs loaded on AMC biosensors include C16 IgG (I), C24 IgG (II), C4 IgG (III), and C7 IgG (IV); a represents antibody loading; b represents washing; c represents association of antigen; and d represents dissociation of antigen.

FIGS. 16a and 16b show the results of kinetic analysis of monoclonal antibodies, produced in the present invention and associated with and dissociated from serially diluted recombinant GST-SNAP25, according to one example of the present invention. In FIG. 16, IgGs loaded on AMC biosensors include C14 (I), C24 (II), D2 (III), D6 (IV), E6 (V), and A15 (VI); a represents antibody loading; b represents association of antigen; and c represents dissociation of antigen.

FIG. 17 shows the results of Western blot analysis performed to examine the antigen binding specificity of monoclonal antibodies produced in the present invention, according to one example of the present invention. In FIG. 17, lane 1 represents $SNAP25_{FL}$, and lane 2 represents GST-$SNAP25_{197}$.

FIGS. 18a and 18b show the results of Western blot analysis performed to examine the antigen binding specificity of a monoclonal antibody, produced in the present invention and conjugated with HRP, according to one example of the present invention. In FIG. 18a, lane M represents a size marker; lane 1 represents unconjugated C16 IgG (9 mg); lane 2 represents activated HRP (4 mg); lane 3 represents C16 IgG/HRP mixture (C16 IgG-HRP) before incubation (4.5 mg); lane 4 represents C16 IgG-HRP after incubation (4.5 mg); lane 5 represents C16 IgG-HRP after blocking (4.3 mg); lane 6 represents C16 IgG-HRP after removal of free HRP by dialysis (4.3 mg); and a represents C16 IgG-HRP conjugate.

FIGS. 19a to 19c show the results of SDS-PAGE electrophoresis of a monoclonal antibody, produced in the present invention and conjugated with biotin, according to one example of the present invention. In FIGS. 19a and 19b, lane M represents a size marker; lane 1 represents A15 IgG alone; lane 2 represents A15 IgG conjugated with 0.1 mM biotin; lane 3 represents A15 IgG conjugated with 0.25 mM biotin; and lane 4 represents A15 IgG conjugated with 0.5 mM biotin.

FIGS. 20a and 20b shows the results of SDS-PAGE electrophoresis of a polyclonal antibody, produced in the present invention and crosslinked with AP, according to one example of the present invention. In FIG. 20a, lane M represents a size marker; lane 1 represents unconjugated IgG; lane 2 represents AP; lane 3 represents AP-IgG conjugates; a represents the stacking gel portion of polyacrylamide gel; and b represents AP-IgG conjugates.

FIGS. 21a to 21c show the results of optimizing intoxidation time in a method of determining the activity of botulinum toxin, according to one example of the present invention.

FIG. 22 shows the results of optimizing intoxidation medium in a method of determining the activity of botulinum toxin, according to one example of the present invention.

FIGS. 23a and 23b show the results of optimizing a sensitizer in a method of determining the activity of botulinum toxin, according to one example of the present invention.

FIGS. 24a to 24c show the results of optimizing GT1b in a method of determining the activity of botulinum toxin, according to one example of the present invention.

FIGS. 25a and 25b show the results of optimizing N2/B27 in a method of determining the activity of botulinum toxin, according to one example of the present invention.

FIGS. 26a and 26b show the results of optimizing capture antibody treatment in a method of determining the activity of botulinum toxin, according to one example of the present invention.

FIGS. 27a and 27b show the results of optimizing detection antibody treatment in a method of determining the activity of botulinum toxin, according to one example of the present invention.

FIG. 28 shows the results of optimizing a method of detecting the activity of HRP conjugates in a method of determining the activity of botulinum toxin, according to one example of the present invention.

FIG. 29 is a schematic view showing a sandwich ELISA method for determining the activity of botulinum toxin according to one example of the present invention.

FIGS. 30a to 30c show the results of examining the accuracy and linearity of a sandwich ELISA method for determining the activity of botulinum toxin, according to one example of the present invention.

FIGS. 31a to 31c show the results of measuring biopotency by a sandwich ELISA method for determining the activity of botulinum toxin, according to one example of the present invention.

MODE FOR INVENTION

Hereinafter, the present invention will be described in further detail with reference to examples. It will be obvious to those skilled in the art that these examples are for illustrative purposes only and are not intended to limit the scope of the present invention.

Materials and Method 1. Reagents for Cell Development 0.25% trypsin EDTA (GIBCO™ 25200056), 12-well plate (Corning CLS3513), 24-well plate (Falcon 353047), 6-well plate (Falcon 353046), antibiotic antimycotic solution (AA) (100×) (Sigma A5955), boric acid (Sigma B6768), collagen from human placenta (Sigma C5533), DMSO (Sigma D2650), DPBS (Welgene LB001-02), DTT (Sigma D0632), fetal bovine serum (FBS) (YI Frontier US-FBS-500), gelatin solution (Sigma G1393), GlutaMAX™ (GIBCO™ 35050061), glycerol (Affymatrix USB 16374), MEM (GIBCO™ 11095080), MEM non-essential amino acid (NEAA) (100×) (GIBCO™ 11140050), PCR *Mycoplasma* Detection Set (Takara Bio 6601), poly-D-lysine hydrobromide (Sigma P6407), polysorbate (Sigma P7949), RIPA buffer (10×) (abcam ab156034), sodium pyruvate (GIBCO™ 11360070), sodium tetraborate (Sigma 221732), T75 flask (Falcon BD353136), TAKARA EX TAQ™ (Takara Bio RR001), TRYPLE™ Express Enzyme (1×) (GIBCO™ 12604021).

Materials and Method 2. Preparation of Botulinum Toxin a Stock Solution, Diluent, and BoNT/A Toxic Medium Purified botulinum toxin serotype A(BoNT/A) was provided by Hugel (EXBII1501).

Materials and Method 2-1. Preparation of BoNT/A Working Stock Solution

Purified BoNT/A was provided by Hugel (EXBII1501). BoNT/A was diluted to make working stock solution (10 nM) using a toxin dilution buffer consisting of 50 mM sodium phosphate, pH 7.0, 1 mM DTT, 0.05% polysorbate, 20% glycerol, and 0.2 mg/ml of acetylated-BSA. BoNT/A working stocks were stored in aliquots at −80° C. prior to use. And BoNT/A stock solution was prepared as follows.

(1) Master Stock (200 U/ml): Re-suspend the lyophilized BoNT/A (200 U) in 1 ml of intoxication medium or saline solution, and leave it at RT for 10 min.

(2) Stock A (50 U/ml): Aliquot 150 μl of the master stock in a sterile microfuge tube with 450 μl of intoxication medium at RT (i.e., 1:4 dilution of master stock).

(3) Stock B (5 U/ml): Aliquot 20 μl of the stock A in a sterile microfuge tube with 180 μl of intoxication medium at RT (i.e., 1:10 dilution of stock A).

(4) Stock C (0.5 U/ml): Aliquot 20 μl of the stock B in a tube containing 180 μl of intoxication medium at RT (1:10 dilution of stock B).

Materials and Method 2-2. Sample Preparation for Standard Curve

BoNT/A Standard Reference Samples for Standard Curve prepared as follows.

1. Standard Stock A (50 pM, 113.6 U/ml): Re-suspend the lyophilized BoNT/A (100 U) in 880 μl of intoxication medium or saline solution, and leave it at RT for 10 min.

2. Standard Stock B (10 pM, 22.7 U/ml): Aliquot 50 μl of Stock A in a sterile microfuge tube with 200 μl of intoxication medium at RT (i.e., 1:5 dilution of Stock A).

3. Standard Stock C (2 pM, 4.54 U/ml): Aliquot 50 μl of Stock B in a sterile microfuge tube with 200 μl of intoxication medium at RT (i.e., 1:5 dilution of Stock B).

Materials and Method 3. Plate Coating for Neuronal Cell Culture

Culture plate was coated overnight with either gelatin solution (0.1% in 1×PBS), collagen Type IV (0.1 mg/ml), or poly-D-lysine (PDL) (50 μg/ml). Freeze-dried collagen was reconstituted in deionized $H_2O$ to a final concentration of 0.1 mg/ml. PDL solution was prepared by dissolving 5 mg powder in 0.1 M borate buffer, pH 8.5, to the working concentration of 50 μg/ml. Culture plate was rinsed twice with 1×DPBS and air-dried in the tissue culture hood.

Materials and Method 4. Propagation of Cell Lines and Culture Medium

Thirteen neuronal cell lines were collected from 5 different institutes (Table 1). Neuronal cells were purchased from the American Tissue Culture Collection (ATCC), Deutsche Sammlung von Mikroorganismen and Zellkulturen (DSMZ), Japanese Collection of Research Bioresources (JCRB), Korean Collection for Type Culture (KCTC), and Korean Cell Line Bank (KCLB). They were maintained and propagated in the recommended medium. Mycoplasm contamination of all cell lines were monitored using PCR *Mycoplasma* Detection Set (Takara Bio Inc. 6601) at every 4 passages of N2-42F cells or 10 passages of SiMa and hybridoma cells. The PCR test was performed according to the recommended procedure. In brief, culture supernatant was collected and incubated for 3-4 days. PCR (50 µl) was performed with aliquots (3 µl) of culture supernatant, 1×PCR buffer, dNTP mixture, MCGp F1/R2 primers, and TAKARA EX TAQ™ (Takara Bio RR001). Aliquots (10 µl) of PCR products were resolved on a 1% agarose gel and visualized by ethidium staining.

TABLE 1

| Cell line | Source | Culture Medium |
|---|---|---|
| SK-N-SH | KCLB 30011[1] | MEM, 300 mg/L glutamine, 25 mM HEPES, 25 mM NaHCO$_3$, 10% FBS |
| SH-SY5Y | KCLB 22266[1] | MEM, 20 mM HEPES, 25 mM NaHCO$_3$, 10% FBS |
| IMR-32 | KCLB 10127[1] | RPMI1640, 300 mg/L glutamine, 25 mM HEPES, 25 mM NaHCO$_3$, 10% FBS |
| Neuro-2a | KCTC AC28106[2] | MEM, 10% FBS |
| SK-N-MC | KCTCHC18501[2] | DMEM, 10% FBS |
| N1E-115 | ATCCCRL2263[3] | DMEM, 10% FBS |
| NG108-15 | ATCC HB12317[3] | DMEM, 0.1 mM hypoxanthin, 0.4 mM aminopterin, 16 mM thymidine, 10% FBS, 1.5 g/L NaHCO$_3$ |
| BE(2)-M17 | ATCC CRL2267[3] | EMEM + F12, 10% FBS |
| SiMa | DSMZ ACC164[4] | RPMI1640, 2 mM glutamine, 10% FBS |
| KP-N-RT-BM-1 | JCRB IFO50432[5] | RPMI1640, 10% FBS |
| KP-N-YN | JCRBIFO50431[5] | RPMI1640, 10% FBS |
| NH-6 | JCRB 0832[5] | Alpha-MEM, 10% FCS |
| NH-12 | JCRB 0833[5] | Alpha-MEM, 10% FCS |
| TGW | JCRB 0618[5] | EMEM, 10% FBS |

[1]KCLB; Korean Cell Line Bank
[2]KCTC; Korean Collection for Type Culture
[3]ATCC; American Tissue Culture Collection
[4]DSMZ; Deutsche Sammlung von Mikroorganismen und Zellkulturen
[5]JCRB; Japanese Collection of Research Bioresources
FBS; fetal bovine serum,
FCS; fetal calf serum Materials and Method 5: Reagents for Antibodies Development 2-mercaptoethanol (Sigma M3148), 4-iodopheylboronic acid (Sigma 471933), 10×TBS (BIO-RAD 170-6435), 10× Tris/Glycine/SDS buffer (Bio-Rad 161-0772), 12% Mini-PROTEAN® TGX™ (Bio-Rad 456-1046), acetic acid (Merck 100063), alkaline phosphatase (Sigma P0114), AMICON Ultra-15, Ultracel 30K (Millipore UFC903024), antibiotic antimycotic solution (AA) (100×) (Sigma A5955), bromophenol blue (Sigma B0126), DMEM (Gibco™ 11995065), DMSO (Sigma D2650), DMSO (Sigma 472301), EZ-link NHS-PEG$_4$-Biotin (Thermo Fisher Scientific 21329), ethylene glycol (Sigma 324558) fetal bovine serum (FBS) (YI Frontier US-FBS-500), glycerol (Affymetrix USB 16374), glycine (Bioshop GLN001), glutaraldehyde solution (Sigma G7651), horseradish peroxidase (Sigma P6782), hydrogen peroxide solution (Sigma 216763), LUMINOL (Sigma 123072), magnesium chloride (Sigma M8266), MEM non-essential amino acid (NEAA) (100×) (GIBCO™ 11140050), methanol (Merck 106009), PCR® STRIP TUBE (Axygen PCR-0208-CP-C), polyvinylidene fluoride (PVDF) membrane (Millipore ISEQ00010), potassium chloride (Sigma P9333), PRECISION PLUS PROTEIN™ dual color standards (Bio-Rad 1610374) SDS solution 20% (w/v) (Bio-Rad 161-0418), skim milk (BD DIFCO™ 232-100), sodium acetate (Sigma W302406), sodium bicarbonate (Sigma S6014), sodium borohydride (Sigma 452882), sodium chloride (Merck 106404), sodium (meta)periodate (Sigma S1878), sodium phosphate dibasic (Sigma S7907), sodium phosphate monobasic (Sigma S5011), sodium stannate trihydrate (Sigma 336262), tetrabutylammonium borohydride (Sigma, 230170), T175 (SPL 74175), T75 flask (SPL 70375), Tris (Bioshop TRS001), zinc chloride (Sigma 229997).

Materials and Method 6: Setting of Antibody Manufacturing Method

Materials and Method 6-1. Generation of Polyclonal and Monoclonal Antibodies Using Synthetic Peptides Synthetic peptides were conjugated with keyhole limpet hemocyanin (KHL) at either C- or N-terminus, as summarized in FIG. 8. Firstly, two rabbits were immunized with peptide antigens to produce polyclonal serum. After initial injection, the rabbits were boosted periodically for 6 weeks. Rabbit sera were tested for their reactivity and specificity by Western blot analysis and ELISA. They were then stored at −80° C. before use. Secondly, to generate monoclonal antibody, four mice were injected with peptide antigens. Antibody-producing splenocytes were then collected and fused with myeloma cells to form hybridomas, followed by three rounds of the single-cell clonal selection, as shown in FIG. 9. In brief, hybridomas were screened initially by ELISA using peptide antigens, then by Western blot analysis with either recombinant SNAP25 proteins (GST-SNAP25$_{FL}$ and GST-SNAP25$_{197}$) or total cell lysates derived from neuronal cells (SiMa), and finally by sandwich ELISA with total cell lysates. Antibody-producing hybridomas were expanded and stored at the vapor phase of liquid nitrogen until they were recovered for antibody production, as detailed below.

Materials and Method 6-2. Preparation of SNAP25-Affinity Column

Recombinant SNAP25$_{197}$ was concentrated to 10 mg/ml using AMICON Ultra-15 by repeated centrifugation at 1,000×g for 10 min at 4° C., while measuring the protein concentration using the Nano spectrophotometer (Drawell Scientific Instrument Co., Ltd, Shanghai). Aliquot (3 ml) of SNAP25$_{197}$ in AMICO Ultra-15 was mixed with 12 ml of coupling buffer (0.1 M HEPES, pH 7.5, 0.1 M NaCl) and re-concentrated by centrifugation at 1,000×g. This buffer exchange was repeated 6 times, and SANP25$_{197}$ concentrate was added to 1 ml slurry of Affi-Gel 15 (Bio-Rad) in deionized H$_2$O. After incubation on a shaker incubator for 1 hr at RT, the Affi-Gel 15 was centrifuged at 1,000×g for 10 min at 4° C. This SNAP25$_{197}$-conjugated Affi-Gel 15 (SNAP25-AffiGel) was re-suspended in 10 ml of 10 mM ethanolamine hydrochloride, pH 8.0 and incubated for 1 hr at RT. After washing with 1×PBS, SNAP25-AffiGel was stored in 1×PBS containing 0.2% sodium azide before use.

Materials and Method 6-3. Purification of Polyclonal Antibody

Rabbit serum was diluted 10 times with 10 mM Tris-HCl, pH 7.5, and centrifuged at 10,000× g for 10 min at 4° C. After filtering through 0.45 µm bottle top filter (NALGENE™), the clear serum diluent was passed through SNAP25-AffiGel three times. SNAP25-AffiGel was then washed with 20 CV of 10 mM Tris-HCl, pH 7.5, and 0.5 M NaCl, and bound proteins were sequentially eluted with 12 CV of 0.1 M sodium acetate, pH 5.5, 0.1 M glycine, pH 4.0, and 0.1 M glycine, pH 2.5 and 0.1 M triethylamine, pH 11.5. During elution, protein samples were collected in tubes containing 0.1 ml of 1 M Tris-HCl, pH 8.0. Protein-containing peak fractions were pooled and concentrated to 1 ml using AMICON Ultra-15. After dialysis with four changes of 1×PBS and 10% glycerol (0.5 L) at every 90 min, they were analyzed by SDS-PAGE and ELISA.

Materials and Method 6-4. Antibody Conjugation with Horseradish Peroxidase (HRP)

For conjugation of HRP, purified B4 or C16 IgG was concentrated to 10 mg/ml using AMICON Ultra-15 through repeated centrifugations at 1,000×g for ~15 min per centrifugation at 4° C., while providing with excessive volume of the conjugation buffer (0.1 M $NaHCO_3$, pH 9.5, 0.9% NaCl) at the end of each centrifugation. HRP (5 mg) was solubilized in 1.2 ml of deionized $H_2O$ and mixed with 0.3 ml of 0.1 M sodium periodate in 10 mM sodium phosphate, pH 7.0. After incubation for 20 min at RT, the HRP solution was dialyzed with four changes of 1 mM sodium acetate, pH 4.0, for 6 hr at 4° C. Concentrated antibody (5 mg) and activated HRP (5 mg) were mixed together in a microfuge tube and incubated for 2 hr at RT with light protection. The conjugation reaction was stopped by the addition of 0.1 ml of sodium borohydride (4 mg/ml in deionized $H_2O$). The HRP-antibody conjugate was dialyzed using Pur-A-Lyzer Maxi 50000 with three changes of 1×PBS and once with 1×PBS/50% glycerol at an hourly interval at 4° C. The HRP-antibody conjugate was stored at 4° C. or −80° C. for a long-term storage before use.

Materials and Method 6-5. Antibody Conjugation with Activated Biotin

A15 IgG (1 mg/ml) was transferred to Pur-A-Lyzer Maxi 20000 and dialyzed with four changes of a reaction buffer consisting of 0.1 M phosphate, pH 7.2, and 0.15 M NaCl at an hourly interval at 4° C. with light protection. Activated biotin (10 mM in the reaction buffer) (EZ-Link NHS-$PEG_4$-Biotin) was mixed with 50 µg aliquot of A15 IgG to the final concentration of 0.1 mM, 0.25 mM, or 0.5 mM. The mixture was adjusted to 100 µl with the reaction buffer and incubated for 2 hr at 4° C. with light protection. After adding 2 µl of 0.1 M glycine, the reaction mixture was dialyzed with three changes of 1×PBS and once with 1×PBS/50% glycerol at an hourly interval at 4° C. and stored in a microfuge tube at −20° C. before use. The extent of biotinylation of IgG was estimated using the Pierce Biotin Quantitation Kit (Thermo Scientific 28005) and the reactivity and specificity of biotinylated IgG were examined by sandwich ELISA.

Materials and Method 6-6. Crosslinking of AP to Antibodies

Conjugation of alkaline phosphatase (AP) to antibody was initiated by adding glutaraldehyde to 0.25% in a mixture (20 µℓ) consisting of reaction buffer (0.1 M sodium phosphate, pH 6.8), 50 µg of AP (2.2 mg/ml) (Sigma-Aldrich P0114-10KU), and 100 µg of purified IgG such as monoclonal antibody A15, polyclonal antibody rA15 IgG, and polyclonal anti-SNAP25 IgG (Sigma-Aldrich S9684). After incubation on ice for 1 hr with light protection, the reaction was provided with 1 µℓ aliquot of 1 M ethanolamine and incubated for 1 hr at RT with light protection. AP-IgG conjugate was dialyzed with three changes of 1×PBS and once with a storage buffer (25 mM Tris-HCl, pH 7.5, 1 mM $MgCl_2$, 0.1 mM $ZnCl_2$, and 50% glycerol) at an hourly interval at 4° C. Antigen binding specificity and AP activity of AP-IgG conjugate was examined by direct ELISA, described below.

Materials and Method 6-7. Measurement of Ku by OCTET RED96

For kinetics analysis of monoclonal antibody, the Bio-Layer Interferometry (BLI) assay was performed at 30° C. using FORTÉBIo® Octet Red96 instrument, following the procedure recommended by the manufacturer. In brief, recombinant GST-SNAP25$_{FL}$ or SNAP25$_{197}$ was diluted to 125 or 250 nM in 1× kinetics buffer (1× KB)/1×PBS, and the analyte, i.e. purified IgG, was serially diluted to 3.9, 7.8, 15.6, 31.25, 62.5, 125, 250 nM in 1× kinetics buffer. After equilibration in 1× kinetics buffer for 1 min, anti-GST probes (FORTÉBIO 18-5096) were loaded with GST-SANP25$_{FL}$ or GST-SNAP25$_{197}$ for 30 min, followed by dipping in 1× kinetics buffer for 10 min. Subsequent to association and dissociation of analyte for 10 min each, kinetics curves were obtained, and $K_D$ (equilibrium dissociation constant) was estimated using FortéBio® Octet analysis software.

As an alternative kinetics analysis, anti-mouse IgG Fc capture (AMC) biosensors were loaded with antibody and subjected to association/dissociation with serially diluted GST-SNAP25. In brief, purified IgG was diluted to 100 or 200 nM, whereas GST-SNAP25$_{FL}$ or SNAP25$_{197}$ was serially diluted to 1.56, 3.125, 6.25, 12.5, 25, 50, and 100 nM. After equilibration in 1× kinetics buffer for 1 min, AMC biosensors were loaded with IgGs for 10 min, followed by dipping in 1× kinetics buffer for 10 min. Association and dissociation of analyte were carried out for 10 min each, and $K_D$ was estimated as described above.

Materials and Method 6-8. Direct ELISA

Immunoplate (Thermo Fisher Scientific A71125) were coated for 2 hr at 37° C. with 1 µg of GST-SNAP25$_{FL}$ or GST-SNAP25$_{197}$ in 0.1 M carbonate buffer, pH 9.5. After washing with 1×PBS, immunoplate was incubated with 300 µl of a blocking buffer (5% nonfat dried milk in 1×PBS) for 15 min at RT. After washing three times with 1×PBST (1×PBS/0.05% Tween-20), the microplate was provided with 100 µl of hybridoma culture supernatant (1:20-10,000 dilution) or ascites fluid (1:1,000-312,500 dilution) and incubated for 1 hr at RT. The microplate was washed three times with 1×PBST, to which aliquots (100 µl per well) of goat anti-mouse IgG-HRP conjugate (1:1,000 dilution) (Ab Frontier LF-SA8001) were added. After incubation for 1 hr at RT, the microplate was washed three times with 1×PBST and HRP reaction was carried out with 50 µL of 1-STEP™ Ultra TMB-ELISA (Thermo Fisher Scientific 34028) at RT for 3-25 min. HRP reaction was stopped by the addition of 50 µL of 1 M H2504 and the ELISA signal was estimated at 450 nm using BIO-TEK SynergyNeo2.

Materials and Method 6-9. Western Blot Analysis

Recombinant GST-SNAP25 (20 ng-1 µg Per Well) or Total Cell Lysate of Neuro-2a Cells (15 µg per well) were resolved together with Precision protein standards (3 µl per well) by 10% or 12% SDS-PAGE. After 5 min-soaking in a transfer buffer consisting of 48 mM Tris, 38.9 mM glycine, 20% methanol, 0.05% SDS, proteins were transferred to PVDF membrane using TRANS-BLOT® Semi-Dry (Bio-Rad 170-3940) for 45 min at 25 V PVDF membrane was briefly rinsed with 1×TBST (1× TBS/0.05% TWEEN 20) and incubated with a blocking buffer (5% nonfat dried milk in 1×TBST) for 15 min at RT. Subsequently, PVDF membrane was incubated with either hybridoma culture supernatant (1:100 dilution in blocking solution) for 45 min at RT. Polyclonal anti-SNAP25 IgG (Sigma 59684) (1:8,000 dilution) and anti-SNAP25$_{197}$ IgG (R&D MC6050) (1:100 dilution) were used as positive controls. After washing with 1×TBST three times for 15 min, PVDF membrane was incubated with either goat anti-rabbit IgG-HRP conjugate (1:10,000 dilution) or goat anti-mouse IgG-HRP conjugate (1:10,000 dilution) for 45 min at RT. After washing 3 times with 1×TBST, recombinant GST-SNAP25 or endogenous SNAP25 was detected and quantified using ECL solution (see below) and Bio-Rad CHEMIDOC™ MP Imaging system (Bio-Rad Universal hood III).

EXAMPLES

Example 1: Screening of BoNT/A-Sensitive Neuronal Cell

Example 1-1. Comparative Analysis of Neuronal Cell Lines for their Sensitivity to BoNT/A Neuronal cells were seeded at 2×10$^5$ cells/well in a 24-well plate and 24 hr later, they were treated with 2 nM BoNT/A in medium indicated in Table 1 for 3 days. Total cell lysates (TCLs) were prepared using 1×RIPA, and aliquots (3.5 μg) were subjected to 12% SDS-PAGE.

$SNAP25_{FL}$ and $SNAP25_{197}$ were analyzed by Western blot using rabbit polyclonal IgG (Sigma S9684), specific for SNAP25, as described in Materials and Methods. ECL solution was formulated and optimized by AbBio Inc. Working ECL solution was prepared by mixing Sol A and Sol B in 1:1 ratio before use. Sol A and Sol B is comprised as Table 2. And sensitivity of cell lines to BoNT/A (2 nM) were represented in Table 3.

TABLE 2

| ECL solution | Composition |
|---|---|
| SolA | 0.1M Tris-HCl, pH 8.8, 2.5 mM LUMINOL in DMSO, 4 mM 4-iodopheylboronic acid, 0.2 mM tetrabutylammonium borohydride, 2% ethylene glycol, and 0.02% TRITON X-100. |
| SolB | 0.1M Tris-HCl, pH 8.8, 10.6 mM hydrogen peroxide, and 0.012% sodium stannate |

TABLE 3

| Cell line | Sensitivity to BoNT/A (2 nM) |
|---|---|
| SK-N-SH | No |
| SH-SY5Y | No |
| IMR-32 | No |
| Neuro-2a | Yes |
| SK-N-MC | No |
| N1E-115 | No |
| NG108-15 | No |
| BE(2)-M17 | No |
| SiMa | Yes |
| KP-N-RT-BM-1 | Yes |
| KP-N-YN | No |
| NH-6 | No |
| NH-12 | No |
| TGW | No |

As summarized in Table 3, except for SiMa cell, only neuro-2a and KP-N-RT-BM1 (K-BM1) cells yielded detectable levels of SNAP25 cleavage.

Example 1-2. Screening of BoNT/A-Sensitive Neuronal Cell

Neuro-2a, SiMa and KP-N-RT-BM-1 cells were separately cultured on a 24-well plate under the same conditions as materials and method, and the cleavage phenomenon of SNAP25 protein was analyzed by Western blot analysis The results are shown in FIG. 1. The extents of SNAP25 cleavage were estimated about 33%, 66%, and 29% for neuro-2a, SiMa, and K-BM1 cells, respectively.

Neuro-2a was further used for clonal selection over K-BM1 for the following reason. Firstly, the in vivo potency of BoNT/A, which is conventionally measured by mouse lethality (i.e. mouse $LD_{50}$), could be better recapitulated with mouse cell line. In fact, neuro-2a is a mouse cell line, but K-BM1 is a human cell line. Secondly, K-BM1 tends to grow at a much slower rate than neuro-2a (data not shown). It should be noted that the population doubling time of SiMa cells, a human neuroblastoma cell line, is reported to be 34 to 100 hrs (DSMZ ACC-164). Thirdly, neuro-2a cells appear to be a mixed population of several cell types under the microscope. Thus, it is likely that BoNT/A-sensitive cells exist in the heterogeneous neuro-2a cell population.

Example 2: Clone Selection for BoNT/A-Sensitive Neuronal Cell

Among the Neuro-2a cell populations selected in Example 1, clones highly sensitive to BoNT/A were selected.

Example 2-1. Clonal Culture of Neuro-2a Cells

Neuro-2a cells were propagated in MEM supplemented with 10% fetal bovine serum (FBS), 1× non-essential amino acids (1×NEAA), 1× sodium pyruvate, 1× GLUTAMAX™, and 1× antibiotic antimycotic (1× AA). When cells reached ~80-90% confluence, they were treated with 1× TrypLE (GIBCO™ 12604021) to make a single cell suspension. After determining the viable cell number using the hemocytometer and trypan blue, cells were diluted to the density of 10 cells per ml of medium. Then, 100 μl aliquots (~one cell equivalent) were added to 7×96-well culture plate. Colony growth was periodically monitored by microscopic examination. At ~60% confluence, cells were transferred to a 24-well culture plate. Later, they were equally divided, and one half was stored in the liquid nitrogen tank, and the rest was tested for the sensitivity to BoNT/A intoxication.

Neuro-2a clonal cells were sub-cultured from the 24-well plate to 96-well microplate. On the following day, culture medium was replaced with PRMI1640 supplemented with 2 mM L-alanyl-L-glutamine, 1× B27, 1× N2, 1×NEAA (differentiation medium) for 2 days to induce neuronal differentiation. On the $4^{th}$ day, GT1b was added to the final concentration of 25 μg/ml (1× intoxication medium). After incubation for 24 hr, the culture medium was replaced with the intoxication medium containing BoNT/A (0.1 nM), and cells were incubated for additional 2 days. After removing medium by aspiration, cells were treated with 1×SDS sample buffer, and aliquots were examined for the extent of SNAP25 cleavage by 12% SDS-PAGE and Western blot analysis. This clone selection procedure was repeated three times, and the results confirmed in each clone selection procedure are shown in FIG. 2. Following the procedure optimized for SiMa cells by Allergan with minor modifications as described in Materials and Methods (PLoS One. 2012; 7(11):e49516.), 142 clonal cells, plated from 24-well plates to 96-well culture plates, were tested for the sensitivity to BoNT/A. As shown in FIG. 2, a total of 19 positive clones were identified that exhibited noticeably higher sensitivities to BoNT/A than parental neuro-2a. Of positive clones subjected to multiple rounds of a single-cell clonal selection, only clone 42 persistently displayed higher BoNT/A sensitivity than parental neuro-2a. After three rounds of a single-cell clonal selection, clone 42 was renamed as N2-42F following the nomenclature recommended for cell lines (Cell Stem Cell. 2011 Jun. 3; 8(6): 607-8.; Bioinformatics. 2008 Dec. 1; 24(23):2760-6).

Example 2-2. Recovery, Proliferation, and Storage of Freezed Cells

Recovery of freezed cells was performed as follows.
(1) Rapidly thaw (<2 minute) the cell stock vial, retrieved from a liquid nitrogen freezer, by gentle agitation in a 37° C. water bath.
(2) Once thawed, decontaminate the cell stock vial by spraying with 70% ethanol.
(3) Unscrew the top of the vial in a laminar flow tissue culture hood, and transfer the content to a sterile 15-ml conical tube containing 9 ml of pre-warmed complete medium.
(4) After gentle centrifugation (125×g for 10 min), remove the supernatant by aspiration and re-suspend the cells in 2 ml of the complete medium.
(5) Pipet gently to loosen the pellet and break apart clumps, and transfer the cell suspension to T75 flask containing 25 ml of the complete medium.
(6) Incubate the flask at 37° C. in a $CO_2$ incubator.

Cell culture was performed as follows.
(1) When cells become ~90% confluent, remove the culture medium by aspiration and rinse the culture flask once with 1×DPBS.
(2) Add 1 ml of 0.25% trypsin-EDTA and incubate the flask for 10 min at 37° C.
(3) Add 9 ml of the complete medium, and break apart cell clumps by repeated pipetting.
(4) Transfer the cell suspension to a 15 ml-conical tube, and centrifuge it at 800×g for 5 min.
(5) Discard the supernatant by aspiration and re-suspend the cell pellet with 10 ml of the complete medium.
(6) Determine the density of viable cells using the hemocytometer.
(7) Transfer 3 ml aliquots of the cell suspension to fresh T75 flasks.
(8) Incubate for 3 days until cells reach ~90% confluency.

Cell freezing for establish cell bank was performed as follows.
(1) Subculture ~90% confluent cells in two T75 flasks to eight T75 flasks.
(2) When cells reach a late growth phase (~2.0×107 cells/flask), remove the culture medium and prepare a single-cell suspension through treatment with 0.25% trypsin-EDTA.
(3) Re-suspend the cell pellet at a density of 5×106 cells/ml with a freezing medium.
(4) Aliquot 1 ml of cell suspension into cryogenic stock vials.
(5) Place tubes in the isopropanol-filled freezing container (be sure to tighten the tube cap).
(6) Transfer the freezing container to −80° C. overnight.
(7) On the following day, transfer frozen cells immediately to the liquid nitrogen vapor phase storage.

Example 3: Identification of N2-42F Characteristics and Culture Environment

Example 3-1. Confirmation of Doubling Time of N2-42F

The cleavage times of Neuro-2a cells and N2-42F, which were confirmed to be capable of detecting truncated forms of the SNAP25 protein, were determined.

N2-42F and neuro-2a cells were seeded at $1.5\times10^5$ cells per well in a 6-well culture plate. On a daily basis for 6 days, total viable cells were counted using the hemocytometer and trypan blue staining. Doubling time was calculated using viable cell numbers obtained during the exponential growth phase as follows Table 4. And the results are shown in Table 5 and FIG. 3. T is incubation time, Xb and Xe are the cell number at the beginning and at the end of incubation time in Table 4, respectively.

TABLE 4

| |
|---|
| Doubling time = T × ln2/ln(Xe/Xb) |

TABLE 5

| Cell line | Doubling time (hr) |
|---|---|
| Neuro-2a | 24 ± 4.7 |
| N2-42F | 24 ± 2.9 |

As shown in Table 5 and FIG. 3, the cleavage time was 24±4.7 hours for Neuro-2a and 24±2.9 hours for N2-42F.

Example 3-2. Confirmation of Morphology of N2-42F

Allergan reported the isolation of BoNT/A-sensitive clone (H1) from SiMa cells (PLoS One. 2012; 7(11): e49516.). Thus, it is expected that like neuro-2a, SiMa cells also represent a heterogeneous cell population of mixed cell types but their sub-clones such as H1 and N2-42F are homogeneous cell types. This was confirmed by microscopic examination of neuro-2a, N2-42F, and SiMa cells. As shown in FIG. 4, both neuro-2a and SiMa exhibit heterogeneous morphologies under the microscope but N2-42F cells look highly homogeneous.

From the above results, it can be seen that N2-42F corresponds to a homogeneous cell type as a single clone among various clones constituting Neuro-2a.

Example 3-3. Confirmation of Culture Conditions of N2-42F

In efforts to optimize the BoNT/A intoxication condition, N2-42F cells were grown in culture plates coated with different matrices. Unlike parental neuro-2a cells that are routinely propagated in non-coated culture plates, N2-42F cells exhibit a clear preference for culture plates coated with poly-D-lysine (PDL) (FIG. 5). Neither non-coated plates nor the ones coated with collagen type IV or gelatin supported efficient growth of N2-42F cells. On those plates, N2-42F looked unhealthy, forming clumps. Also, they were loosely attached to the plate. By contrast, N2-42F cells were grown on PDL-coated plates, firmly attached yet evenly distributed. Thus, unless otherwise indicated, PDL-coated culture plates were exclusively used for N2-42F cells in the present research.

Example 4: Confirmation of the Susceptibility of N2-42F to Botulinum Neurotoxins Using SiMa cells as control, the BoNT/A sensitivity of N2-42F cells was thoroughly examined in triplicate sets of 96-well plate culture provided with 1× intoxication medium containing varying concentrations of BoNT/A. After incubation for 4 days, cells were treated with 50 μl of 1×SDS sample buffer, and aliquots (12 μl) were subjected to Western blot analysis using polyclonal anti-SNAP25 IgGs (Sigma S9684), as described in Materials and Methods. Endogenous SNAP25 cleavage was insignificantly detected in both SiMa and N2-42F cells treated with 0.93 pM or lower concentrations of BoNT/A. Treatment with 2.78-25 pM BoNT/A led to 25-72% cleavage of SNAP25 in N2-42F cells and 33-75% with SiMa cells (FIG. 6a). This result indicates that N2-42F cells are as sensitive as SiMa cells.

Including BoNT/A, there are seven serologically different botulinum neurotoxins from BoNT/A to BoNT/G. Similar to BoNT/A, BoNT/B has also been licensed for the pharmaceutical application such as MYOBLOC® or NEUROBLOC®. Thus, it was explored if N2-42F cells can be used in any cell-based potency assays for different serotypes of botulinum neurotoxins. For this purpose, differentiating N2-42F and Neuro-2a cells were compared for their susceptibility to different neurotoxin complexes (Metabiologics C08RA188-RA194).

As shown in FIG. 6b, 25 pM of Metabiologics BoNT/A (M-BoNT/A) gave rise to a saturating extent of SNAP25 cleavage in N2-42F. Under the same condition, about 44% of SNAP25 cleavage was observed in Neuro-2a cells. The higher sensitivity of N2-42F cells to M-BoNT/A is consistent with its sensitivity to BoNT/A, prepared by HUGEL (i.e. Botulax). N2-42F cells also exhibited significantly a higher sensitivity to M-BoNT/B. Intoxication with 2 nM of M-BoNT/B resulted in near complete cleavage of Vamp2 in N2-42F cells but only about 50% cleavage in Neuro-2a. Though to lesser extents, N2-42F cells exhibited higher sensitivities to M-BoNT/C and M-BoNT/F. But with M-BoNT/D (5 pM or 200 pM), there was no noticeable difference in their sensitivity between N2-42F and Neuro-2a cells (data not shown). Nor they showed any detectable level of sensitivity to M-BoNT/E (10-400 pM) or BoNT/G (50-2000 pM). Our results indicate that N2-42F cells can be used as host in the cell-based potency assay for BoNT/A, BoNT/B, BoNT/C, and BoNT/F.

Example 5: Confirmation of Stability of N2-42F

Passage stability could a key feature of neuronal cells to be used as host in any cell-based assay platforms. N2-42F cells were continuously propagated for multiple passages. The cells in early passages were used to make the master cell bank as described in Materials and Methods. And at every 5 passages, cells were also stored in the liquid nitrogen tanks for the passage stability. In brief, N2-42F cells stored at passage 5 (P5) and 15 (P15) were restored from the liquid nitrogen tank and at 90% confluence, they were compared in the BoNT/A sensitivity using the 1× intoxication medium containing 0.1 nM BoNT/A following the procedure described in FIG. 6. Experiment was performed in a triplicate set using SiMa cells as control. As shown in FIG. 7, 63-68% of SNAP25 cleavage was measured in N2-42 cells at P5 and 63-71% at P15. SiMa cells exhibited 70-77% cleavage.

This result indicates that similar to H1 clone of SiMa cells identified by Allergan, the BoNT/A sensitivity is a stably inheriting property of N2-42F cells. which makes them a suitable host, the second of its kind next to the H1 clone of SiMa cells, in a cell-based assay platform.

Example 6: Determination of BoNT/a Potency Based on N2-42F

Example 6-1. Experimental Method 96-well plates were coated in the manner described in Materials and methods. While air-drying the 96-well culture plate, prepare a total of 7 ml of N2-42F cell suspension in the density of $5.5 \times 10^5$ cells/ml. About 90% confluent N2-42F cells in one T75 flask would be sufficient for three 96-well culture plates. Transfer the cell suspension to a sterile buffer reservoir, and dispense aliquots (100 µl) of the cell suspension into each well using a multichannel pipette, and incubate the 96-well culture plate in a CO2 incubator. Outer wells of a 96-well plate should be filled with aliquots (100 µl) of 1× AA solution to avoid the dreaded edge effects.

On the day after the cells were dispensed, all cell culture medium was removed from the 96-well plate using a multichannel pipette, and 100 µl of RPMI 1640 was added to rinse. The BoNT/A intoxication medium was then treated to each 96-well plate and incubated for 4 days at 37° C., 5% $CO_2$. In addition, the capture antibody, B4 IgG, was prepared in an amount of 7 ml, which was then divided into 50 µℓ in ELISA plates and stored at 4° C. overnight.

For measurement, the BoNT/A intoxication medium was removed from the 96-well plate using a multi-channel pipette and each well was treated with 60 µl of a lysis buffer (pH 7.5, 20 mM HEPES, 1% TRITON-200 mM NaCl, 1 mM EGTA, and 5 mM EDTA, added with proteolysis inhibitor immediately before use), and incubated 4° C. for 20 minutes with shaking at a speed of 500 rpm. Thereafter, the dissolution buffer contained in each well was obtained, and centrifuged 4,000 rpm for 20 minutes at 4° C.

The ELISA plate was washed 3 times with the washing buffer, added with 300 µl aliquots of the blocking buffer to each well, incubated for 15 min at RT, and washed twice with the washing buffer after remove the blocking buffer.

50 µl aliquots of TCL was transferred from the 96-well culture plate to the ELISA plate coated with the capture antibody (B4), and the ELISA plate was incubated for 4 hr at 4° C. on a microplate shaker at 200 rpm. Finally, the plate washed 3 times with the wash buffer.

For detection of SNAP25 and $SNAP25_{197}$, detection antibodies were added to ELISA plate (50 µl per well), and the plate was incubated for 1 hr at RT on a Thermo shaker incubator (200 rpm). And the plate was rinsed three times with the wash buffer, 50 µl aliquots of 1-StepTMUltra TMB-ELISA was added to the plate, the HRP reaction was terminated by adding 2 M sulfuric acid (50 µl/well) after 5 min. The HRP reaction was measured at 450 nm. The value at A450 may represent the relative amount of $SNAP25_{197}$.

Example 6-2. Preparation of Standard Curve and Determination of the BoNT/a Potency Standard curve and BoNT/A Potency were tested in the following manner. Calculate the average A450 value of control wells where sandwich ELISA was carried out with no BoNT/A treatment (i.e. 0 pM). Subtract the average control A450 value from test A450 values, and calculate the normalized average test A450 value. And then, plot the normalized average A450 values on Y axis against BoNT/A potency on X axis using Prism 5.0 (GraphPad Software, La Jolla, Calif.). Analyze the plot by successively selecting "analyze", "nonlinear regression (curve fit)", and "sigmoidal dose-response", which will yield a EC50 value. Prepare the standard curve using the normalized A450 values of test wells treated with 0.1-0.93 pM BoNT/A Standard Reference (see Appendix 2, Section D). And use the standard curve equation with R2 value of 0.95 or higher to determine the BoNT/A potency of test samples.

Example 7: Generation of Monoclonal Antibodies Specific for SNAP25

Allergan used a 13-amino acid (AA) residue peptide N-CDSNKTRIDEANQ-C(SEQ ID NO: 91) to raise antibody. The peptide was designed to be identical to the C-terminal end of $SNAP25_{197}$ generated upon BoNT/A digestion. Since $SNAP25_{FL}$ also has the identical amino acid sequence in it, it would be reasonable to posit that the specificity of monoclonal antibodies recognizing SNAP25$_{197}$ is attributable to as yet unidentified feature of SNAP25$_{197}$ rather than its primary amino acid sequence. SNAP25 consists of 206 AA residues (FIG. 8). Through SNARE motifs, it forms a stable ternary complex with syntaxin 1A and synaptobrevin 2 (VAMP2). The less stable and non-functional ternary complex is formed with SNAP25$_{197}$, whereas the ternary complex fails to form at all with SNAP$_{180}$ (PeerJ. 2015 June 30;3:e1065). Their finding that the C-terminal 9 AAs of SNAP25 is essential for the in vivo function and formation of a stable ternary complex suggests that the cleavage at AA position 197 by BoNT/A induces as yet unidentified structural alteration, particularly at the C-terminus and the second SNARE domain. Thus, the postulated structural difference between SNAP25$_{FL}$ and SNAP25$_{197}$ makes it possible to produce monoclonal antibodies specific for SNAP25$_{197}$.

A total of 10 peptide antigens were designed to meet the following criteria (Table 6). First, alpha helical regions exhibiting relatively lower antigenicity were excluded. Second, peptide sequences are non-redundant and unique, the properties of which are essential to reduce cross reactivity of antibodies.

TABLE 6

| Immunogens/AA Position in SNAP25 | | SEQ ID NOs | AA Sequence |
|---|---|---|---|
| N peptide | 1-13 | SEQ ID NO: 1 | KLH-C-MAEDADMRNELEE |
| | 1-13 | SEQ ID NO: 2 | MAEDADMRNELEE-C-KLH |
| | 19-38 | SEQ ID NO: 3 | KLH-C-DQLADESLESTRRMLQLVEE |
| | 51-70 | SEQ ID NO: 4 | KLH-C-DEQGEQLERIEEGMDQINKD |
| M peptide | 122-136 | SEQ ID NO: 5 | KLH-C-DEREQMAISGGFIRR |
| C peptide | 170-184 | SEQ ID NO: 6 | KLH-C-EIDTQNRQIDRIMEK |
| | 180-194 | SEQ ID NO: 7 | KLH-C-RIMEKADSNKTRIDE |
| | 180-197 | SEQ ID NO: 8 | KLH-C-RIMEKADSNKTRIDEANQ |
| | 186-197 | SEQ ID NO: 9 | KLH-C-DSNKTRIDEANQ |
| | 189-201 | SEQ ID NO: 10 | KLH-C-KTRIDEANQPATK |

Of a total of 10 peptides described in Table 6, M and N peptides were used to generate monoclonal antibodies capable of detecting both $SNAP25_{FL}$ and $SNAP25_{197}$. With C peptides, it was anticipated to obtain three different monoclonal antibodies with the binding specificity toward (1) $SNAP25_{FL}$, (2) $SNAP25_{197}$, and (3) both $SNAP25_{FL}$ and $SNAP25_{197}$. Throughout our research, two commercially available antibodies were used as control in ELISA and Western blot analysis. They include rabbit polyclonal anti-SNAP25 IgGs (Sigma-Aldrich) and MC6050 (R&D). The former recognizes both $SNAP25_{FL}$ and $SNAP25_{197}$, but the latter is a monoclonal antibody specific for $SNAP25_{197}$.

Individual synthetic peptide was injected to two rabbits to raise polyclonal serum and 4 mice to raise monoclonal antibody, as described in Materials and Methods. In particular, the procedure to establish hybridoma cells producing monoclonal antibody was summarized in FIG. 9. In brief, four mice were immunized per peptide antigen to induce antibody production. After ELISA screening of mouse serum for antibody production, splenocytes were isolated from ELISA-positive mice and fused with SP2 myeloma cells. Subsequently hybridoma cells were seeded at a single cell density 96-well plate per peptide antigen. As summarized in FIG. 9, initial screening to obtain positive clones was performed employing direct ELISA using peptide antigen, which was followed by a more stringent screening utilizing recombinant SNAP25 and total cell lysate.

Figure 10A:
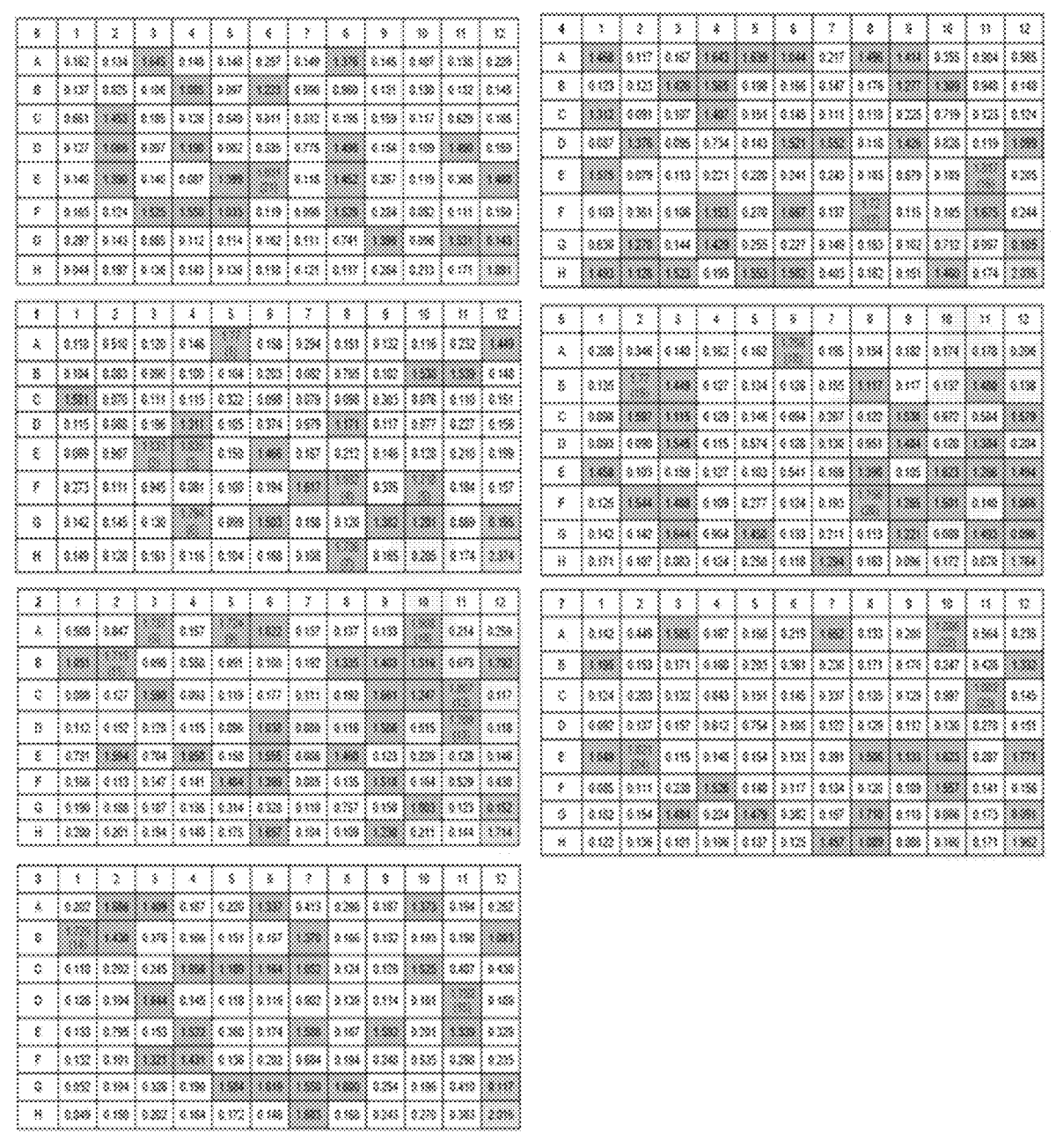

A representative result of initial hybridoma screening is shown in FIG. 10. Culture supernatants were collected from hybridoma cells (clone 4, B4) grown in 7×96-well plate and tested for their reactivity to peptide antigen by direct ELISA. About 25% clones yielded positive ELISA signals (panels A-G), and 24 relatively strong positives were selected and tested for their reactivity to endogenous SNAP25 by sandwich ELISA using total cell lysate (panel H). Ten clones selected for multiple rounds of single-cell clonal selections.

For the single-cell clonal selection, hybridoma clones were seeded at a single-cell density in one 96-well plate. Four days later, culture supernatants were tested for the reactivity to recombinant SNAP25 by direct ELISA, and five clones yielding relatively strong ELISA signals were selected for further analysis. For example, in case of clone 4, over 80% sub-clones, grown in a 96-well plate, were tested positive in direct ELISA (FIG. 11*a*). Twelve sub-clones produced ELISA signals lower than negative control, including A8-A10, B11, C10, D4, D8, D9, E5, E11, F10, and G7 (FIG. 11*a*). Five sub-clones were also analyzed by sandwich ELISA (FIG. 11*b*) and Western blot (FIG. 11*c*) using total cell lysate (TCL), as described in Materials and Methods. It should be noted that ELISA signals, with sub-clones of clone 4, were in a good agreement with the Western blot signals. Since TCL underwent denaturation during Western blot analysis, this result suggests that monoclonal antibody produced by hybridoma clone 4 equally reacts with both non-denatured (i.e. ELISA) and denatured SNAP25.

Single-cell clonal selection repeated two more rounds, as summarized in FIGS. 12 & 13. After the second round of selection, two clones 6 & 8 were dropped from further screening because all culture supernatants in 96-well plate failed to yield ELISA signals significantly higher than negative control. Through a series of single-cell clonal selection, a total of 12 hybridoma clones were obtained that produce monoclonal antibodies specific for $SNAP25_{FL}$, $SNAP25_{197}$, or both.

Example 8: Production and Purification of Monoclonal Antibodies

Hybridoma cells were expanded in T175 flasks and used to make master cell bank. For production of monoclonal antibody, hybridoma cells were recovered from the stock vial stored at the vapor phase of liquid nitrogen. When cells reached about 90% confluency, they were sub-cultured at 1:4-10 in multiple T175 flasks. After incubation for 3-4 days, cells were collected by centrifugation and re-suspended in serum-free medium at $1.0\times10^6$ cells/ml. After incubation for 4 days, culture supernatants were collected and used to purify IgG using protein G column (HITRAP® Protein G HP column), as described in Materials and Methods. Yield of monoclonal antibody purified using culture supernatants varied batch to batch of hybridoma culture and also for individual hybridoma clone. Over a dozen times of purification with different batches of culture supernatant (165-542 ml) yielded about 2.45-5.52 mg of C16 IgG (Table 7).

TABLE 7

| Monoclonal antibody | Volume of cell culture supernatant (ml) | Yield (mg) |
|---|---|---|
| C16 IgG$_1$ | 185 | 2.78 |
| | 235 | 4.32 |
| | 542 | 2.90 |
| | 331 | 2.45 |
| | 291 | 2.60 |
| | 233 | 5.52 |
| | 225 | 3.87 |
| | 253 | 3.55 |
| | 190 | 3.16 |
| | 165 | 3.35 |
| | 269 | 3.76 |
| | 283 | 3.92 |
| | 277 | 4.41 |
| | 299 | 4.13 |
| | 237 | 3.43 |

Purification of other monoclonal antibodies is summarized in Table 8.

TABLE 8

| Polyclonal antibody | Volume of cell culture supernatant (ml) | Yield (mg) |
|---|---|---|
| A15 IgG$_1$ | 403 | 6.37 |
| | 210 | 2.22 |
| | 202 | 4.20 |
| | 217 | 3.90 |
| | 171 | 3.45 |
| | 226 | 3.16 |
| | 233 | 5.52 |
| | 205 | 4.04 |
| | 200 | 3.63 |
| | 177 | 5.11 |
| B23 IgG$_1$ | 44.5 | 0.17 |
| | 186 | 1.14 |
| B20 IgG$_1$ | 45 | 0.58 |
| B16 IgG$_1$ | 44.5 | 0.39 |
| B4 IgG$_1$ | 42 | 1.34 |
| | 292 | 4.32 |
| | 282 | 6.42 |
| | 285 | 5.45 |
| | 275 | 3.40 |
| C7 IgG$_{2a}$ | 152 | 5.18 |
| | 161 | 3.30 |
| F14 IgG$_1$ | 263 | 2.56 |

On average, about 1-2 mg of IgG was obtained from 100 ml of culture supernatant. Though data not shown, the purity of IgGs and their antigen binding specificity were validated by SDS-PAGE and ELISA.

Example 9: Purification of Polyclonal Antibody

Polyclonal antibody was purified from rabbit serum using SNAP25-AffiGel, as described in Materials and Methods. In brief, rabbit serum was diluted 10 times with 10 mM Tris-HCl, pH 7.5, and cleared by centrifugation at 10,000×g for 10 min and filtering through 0.45 μm filter. The clear serum diluent was repeatedly loaded onto a SNAP25-AffiGel three times, and bound proteins were sequentially eluted with 0.1 M sodium acetate, pH 5.5, 0.1 M glycine, pH 4.0, 0.1 M glycine, pH 2.5, and 0.1 M triethylamine, pH 11.5. Protein fractions were collected in tubes containing 0.1 ml of 1 M Tris-HCl, pH 8.0, pooled and concentrated to 1 ml using AMICON Ultra-15. After dialysis with four changes of 1×PBS and 10% glycerol at every 90 min, they were analyzed by SDS-PAGE and ELISA.

Table 9 summarizes the relative distribution of serum proteins in the SNAP25-AffiGel fractions obtained with 4 different batches of rA15 sera.

TABLE 9

| | | Yield (μg) | |
|---|---|---|---|
| Rabbit serum (ml) | pH 5.5 | pH 4.0 | pH 2.5 |
| 30 | 10 | 85 | 350 |
| 30 | 1102 | 525 | 1160 |
| 30 | 936 | 504 | 990 |
| 100 | 64 | 337 | 945 |

Despite that each serum sample exhibited different protein distribution patterns in SNAP25-AffiGel fractions (Table 9), IgG was detected as a major constituent of all fractions examined by 10% SDS-PAGE (FIG. 14a). When tested in sandwich ELISA, however, the reactivity to endogenous SNAP25 was detected only with pH 4.0 fraction. A high signal to background ratio (>25) (FIG. 14b) indicates that IgG in pH 4.0 fraction is highly specific for endogenous SNAP25. Since similar results were obtained with other rabbit sera, pH 4.0 fraction was exclusively used throughout our study employing polyclonal serum unless otherwise indicated.

Example 10: Sequence Analysis of Monoclonal Antibodies

Total RNA, extracted from hybridoma cells, were reversed transcribed to cDNA using either an oligo-dT anti-sense primer or a gene-specific (murine IgG1 CH and kappa CL) anti-sense primer. Specific murine constant domain primers were used to amplify the cDNA by PCR to determine the isotype of the antibody. Degenerate $V_H$ and $V_L$ primers were used to amplify the variable domains from the cDNA. For 5' RACE, a homopolymeric [dC] tail was added to the 3' end of the cDNA. The heavy and light chains were then amplified with an oligo [dG] sense primer and a gene specific (CH/KC) anti-sense primer. The PCR products were cloned into a blunt or TA vector for sequencing. The sequencing results were aligned to $V_H$ and $V_L$ chains to determine consensus sequences.

CDR sequences are summarized in three different groups of IgGs according to their antigenic specificity: (1) SNAP25$_{FL}$-specific IgGs (Table 10), (2) SNAP25$_{197}$-specific IgGs (Table 11), and (3) Bi-specific IgGs, reacting with both SNAP25$_{FL}$ and SNAP25$_{197}$, (Table 12).

TABLE 10

| CDR | SEQ ID NOs | Sequence | Identified In |
|---|---|---|---|
| $V_H$ CDR1 | SEQ ID NO: 11 | GYSITSGYY | D2 |
| | SEQ ID NO: 12 | GYTFTDYN | D6 |
| | SEQ ID NO: 13 | GYTFTNYG | E6 |
| $V_H$ CDR2 | SEQ ID NO: 14 | IRYDGSN | D2 |
| | SEQ ID NO: 15 | IYPYNGDT | D6 |
| | SEQ ID NO: 16 | INTYTGEP | E6 |
| $V_H$ CDR3 | SEQ ID NO: 17 | ARDRDSSYYFDY | D2 |
| | SEQ ID NO: 18 | VRSGDY | D6 |
| | SEQ ID NO: 19 | ARGYYDY | E6 |
| $V_L$ CDR1 | SEQ ID NO: 20 | DHINNW | D2 |
| | SEQ ID NO: 21 | QSLLDSNGKTY | D6 |
| | SEQ ID NO: 22 | QSLLDSDGKTY | E6 |
| $V_L$ CDR2 | SEQ ID NO: 23 | DTT | D2 |
| | SEQ ID NO: 24 | LVS | D6, E6 |
| $V_L$ CDR3 | SEQ ID NO: 25 | QQYWSAPPT | D2 |
| | SEQ ID NO: 26 | WQGTLFPYT | D6 |
| | SEQ ID NO: 27 | WQGTHFPRT | E6 |

TABLE 11

| CDR | SEQ ID NOs | Sequence | Identified In |
|---|---|---|---|
| V_H CDR1 | SEQ ID NO: 28 | GYSITSDYA | C4 |
| | SEQ ID NO: 29 | GFTFNTNA | C7, C14 |
| | SEQ ID NO: 30 | GYTFTNYT | C16 |
| | SEQ ID NO: 31 | GYTFNTYA | C24 |
| | SEQ ID NO: 32 | GFTFSNYG | D3 |
| | SEQ ID NO: 33 | GFTFNTYA | C15 |
| V_H CDR2 | SEQ ID NO: 34 | ISYSVGT | C4 |
| | SEQ ID NO: 35 | IRSKSNNYAT | C7, C15 |
| | SEQ ID NO: 36 | IRSKSDNYAT | C14 |
| | SEQ ID NO: 37 | INPSSDYT | C16 |
| | SEQ ID NO: 38 | IRSKSNNYTT | C24 |
| | SEQ ID NO: 39 | INSNGGTT | D3 |
| V_H CDR3 | SEQ ID NO: 40 | ARKGEYGFAY | C4 |
| | SEQ ID NO: 41 | VYGRSYGGLSY | C7 |
| | SEQ ID NO: 42 | VYGRSYGGLGY | C14 |
| | SEQ ID NO: 43 | VRQVTTAVGGFAY | C15 |
| | SEQ ID NO: 44 | ARRIFYNGRTYAAMDY | C16 |
| | SEQ ID NO: 45 | VGQILYYYVGSPAWFAY | C24 |
| | SEQ ID NO: 46 | ARDRDAMDY | D3 |
| V_L CDR1 | SEQ ID NO: 47 | KSVSTSGYSY | C4, C14, C24 |
| | SEQ ID NO: 48 | KSVSSSGYSY | C7, C15, C16 |
| | SEQ ID NO: 49 | QSIVNSHGNTY | D3 |
| V_L CDR2 | SEQ ID NO: 50 | LAS | C4, C7, C14, C15, C16, C24 |
| | SEQ ID NO: 51 | KVS | D3 |
| V_L CDR3 | SEQ ID NO: 52 | QHSRELPLT | C4, C7, C14, C15, C16 |
| | SEQ ID NO: 53 | QHSRELPWT | C24 |
| | SEQ ID NO: 54 | FQGSHVPWT | D3 |

TABLE 12

| CDR | SEQ ID NOs | Sequence | Identified In |
|---|---|---|---|
| V_H CDR1 | SEQ ID NO: 55 | GFTFSNYG | B4 |
| | SEQ ID NO: 56 | GINIKDYY | B23 |
| V_H CDR2 | SEQ ID NO: 57 | ISSGGSYT | B4 |
| | SEQ ID NO: 58 | IDPGNGDA | B23 |
| V_H CDR3 | SEQ ID NO: 59 | ARHEGGGNPYFDY | B4 |
| | SEQ ID NO: 60 | NEIAY | B23 |
| V_L CDR1 | SEQ ID NOs: 61 | QSLVHSNGNTY | B4 |
| | SEQ ID NO 62 | QSLLDSDGKTY | B23 |
| V_L CDR2 | SEQ ID NO: 63 | KVS | B4 |
| | SEQ ID NO: 64 | LVS | B23 |
| V_L CDR3 | SEQ ID NO: 65 | SQNTLVPWT | B4 |
| | SEQ ID NO: 66 | WQGTHFPFT | B23 |

The V_H and V_L domain sequences of the antibodies produced in the present invention are summarized in Table 13.

TABLE 13

| Antibody | | SEQ ID NOs | Sequence |
|---|---|---|---|
| B4 | V_H | SEQ ID NO: 67 | EVKLVESGGGLVKPGGSLKLSCAASGFTFSNYGMSWVRQTPEKRL EWVATISSGGSYTYYPDSVKGRFTISRDNAKNTLYLQMSSLRSED TAMYYCARHEGGGNPYFDYWGQGTTLTVSS |
| | V_L | SEQ ID NO: 68 | DVLMTQTPLSLPVSLGDQASISCRSSQSLVHSNGNTYLHWYLQKP GQSPKLLIYKVSNRFSGVPDRFSGSGSGTDFTLKISRVEAEDLGV YFCSQNTLVPWTFGGGTKLEIK |
| B23 | V_H | SEQ ID NO: 69 | EVQLQQSGAELVRPGASVKLSCTASGINIKDYYMHWMKQRPEQDL EWIGWIDPGNGDAEYAPKFQGKATMTADTSSNTAYLQLSSLTSED TAVYYCNEIAYWGQGTLVTVSA |
| | V_L | SEQ ID NO: 70 | DIVMTQSPLTLSVTIGQPASISCKSSQSLLDSDGKTYLNWLLQRP GQSPKRLIYLVSKLDSGVPDRFTGSGSGTDFTLKISRVEAEDLGV YYCWQGTHFPFTFGSGTKLEIK |
| C4 | V_H | SEQ ID NO: 71 | DVKLQESGPGLVKPSQSLSLTCTVTGYSITSDYAWNWIRQFPGNK LEWMGYISYSVGTRYNPSLKSRISITRDTSKNQFFLLLKSVTNED TATYFCARKGEYGFAYWGQGTLVTVSA |
| | V_L | SEQ ID NO: 72 | DIVMTQSPASLAVSLGQRATISCRASKSVSTSGYSYMHWYQQKPG QPPKLLIYLASNLESGVPARFSGSGSGTDFTLNIHPVEEEDAATY YCQHSRELPLTFGAGTKLELK |

TABLE 13-continued

| Antibody | | SEQ ID NOs | Sequence |
|---|---|---|---|
| C7 | $V_H$ | SEQ ID NO: 73 | QVQLVETGGGLVQPKGSLKLSCAASGFTFNTNAMNWVRQAPGKGL EWVARIRSKSNNYATYYADSVKDRFTISRDDSQSLLYLQMNNLKT EDTAMYYCVYGRSYGGLSYWGQGTLVTVSA |
| | $V_L$ | SEQ ID NO: 74 | DIVMTQSPASLAVSLGQRATISCRASKSVSSSGYSYMHWYQQKPG QPPKLLIYLASNLESGVPARFSGSGSGTDFTLNIHPVEEEDAATY YCQHSRELPLTFGAGTKLELK |
| C14 | $V_H$ | SEQ ID NO: 75 | EVKLVESGGGLVQPKGSLKLSCAASGFTFNTNAMNWVRQAPGKGL EWVARIRSKSDNYATYYADSVKDRFTISRDDSPSMLYLQMNNLKT EDTAMYYCVYGRSYGGLGYWGQGTLVTVSA |
| | $V_L$ | SEQ ID NO: 76 | DIVLTQSPASLAVSLGQRATISCRASKSVSTSGYSYVHWYQQKPG QPPKLLIYLASNLESGVPARFSGSGSGTDFTLNIHPVEEEDAATY YCQHSRELPLTFGAGTKLELK |
| C15 | $V_H$ | SEQ ID NO: 77 | EVKLVESGGGLVQPKGSLKLSCAASGFTFNTYAMNWVRQAPGKGL EWVARIRSKSNNYATYYADSVKDRFTISRDDSQSMLYLQMNNLKT EDTAMYYCVRQVTTAVGGFAYWGQGTLVTVSE |
| | $V_L$ | SEQ ID NO: 78 | DIVMTQSPASLAVSLGQRTTISCRASKSVSSSGYSYMHWYQQKPG QPPKLLIYLASNLESGVPARFSGSGSGTDFTLNIHPVEEEDAATY YCQHSRELPLTFGAGTKLELR |
| C16 | $V_H$ | SEQ ID NO: 79 | EVQLQQSGAELARPGASVQMSCKAFGYTFTNYTMHWVRQRPGQGL EWIGFINPSSDYTNYNQKFKDKATLSADKSSSTAYMQLSSLTSED SAVYYCARRIFYNGRTYAAMDYWGQGTSVTVSS |
| | $V_L$ | SEQ ID NO: 80 | DIVMTQSPASLAVSLGQRATISCRASKSVSSSGYSYMHWYQQKPG QPPKLLIYLASNLESGVPARFSGSGSGTDFTLNIHPVEEEDAATY YCQHSRELPLTFGAGTKLELK |
| C24 | $V_H$ | SEQ ID NO: 81 | EVKLVESGGGLVQPKGSLKLSCAASGYTFNTYAMNWVRQAPGKGL EWVARIRSKSNNYTTYYADSVKDRFTISRDDSQSMLYLQINNLKT EDTAMYYCVGQILYYYVGSPAWFAYWGQGTLVTVSA |
| | $V_L$ | SEQ ID NO: 82 | DIVMTQSPASLAVSLGQRATISCRASKSVSTSGYSYMHWYQQKPG QPPKLLIFLASNLESGVPARFSGSGSGTDFTLNIHPVEEEDAATY YCQHSRELPWTFGGGTKLEIK |
| D2 | $V_H$ | SEQ ID NO: 83 | DVKLQESGPGLVKPSQSLSLTCSVTGYSITSGYYWNWIRQFPGNK LEWMGYIRYDGSNNYNPSLKNRISITRDTSKNQFFLKLNSVTTED TASYYCARDRDSSYYFDYWGQGTALTVSS |
| | $V_L$ | SEQ ID NO: 84 | DIVMTQSSSYLSVSLGGRVTITCKASDHINNWLAWYQQKPGNAPR LLISDTTSLETGVPSRFSGSGSGKDYTLSITSLQTEDVATYYCQQ YWSAPPTFGGGTKLEIK |
| D3 | $V_H$ | SEQ ID NO: 85 | EVQLEESGGGLVQPGGSLKLSCAASGFTFSNYGMSWVRQTPDKRL ELVATINSNGGTTYYPDSVKGRFTISRDNAKNTLYLQMSSLKSED SAMYYCARDRDAMDYWGQGTSVTVSS |
| | $V_L$ | SEQ ID NO: 86 | DVLMTQTPLSLPVSLGDQASISCRSSQSIVNSHGNTYLEWYLQKP GQSPKLLIYKVSNRFSGVPDRFSGSGSGTDFTLKISRVEAEDLGV YYCFQGSHVPWTFGGGTKLEIK |
| D6 | $V_H$ | SEQ ID NO: 87 | EVQLQQSGPELVKPGASVKISCKASGYTFTDYNMHWVKQSHGKSL EWIGYIYPYNGDTGYNQKFKSKATLTVDNSSSTAYMELRSLTSED SAVYYCVRSGDYWGQGTTLTVSS |
| | $V_L$ | SEQ ID NO: 88 | DVLMTQTPLTLSVTIGQPASISCKSSQSLLDSNGKTYLNWLLQRP GQSPSRLIYLVSKLDSGVPDRFTGSGSGTDFTLKISRVEAEDLGV YYCWQGTLFPYTFGGGTKLEIK |
| E6 | $V_H$ | SEQ ID NO: 89 | QIQLAQSGPELKKPGETVKISCKASGYTFTNYGMSWVKQAPGKGL KWMGWINTYTGEPTYAADFKGRFAFSLETSASTAFLQINNLKNED TATYFCARGYYDYWGQGTTLTVSS |
| | $V_L$ | SEQ ID NO: 90 | DVLMTQTPLTLSVTIGQPASISCKSSQSLLDSDGKTYLNWLLQRP GQSPKRLIYLVSKLDSGVPDRFTGSGSGTDFTLKISRVEAEDLGV YYCWQGTHFPRTFGGGTKLEIK |

It is interesting to note that $V_L$ CDR3 sequence is shared by SNP25$_{197}$-specific IgGs such as C4, C7, C14, C15, and C16 IgG, whereas their $V_H$ sequences tend to be IgG-specific (Table 11). Sequence alignment analysis revealed that not a single CDR sequence of IgGs, listed in Tables 10-12, overlaps with $V_L$ and $V_H$ CDR sequences of previously reported IgGs (U.S. Pat. No. 8,198,034B2). This may be ascribed to employment of a more stringent screening strategy for positive hybridoma cells in the present research. That is, throughout multiple rounds of screening, only triple positive hybridoma clones were selected by direct ELISA using peptide antigen, sandwich ELISA with TCL, and Western blot analysis with TCL. This stringent screening strategy must have contributed to significantly lower $K_D$ values of IgGs obtained in the present research (see below).

Example 11: Kinetics Analysis of Monoclonal Antibodies

As detailed in Materials and Methods, the kinetics analysis of monoclonal antibody was exclusively carried out by the BLI assay using FORTÉBIO® Octet Red96 instrument, following the procedure recommended by the manufacturer. Firstly, kinetics analysis was performed with SNAP25$_{197}$- specific IgGs using anti-GST biosensors loaded with recombinant GST-SNAP25$_{197}$ (125 nM or 250 nM). FIG. 15 shows a set of kinetics curves obtained with C4, C7, C16, and C24, as an example of such studies. In brief, anti-GST biosensors, loaded with GST-SNAP25$_{197}$, were sequentially dipped in 1× kinetics buffer, serially diluted IgG samples (7.8, 15.6, 31.2, 62.5, 125, 250, 500 nM) (analyte association), and 1× kinetics buffer (analyte dissociation). Subsequent to association and dissociation of analyte for 10 min each, raw data of kinetics curves were obtained (FIG. 15a). Kinetics curves were then aligned by subtracting baseline BLI signal (FIG. 15b), from which K$_D$ was estimated using FORTÉBIO® Octet analysis software (Table 14).

nM, whereas GST-SNAP25$_{FL}$ or SNAP25$_{197}$ was serially diluted to 1.56, 3.125, 6.25, 12.5, 25, 50, and 100 nM. After equilibration in 1× kinetics buffer for 1 min, AMC biosensors were loaded with IgGs for 10 min, followed by dipping in 1× kinetics buffer for 10 min. Association and dissociation of analyte were carried out for 10 min each, and K$_D$ was estimated as described above.

Estimated K$_D$ values using FORTÉBIO® Octet analysis software are listed in Table 15.

TABLE 15

| IgGs | | | Kinetics Parameters with SNAP25$_{197}$ | | | Kinetics Parameters with SNAP25$_{FL}$ | | |
|---|---|---|---|---|---|---|---|---|
| | | | K$_{on}$ (M$^{-1}$s$^{-1}$) | K$_{dis}$ (s$^{-1}$) | K$_D$ (pM) | K$_{on}$ (M$^{-1}$s$^{-1}$) | K$_{dis}$ (s$^{-1}$) | K$_D$ (pM) |
| Bi-specific | | $^a$A15 | 7.78 × 10$^4$ | 1.22 × 10$^{-7}$ | 1.56 ± 0.01 | 8.39 × 10$^4$ | 1.0 × 10$^{-7}$ | 1.19 ± 0.62 |
| | | $^a$B4 | 1.0 × 10$^5$ | 5.56 × 10$^{-7}$ | 0.48 ± 0.02 | 9.51 × 10$^4$ | 1.0 × 10$^{-7}$ | 0.10 ± 0.38 |
| | | $^a$B23 | 2.54 × 10$^4$ | 1.0 × 10$^{-7}$ | 3.27 ± 0.03 | 9.58 × 10$^4$ | 1.0 × 10$^{-7}$ | 0.10 ± 0.42 |
| SNAP25$_{197}$-specific | | $^b$C4 | 9.28 × 10$^4$ | 1.0 × 10$^{-7}$ | 1.07 ± 0.60 | (not determined) | | |
| | | $^b$C7 | 7.78 × 10$^4$ | 1.0 × 10$^{-7}$ | 1.28 ± 0.75 | | | |
| | | $^a$C14 | 7.67 × 10$^4$ | 1.0 × 10$^{-7}$ | 1.30 ± 0.75 | | | |
| | | $^b$C16 | 1.60 × 10$^6$ | 2.57 × 10$^{-6}$ | 1.62 ± 0.46 | | | |
| | | $^a$C24 | 8.68 × 10$^4$ | 1.0 × 10$^{-7}$ | 1.15 ± 0.87 | | | |
| | | $^b$D3 | 1.11 × 10$^5$ | 1.0 × 10$^{-7}$ | 0.90 ± 0.59 | | | |
| SNAP25$_{FL}$-specific | | $^b$D2 | (not determined) | | | 1.64 × 10$^5$ | 1.0 × 10$^{-7}$ | 0.61 ± 0.28 |
| | | $^b$D6 | | | | 3.52 × 10$^4$ | 1.0 × 10$^{-7}$ | 2.84 ± 0.02 |
| | | $^b$E6 | | | | 5.38 × 10$^4$ | 1.0 × 10$^{-7}$ | 1.86 ± 0.59 |

TABLE 14

| | | SPR Kinetic Parameters (SNAP25$_{197}$) | | |
|---|---|---|---|---|
| Monoclonal Abs | | K$_{on}$ (M$^{-1}$s$^{-1}$) | K$_{dis}$ (s$^{-1}$) | K$_D$ (nM) |
| SNAP25$_{197}$ specfic (dipped in 125 nM) | C4 | 2.30 × 10$^5$ | 4.10 × 10$^{-3}$ | 17.8 ± 4.45 |
| | C7 | 2.57 × 10$^5$ | 4.94 × 10$^{-3}$ | 19.3 ± 3.15 |
| | C16 | 2.35 × 10$^5$ | 2.15 × 10$^{-3}$ | 9.17 ± 2.71 |
| | C24 | 5.29 × 10$^5$ | 5.09 × 10$^{-3}$ | 9.62 ± 1.30 |
| SNAP25$_{197}$ specific (dipped in 250 nM) | C4 | 2.27 × 10$^5$ | 1.48 × 10$^{-3}$ | 6.53 ± 1.09 |
| | C7 | 2.77 × 10$^5$ | 1.22 × 10$^{-3}$ | 4.41 ± 0.68 |
| | C16 | 2.36 × 10$^5$ | 1.52 × 10$^{-3}$ | 6.44 ± 1.25 |
| | C24 | 4.58 × 10$^5$ | 2.41 × 10$^{-3}$ | 5.25 ± 1.09 |

Considering the nM range of K$_D$ values, kinetics analysis seemed to normally proceed. However, when kinetics analysis was performed with a biosensor dipped in a lower concentration of GST-SNAP25$_{197}$ (125 nM), K$_D$ values proportionally decreased, mainly due to changes in dissociation rate constant Kdis (Table 14). It was also at odd that Kdis values (1.22-5.09×10$^{-3}$) were 1 or 2 orders of magnitude lower than previously reported ones (3.11×10$^{-4}$-6.74×10$^{-5}$) for monoclonal antibodies with a similar antigen specificity (US patent U.S. Pat. No. 8,198,034B2).

Two plausible causes can be considered for relatively high K$_D$ and Kdis values. The first is the use of inappropriate assay buffer, and the second is the inherent limitation of the entire kinetics assay performed with anti-GST biosensor (FortéBio Application Note 14: Biomolecular Binding Kinetics Assays on the Octet Platform). Comparative use of diverse assay buffers in the kinetics assay showed that 1× kinetics buffer was the most appropriate among all buffers tested (data not shown). Therefore, as an alternative kinetics analysis, anti-mouse IgG Fc capture (AMC) biosensors were directly loaded with antibody and subjected to association/dissociation with serially diluted recombinant GST-SNAP25. In brief, purified IgG was diluted to 100 or 200 nM, whereas GST-SNAP25$_{FL}$ or SNAP25$_{197}$ was serially diluted to 1.56, 3.125, 6.25, 12.5, 25, 50, and 100 nM.

The most noticeable would be Kdis values (i.e. 2.57×10$^{-6}$-1.0×10$^{-7}$) (Table 15), which is two to three orders of magnitude lower than those obtained with anti-GST biosensor (Table 14). In fact, dissociation rates were too low to be accurately measured using FORTÉBIO® Octet, so the lowest limit of Kdis value, 1.0×10$^{-7}$, was tentatively given for six IgGs, as described in Table 15.

Estimation of K$_D$ values with these tentative dissociation rate constants yielded 0.48~3.27 pM. It should be noted that AMC biosensors loaded with SNAP25$_{197}$-specific IgGs did not show statistically significant extent of association of GST-SNAP25$_{FL}$ up to 1 µM. Similarly, GST-SNAP25$_{197}$ did not associate with AMC biosensors loaded with SNAP25$_{FL}$-specific IgGs. These binding specificities of IgGs are in a good agreement with their reactivity in ELISA.

Example 12: Antigen Binding Specificity of Monoclonal Antibodies

Monoclonal antibodies were comparatively examined for their reactivity toward SNAP25$_{FL}$ and SNAP25$_{197}$ employing direct ELISA and Western blot analysis. First, direct ELISA was performed with a purified IgG (50 ng per well) in a microplate coated with GST-SNAP25$_{FL}$ or GST-SNAP25$_{197}$, as described in Materials and Methods. HRP reaction was carried out for 5 min and the extent of HRP activity was determined by measuring A$_{450}$ using Bio-Tek SynergyNeo2. A$_{450}$ values were obtained after subtracting background A$_{450}$, measured without IgG, and the ratio of A$_{450}$ with SNAP25$_{197}$ to A$_{450}$ with SNAP25$_{FL}$ was calculated and presented as Ratio$_{197/206}$ in Table 16. Consistent with the result obtained by the BLI assay, Ratio$_{197/206}$ values for bi-specific IgGs such as A15, B4, and B23, were close to 1.0. Ratio$_{197/206}$ values for SNAP$_{197}$-specific IgGs such as C7, C14, C16, and C24, were over 950, but SNAP25$_{FL}$-specific IgGs yielded 0.02~0.03 of Ratio$_{197/206}$.

TABLE 16

| IgGs | $A_{450}$ with $SNAP25_{FL}$ | $A_{450}$ with $SNAP25_{197}$ | Ratio$_{197/206}$ |
|---|---|---|---|
| A15 | 1.383 | 1.445 | 1.04 |
| B4 | 2.163 | 1.797 | 0.83 |
| B23 | 1.901 | 1.754 | 0.92 |
| C4 | 0.001 | 0.919 | 919 |
| C7 | 0.001 | 1.199 | 1,037 |
| C14 | 0.001 | 0.953 | 953 |
| C16 | 0.001 | 0.996 | 996 |
| C24 | 0.001 | 0.973 | 973 |
| D3 | 0.125 | 1.616 | 12.93 |
| D2 | 1.448 | 0.048 | 0.03 |
| D6 | 1.878 | 0.031 | 0.02 |
| E6 | 1.808 | 0.039 | 0.02 |

Western blot analysis was performed with hybridoma culture supernatants (1:100 dilution) as the source of primary antibody. Aliquots (0.5 µg) of GST-SNAP25$_{FL}$ and GST-SNAP25$_{197}$, resolved on a denaturing gel and subsequently transferred to PVDF membrane, were tested as antigen. Monoclonal antibodies reacted with denatured SNAP25 antigen with the same specificity as in the ELISA assay (FIG. 17). These results are not unexpected since only double positive hybridoma cells were selected by a stringent ELISA and Western blot analysis.

Example 13: Conjugation of Horseradish Peroxidase (HRP) to Antibodies

Among monoclonal antibodies tested, C16 IgG exhibited the most reproducible retention of antigenic affinity and specificity after being conjugated with HRP (data not shown). In a typical HRP conjugation reaction, C16 IgG (5 mg) was incubated with activated HRP (5 mg) for 2 hr at RT with light protection, as described in Materials and Methods. After the addition of 0.1 ml of sodium borohydride (4 mg/ml), the HRP-antibody conjugate was dialyzed against 1×PBS and 1×PBS/50% glycerol at 4° C. As shown in FIG. 18a, conjugation of activated HRP to C16 IgG was very efficient that the formation of C16 IgG-HRP conjugate was detectable even without incubation (compare lanes 1-3). Incomplete conjugation of C16 IgG, reflected as free IgG and HRP (lanes 4-6), suggests the requirement of relatively high concentrations of free HRP and IgG in the reaction mixture for efficient conjugation.

Two different C16 IgG-HRP conjugates were examined for the reactivity toward SNAP25$_{197}$ in direct ELISA. A 96-well microplate was coated with 0-200 pg of GST-SNAP25$_{197}$, mimicking approximately up to ~0.8% cleavage of endogenous SNAP25 in cells grown in a microplate well. Aliquots (200 ng) of C16 IgG-HRP conjugates were capable of detecting as low as 50 pg of GST-SNAP25$_{197}$ when measured for 30 min with 50 µl of 1-Step™ Ultra TMB-ELISA (FIG. 18b). Also, higher A450 values were obtained in proportion with increased amounts of GST-SNAP25$_{197}$. Based on these results, C16-HRP conjugates were exclusively used as detection antibody in the optimized sandwich ELISA.

Example 14: Conjugation of Biotin to Antibodies

Sandwich ELISA developed by Allergan utilizes two antibodies: a SNAP25$_{197}$-specific IgG as capture antibody and polyclonal SNAP25-specific IgG as detection antibody. By contrast, sandwich ELISA invented by the present research utilizes two monoclonal antibodies as capture either detection antibody, which makes its quality control more feasible and easier. This novel sandwich ELISA exhibits high levels of repeatability, reproducibility and accuracy. Yet the addition of a second detection antibody such as IgG conjugated with alkaline phosphatase or biotin could further improve the accuracy of sandwich ELISA through normalization of SNAP25 captured in each well.

As the first attempt, a bi-specific monoclonal antibody A15 was conjugated with biotin, as described in Materials and Methods. As shown in FIG. 19 the higher biotin concentration was provided, the more biotin molecules were conjugated per IgG. Quantitation of biotin conjugation using HABA/Avidin Premix (Thermo Scientific) revealed that about 8 moles of biotin were conjugated per mole of IgG in a reaction provided with 0.25 mM biotin. Consistently, the heavy chain of IgG conjugated with 0.5 mM biotin exhibited noticeably slower migration on SDS-PAGE (FIGS. 19a & 19b).

Figure 19C:
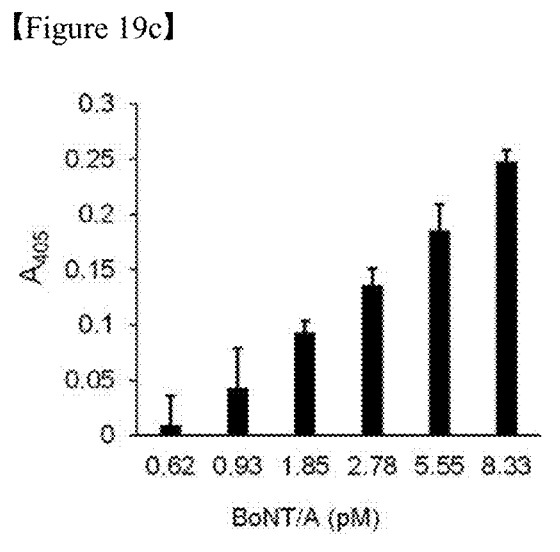

The reactivity of A15 IgG conjugated with 0.1 mM biotin was tested in sandwich ELISA. In brief, TCLs (60 µl) were prepared from N2-42F cells treated with the indicated concentration of BoNT/A. A microplate coated with B4 IgG was incubated with 50 µl aliquots of TCL, and. endogenous SNAP25$_{197}$ captured by B4 IgG was detected by incubation with A15-biotin conjugate and streptavidin-AP conjugate (1:500 dilution in 1×TBS). As a bi-specific monoclonal antibody, A15 IgG has been characterized to bind both SNAP25$_{FL}$ and SNAP25$_{197}$ with comparable affinity and specificity (see FIG. 17). These properties are among criteria to select A15 IgG as the potential second detection antibody for the purpose of normalization. Thus, it was expected that A15 binding to SNAP25 remain relatively unaffected by the extent of SNAP25 cleavage. On the contrary, however, AP activity, reflecting the SNAP25 binding of biotinylated A15 IgG, increased in proportion to BoNT/A concentration (FIG. 19c). This result might be explained by the change in its antigen specificity upon biotinylation of both light and heavy chains of IgG (FIG. 19b).

Example 15: Direct Cross-Linking of Alkaline Phosphatase (AP) to Antibodies

As an alternative approach to the second detection antibody, purified IgGs were directly cross-linked to AP using glutaraldehyde as the extent of cross-linking can be regulated by glutaraldehyde concentration. Two polyclonal and three monoclonal antibodies were cross-linked to AP using glutaraldehyde. Except C16, they were all bi-specific antibodies reacting with both SNAP25$_{FL}$ and SNAP25$_{197}$, a key property as the second detection antibody for normalization. C16 IgG was used as control since HPR conjugation was efficient, yet not affecting the antigen specificity of C16 (FIG. 18). In search for an optimal condition to obtain AP-IgG conjugate retaining its antigen specificity and reactivity, crosslinking of AP to IgG was performed with diverse ratios of IgG to AP under different incubation conditions (Table 17).

TABLE 17

| Antibody | Ratio of IgG to AP | Incubation time/temperature | Analysis |
|---|---|---|---|
| C1 | 1:3 | 2 hr/4° C. + 2 hr/RT | SDS-PAGE |
| C16 | 1:1~2:1 | 3-24 hr/RT or 37° C. | |
| A15 | 1:1~2:1 | 5 hr/37° C. | SDS-PAGE |

TABLE 17-continued

| Antibody | Ratio of IgG to AP | Incubation time/temperature | Analysis |
|---|---|---|---|
| rA15 | 2:1 | 2 hr/4° C. + 2 hr/RT | & direct |
| Sigma IgG | 2:1 | 1-4 hr/4° C. or RT | ELISA |

Upon completion of glutaraldehyde cross-linking, the resulting AP-IgG conjugates were analyzed by SDS-PAGE. A representative result showing the electrophoretic resolution of AP-IgG conjugates and the subsequent visualization by Coomassie blue staining is shown in FIG. 20. In brief, polyclonal anti-SNAP25 IgG (Sigma) was cross-linked to AP in a reaction provided with 0.2% glutaraldehyde. Cross-linking of AP was highly efficient that all IgGs provided formed high molecular weight complexes with AP. The resulting AP-IgG conjugates exhibited much slower migration on a SDS gel, and some failed to enter the stacking gel portion (FIG. 20a). Similar patterns were obtained with all IgGs tested (data not shown).

Following the confirmation of the cross-linking by SDS-PAGE analysis, AP-rA15 IgG and AP-Sigma IgG conjugates (100 ng per well) were comparatively examined for the antigen reactivity and specificity in direct ELISA using a microplate coated with 2 ng of GST-SNAP25 mixtures containing varying extents of GST-SNAP25$_{197}$. AP-Sigma IgG conjugates did not yield any ELISA signal, whereas AP-rA15 IgG conjugates led to a result similar to that with biotinylated A15 IgG (compare FIG. 19 and FIG. 20b). With increasing amounts of GST-SNAP25$_{197}$, higher ELISA signals were obtained with AP-rA15 IgG conjugates.

The results in FIGS. 19 & 20 suggest that in case of SNAP25$_{FL}$-reacting antibodies, be it monoclonal or polyclonal, both heavy and light chains of IgG are efficiently conjugated to activated biotin or cross-linked to AP by glutaraldehyde. Thus, the second detection antibody remains to be developed until a more Fc-specific conjugation technology is available.

Example 16: Optimization of Culture of N2-42F, and Treatment with BoNT/A

Having acquired key reagents such as neuronal cells highly sensitive to BoNT/A and monoclonal antibodies specific for SNAP25, a series of experiments were carried out to optimize all steps in the cell-based potency assay, including the intoxication medium, sensitizer, BoNT/A treatment time, and capture/detection antibody pairing.

Example 16-1. Optimization of BoNT/a Intoxication Time

First, the BoNT/A processing time (toxinization time) was optimized.

Protocol A (FIG. 21a) is a standardized CBPA procedure optimized for SiMa. To examine the BoNT/A sensitivity following Protocol A, N2-42F cells were plated at $5.6 \times 10^5$ cells per well in a 12-well culture plate, and on next day, the medium was replaced with 1× intoxication medium without GT/1b. Two days later, medium was supplemented with GT1b (25 mg/ml), and after one more day of incubation, culture medium was replenished with 1× intoxication medium containing BoNT/A and incubated for additional 2 days. Protocol B (FIG. 21b) is a CBPA procedure developed in this research. In brief, N2-42F cells were plated at $5.6 \times 10^5$ cells per well in a 12-well culture plate, and on next day, the medium was replaced with 1× intoxication medium containing 25 pM BoNT/A. Total cell lysates were prepared on the indicated day by adding 1×SDS sample buffer (200 μl per well) and stored at −20° C. before use. Aliquots (12 μl) were subjected to 12% SDS-PAGE, and SNAP25$_{FL}$ and SNAP25$_{197}$ were detected by Western blotting using polyclonal anti-SNAP25 IgGs (Sigma 59684, 1:8,000 dilution) and goat anti-rabbit IgG Fc-HRP (AbFrontier LF-SA8002, 1:8,000 dilution). The extent of SNAP25 cleavage was quantified using the Image Lab software (Bio-Rad).

As described above, towards establishment of the optimal intoxication time for N2-42F cells, Protocol A was modified by prolonging the cell culture time in either 1× intoxication medium devoid of GT1b or in 1× intoxication medium containing BoNT/A. These changes did not improve the extent of SNAP25 cleavage and moreover, N2-42F cells grown in the 1× intoxication medium for more than 4 days looked very unhealthy under the microscope (data not shown). Based on this observation, a novel Protocol B was established, where the culture time in 1× intoxication medium supplemented with both GT1b and BoNT/A was shortened (FIG. 21b). With the lapse of day, starting from the third day (d4) subsequent to the cell plating, the extents of SNAP25 cleavage in N2-42F cells was comparatively analyzed by Western blot. As shown in FIG. 21c, less than 20% of SNAP25 cleavage was estimated on d4, but the prolonged culture of N2-42F cells beyond d4 in 1× intoxication medium supplemented with GT1b and BoNT/A led to significant increase in the SNAP25 cleavage up to 64% on d7. Since N2-42F cells on d7 looked unhealthy under the microscope, d6 was determined as the day of N2-42 cell harvesting and sandwich ELISA analysis to measure the BoNT/A potency.

Example 16-2. Optimization of Culture Medium

The osmolarity and temperature influenced the BoNT/A sensitivity of BOCELL™ (U.S. Pat. No. 9,526,345B2). Also, the BoNT/A sensitivity of NG108-15 cells was significantly improved by optimizing neural differentiation medium (J Biomol Screen. 2016 January; 21(1):65-73). Since the BoNT/A sensitivity reflects the extent of BoNT/A uptake through two independent receptors on cell surface, a polysialoganglioside (PSG) receptor and a protein receptor (SV2) (J Neurochem. 2009 June; 109(6):1584-95), the enhanced BoNT/A sensitivity by optimization of culture medium or higher temperature has to do with the facilitated cellular intake of BoNT/A. To this end, N2-42F cells was tested for the BoNT/A sensitivity in three different culture media: RPMI1640, NEUROBASAL™, and MEM, all supplemented with 1× N2, 1× B27, and 1× GT1b. While culturing in the indicated medium, N2-42F cells were treated with varying concentrations (0.93~25 pM) of BoNT/A cells according to Protocol B. When measured by Western analysis, the BoNT/A sensitivity of N2-42F cells was measured the highest with RPMI1640 (FIG. 22). The BoNT/A sensitivity measured with NEUROBASAL™ or MEM was 25% or 50% lower than with RPMI1640. The KCl content is commonly 5.33 mM in all media, but the NaCl concentration is 103 mM in RPMI1640, 117 mM in MEM, and 52 mM in NEUROBASAL™ medium. Despite this difference, the osmolality of cell culture media for most vertebrate cells is known to be kept within a narrow range from 260 mOsm/kg to 320 mOsm/kg (ATCC Culture Cell Guide). Thus, the BoNT/A sensitivity of N2-24F cells in RPMI1640 is likely to be contributed by as yet unidentified medium component other than the osmolarity.

Under the condition described in FIG. 22, about 48% of endogenous SNAP25 was cleaved in N2-42F cells by 8.33 pM BoNT/A, equivalent to about 10 units/ml potency. Since the culture volume in a 96-well plate is 0.1 ml, the EC50 can be estimated to be ~1 U bio-potency of BoNT/A per well in a microplate. Thus, the BoNT/A sensitivity measured with N2-42F cells following Protocol B is sensitive enough to measure the bio-potency of BoNT/A determined by the mouse LD50 bioassay.

Example 16-3. Identification and Optimization of Sensitizers

Taking advantage of having fully characterized monoclonal antibodies specific for SNAP25 (see below), the BoNT/A sensitivity of N2-42F cells in the 1× intoxication medium containing varying concentrations of BoNT/A (0.03-5.5 pM) were examined by sandwich ELISA assay following Protocol B, while testing if the BoNT/A sensitivity is affected by arginine (see above) or any compounds with demonstrated effects on neural survival or differentiation, including ATP (Trends Neurosci. 2000 December; 23(12):625-33), creatine (J Neurochem. 2005 October; 95(1):33-45), and lipoic acid (J Neurosci Res. 2014 January; 92(1):86-94). As shown in FIG. 23a, the addition of 1 mM creatine or 5 mM arginine in the 1× intoxication medium noticeably enhanced the BoNT/A sensitivity, lowering EC50 value from 2.51 pM to 2.13 or 2.03 pM, respectively. By contrast, ATP and lipoic acid acted as very effective inhibitors that the SNAP25 cleavage in N2-42F cells was not detected even with 25 pM BoNT/A.

In an optimization study for the toxinized medium, it was believed that the BoNT/A sensitivity of N2-24F cells was affected by factors other than osmotic pressure. Because the sensitivity was higher in RPMI1640 medium than in Neurobasal™ or MEM medium. For arginine in the medium composition, it contained 1.15 mM in RPMI1640, 0.6 mM in MEM, and 0.4 mM in Neurobasal™. Since arginine is a precursor amino acid of creatine, arginine alone was further examined for its effects on the BoNT/A sensitivity using 2× intoxication medium containing 2-10 mM arginine. As shown in FIG. 23b, the BoNT/A sensitivity was gradually enhanced with increasing arginine concentration up to 5 mM, as reflected by lowered EC50 values. The BoNT/A sensitivity with 10 mM arginine (EC50=2.34 pM), though still higher than control (EC50=2.94 pM), was lower than with 5 mM arginine (EC50=1.65 pM). Based on this result, although its mechanism of action remains yet to be understood, the optimized standard protocol of CBPA uses the intoxication medium containing 5 mM arginine.

In 2002, Schengrund and his coworkers provided experimental evidence for the first time that in neuro-2a cells, an efficient SNAP25 cleavage by BoNT/A requires higher than 25 µg/ml GT1b in DMEM (J Biol Chem. 2002 Sep. 6; 277(36):32815-9). Since N2-42F cells are derived from neuro-2a, the requirement of GT1b for BoNT/A activity was examined using the 1× intoxication medium containing 25-75 µg/ml GT1b (1~3× GT1b) by Western blot analysis. Without GT1b supplementation, 8.3 pM BoNT/A led to about 18% of SNAP25 cleavage (FIG. 24a). Addition of 1× or 3× GT1b resulted in 10% and 18% increase in SNAP25 cleavage by 8.3 pM BoNT/A, respectively, in N2-42F cells (FIG. 24a).

Towards optimization of GT1b concentration, the BoNT/A sensitivity of N2-42F cells were tested in 2× intoxication medium containing 25 pM BoNT/A and increasing concentrations of GT1b from 1× to 5×. When measured by Western blot analysis, the SNAP25 cleavage was significantly enhanced by the addition of 1× or 2×GT1b, but with more than 2×GT1b, the SNAP25 cleavage only marginally increased from 63%, 65%, 68%, to 70% (FIG. 24b). A parallel test was performed employing the optimized sandwich ELISA. Considering the sensitivity of sandwich ELISA, N2-42F cells were treated with 0.93 pM BoNT/A in 2× intoxication medium following Protocol B. Sandwich ELISA more profoundly exhibited the requirement of GT1b for the BoNT/A activity. In brief, when N2-42F cells were treated with BoNT/A in the intoxication medium lacking GT1b, relatively low A450 values were obtained in sandwich ELISA (FIG. 24c). By contrast, the addition of GT1b to the intoxication medium led to marked increases in A450 value. The result showing a steady increase in A450 value with up to 2×GT1b may reflect efficient and stable trimolecular interaction between BoNT/A, GT1b, and polysialoganglioside (PSG) receptor. Therefore, saturated A450 value obtained with 4×GT1b and even decreased A450 value with 5× may be explained by saturation of PSG receptor and/or the effect of molar excess of free GT1b that competes with BoNT/A-GT1b complex for PSG receptor. Based on this reasoning, 2×, that is 50 µg/ml, was selected as an optimal concentration of GT1b when the BoNT/A activity is measured using N2-42F cells.

The effect of N2 (N2 supplement, Thermo Fisher Scientific 17502048)/B27(B27™ Serum free supplement, Thermo Fisher Scientific 17504-044) in neuron cultures on BoNT/A sensitivity was tested. B27, containing all trans-retinol (0.1 mg/L), is known to support motor neuron differentiation of neural progenitor cell (J Cell Biochem. 2008 Oct. 15; 105(3):633-40). N2 contains a subset of B27 components, including insulin and is known to promote (1) differentiation of human embryonic stem cells and (2) proliferation/survival of neural progenitor cell (J Cell Biochem. 2008 Oct. 15; 105(3):633-40). The BoNT/A sensitivity of N2-42F cells in RPMI1640 supplemented with 1× GT1b, 8.3 pM BoNT/A and the indicated concentration of N2/B27 following Protocol B. The SNAP25 cleavage was quantitatively analyzed by Western blot. As shown in FIG. 25a, intracellular levels of total SNP25 ($SNAP25_{FL}$+$SNAP25_{197}$) increased in proportion to N2/B27 concentration, whereas the level of $SNAP25_{197}$ remained relatively unchanged and even decreased in the presence of 4× or 5× N2/B27. A recent study reported that N2 and B27 function jointly to protect neuron from cell death after glucose depletion by restricting glycolysis (Front Mol Neurosci. 2017 Sep. 29; 10:305). Consistently, the result in FIG. 25a is very likely reflect the enhanced synthesis of endogenous SNAP25 with increasing concentrations of N2/B27 as part of their function to promote cell proliferation and survivor in serum-free RPMI1640 medium containing relatively low concentration of glucose (11.1 mM).

Using RPMI1640 supplemented with 3×GT1b and 5 mM arginine, the effects of N2/B27 on the BoNT/A activity were further examined. The extent of SNAP25 cleavage in N2-42F cells treated with 8.3 pM BoNT/A was enhanced from 13% to 56%, 69% by 1× and 2× N2/B27 in spite of noticeable increase in overall intracellular level of SNAP25 (FIG. 25b). Based on this observation, 2× N2/B27 is added to the optimized intoxication medium.

Example 17: Optimization of Sandwich ELISA

Example 17-1. Optimization of Buffers

Having optimized the culture medium and media supplements for N2-42F cell intoxication, next, sandwich ELISA was systematically evaluated for its performance under diverse conditions summarized in Table 18. And selected optimized conditions summarized in Table 19.

TABLE 18

| Parameters | Conditions tested | Optimal condition |
|---|---|---|
| Plate coating matrix | 3 matrices | Poly-D-lysine |
| Cell density | 2 densities | $5.5 \times 10^4$ cells per well |
| Intoxication medium/ sensitizer | 3 culture media/ 6 sensitizers | RPMI1640, 2 mM L-alanyl-L-glutamine, 0.1 mM NEAA, 2x N2, 2x B27, GT1b (50 µg/ml), 5 mM arginine |
| Intoxication time | 3 time points | 96 hr |
| BoNT/A dose | 0.03 pM-1 nM | 0.03-8.33 pM |
| Capture/ detection antibodies | 11 combinations | B4 (300 ng/50 ml) + C16-HRP (200 ng/50 ml) |
| Lysis buffers | 11 buffers | 20 mM Hepes-NaOH, pH 7.5, 0.2M NaCl, 1% TRITON X-100, 1 mM EGTA, 5 mM EDTA |
| Lysate incubation | 3 temperatures/ 3 time points | 4 hr at 4° C. |
| Blocking buffers | 46 buffers | 1% polyvinyl alcohol (Mw 145,000), 3% skim milk in 1x PBS |
| Incubation of detection antibody | 4 temperatures/ 4 time points | 1 hr at RT |

TABLE 19

| Parameters | Condition tested | Optimal |
|---|---|---|
| Lysis buffers | 50 mM Tris-HCl, pH 8.0, 150 mM NaCl, 1% TRITON X-100, 2 mM EGTA, 0.01-0.1% SDS, ±5 mM EDTA 20 or 50 mM Hepes-NaOH, pH 7.5, 0-0.4M NaCl, 1 or 2% TRITON X-100, 0-0.1% SDS, 0-1.5 mM $MgCl_2$, 0-5 mM EDTA, 1-2 mM EGTA 50 mM Tris-HCl, pH 8.0, 150 mM NaCl, 0.1% SDS, 0.5% sodium deoxycholate, 1% NP-40 | 20 mM Hepes-NaOH, pH 7.5, 150 mM NaCl, 1% TRITON X-100, 5 mM EDTA, 2 mM EGTA |
| Coating buffers | 0.5% APTES 0.1M sodium acetate buffer, pH 6.0 0.1M sodium phosphate buffer, pH 7.2 0.1M sodium citrate buffer, pH 2.8 0.1M carbonate buffer, pH 9.6 | 0.1M carbonate buffer, pH 9.6 |
| Washing buffers | 1x PBS/0.05% TWEEN-20 (1x PBST), ±0.2M NaCl | 1x PBST |
| Blocking buffers | 0.2-3% Ac-BSA, 3-5% skim in 1x PBS 1% goat serum in 1x PBS 2-3% skim, 0.05-1% PVA (Mw 47,000 or 145,000) in 1x PBS 5% skim or 0.1-0.5% Ac-BSA, with 10 or 100% SUPERBLOCK ™(PBS)[a] 2-5% ECL[b] or ECL PRIME ™ Blocking agent[c] ± 0-5% skim or 0.2% Ac-BSA Western BLoT blocking buffer (protein-free)[d] | 3% skim, 1% PVA (Mw 145,000) in 1x PBS |

[a]SUPERBLOCK ™(PBS) (Thermo Fisher Scientific 37518)
[b]ECL PRIME ™ blocking agent (GE Healthcare UK limited RPN418V)
[c]ECL (GE Healthcare UK limited RPN2125V)
[d]Western BLoT blocking buffer (protein free) (Takara T7132A)

Example 17-2. Optimization of Capture Antibody

Figures 26A, 26B:
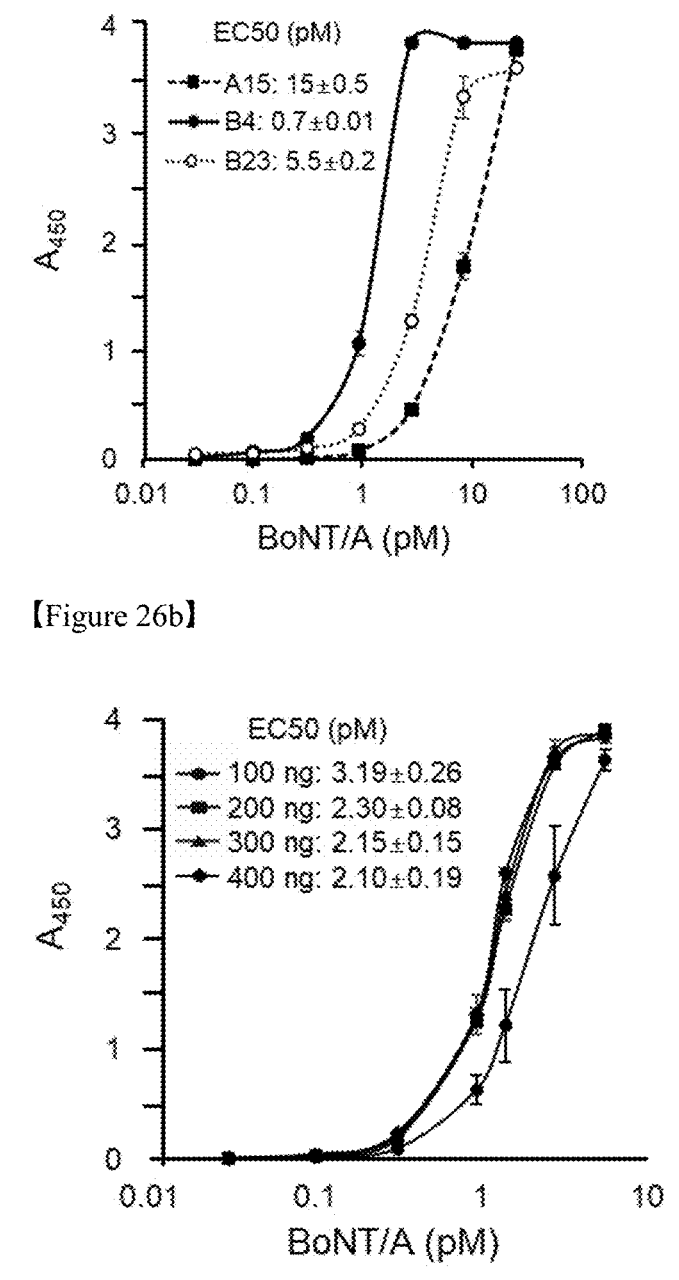

Secondly, three bi-specific antibodies, A15, B4, and B23 were compared for their function as capture antibody in sandwich ELISA. TCLs were prepared from N2-42F cells treated with varying concentrations (0-25 pM) of BoNT/A in 1× intoxication medium. TCLs were added to a microplate coated with the indicated antibody (400 ng per well). After incubation for 4 hr at 4° C., the amount of $SNAP25_{197}$ among total SNAP25 captured by the indicated antibody was detected and quantified using C16 IgG-HRP conjugates following the procedure described in Materials and Methods. One exception was that the HRP reaction was carried out for 30 min until all test groups yielded positive ELISA signal. As shown FIG. 26a, the estimated EC50 values were 15 pM, 0.7 pM, and 5.5 pM for A15, B4 and B23 IgG, respectively. This result is consistent with their $K_D$ values for $SNAP25_{FL}$ and $SNAP25_{197}$.

Optimal B4 IgG quantity was explored with TCLs prepared from N2-42F cells incubated in 2× intoxication medium containing the indicated concentration of BoNT/A following Protocol B. Sandwich ELISA was performed with a microplate coated with increasing amounts (100~400 ng per well) of B4 IgG. After incubation for 4 hr at 4° C., $SNAP25_{197}$ captured was detected and quantified using C16 IgG-HRP conjugates as described above. It should be noted that the HRP reaction was carried out for 15 min. As shown FIG. 26b, EC50 value was steadily lowered with increasing B4 IgG quantity from 100 ng to 300 ng. There was no further statistically significant improvement in EC50 with 400 ng of B4 IgG. Taken together, 300 ng of B4 IgG is used as the standard quantity of capture antibody in the optimized sandwich ELISA.

Example 17-3. Optimization of Incubation Conditions for TCL and Detection Antibody TCLs, prepared from SiMa cells treated with 8.33 or 25 pM BoNT/A in 1× intoxication medium, were incubated in a microplate under the indicated condition. Subsequently, $SNAP25_{197}$ captured was detected and quantified using C16 IgG-HRP conjugates. As shown in FIG. 27a, ELISA signal for $SNAP25_{197}$ was the highest when the microplate was incubated for 4 hr at 4° C. but was very weak after incubation at 37° C. for 1 hr. Although data not shown, similar results were obtained with TCLs of N2-42F cells, and ELISA signal was not significantly changed by longer than 4 hr-incubation. Thus, in the optimized sandwich ELISA, TCL is incubated for 4 hr at 4° C.

The optimal incubation condition for detection antibody was explored by direct ELISA. In brief, the microplates were coated with varying amounts (from 10 pg to 1 ng) of recombinant GST-$SNAP25_{197}$ that represent the endogenous SNAP25 cleavage from 0.05% to 50% in the standard CBPA. After adding C16 IgG-HRP conjugates (200 ng per well), the microplates were incubated under the indicated condition. Of conditions test, incubation of Cg16 IgG-HRP conjugates at RT for 1 hr yielded the highest ELISA signal for all ranges of GST-$SNAP25_{197}$ examined but other conditions also generated acceptable levels of ELISA signal. When considering the subsequent HRP reaction that is carried out at RT, however, in the optimized sandwich ELISA, C16-HRP conjugates are incubated for 1 hr at RT.

Example 17-4. Optimization of Detection Method for C16 IgG-HRP Conjugates

HRP activity was generally measured using a conventional TMB substrate (1-STEP™ Ultra TMB-ELISA). One drawback in using TMB substrate is EC50 value tends to be influenced by HRP reaction time (FIGS. 26 & 29). The longer HRP reaction yields the lower EC50. As an alternative detection method, a fluorimetric measurement was comparatively evaluated in sandwich ELISA. Except for the HRP reaction substrate provided, the colorimetric and fluorimetric measurement were carried out in parallel following essentially the same way throughout sandwich ELISA. Fluorimetric and colorimetric measurements generated 0.66 and 0.78 pM of EC50 (FIG. 28), and both EC50 values were equally influence by HRP reaction time (data not shown). In conclusion, despite the fluorimetric measurement of HRP reaction necessitates a black microplate and a microplate reader built-in with a fluorimeter, both measurements are accurate and sensitive enough to detect the activity of C16 IgG-HRP conjugates in the optimized ELISA.

Example 18: Validation and Practical Application of CBPA

Example 18-1. Optimized Timeline of CBPA

Taken all optimized conditions and reagents together, the finally established optimal CBPA can be performed with only three working days, as depicted in FIG. 29. In brief, cells are plated on day 1, and on the next day 2, medium is replaced with 2× intoxication medium containing BoNT/A (0.1-10 U/ml or less than 4 pM). On day 6, cells are treated with lysis buffer, and with the resulting TCL, sandwich ELISA is carried out and BoNT/A bio-potency is determined. Avoiding the bench-work on weekend, it is possible to perform the optimized CBPA three times a week, with only 1-2 working hours during the first two days and one full-working day. Thus, the optimized CBPA is suitable for measuring the bio-potency of multiple lots of pharmaceutical or cosmetic BoNT/A products a week. The use of two monoclonal antibodies for sandwich ELISA, excluding rabbit polyclonal antibodies, makes the CBPA highly reliable since their acquisition and subsequent quality control are superior to those of polyclonal antibodies.

Example 18-2. Accuracy and Linearity of CBPA

Following the standard Protocol B, a total of 18 CBPA were performed by three operators.

Figures 30A, 30B:
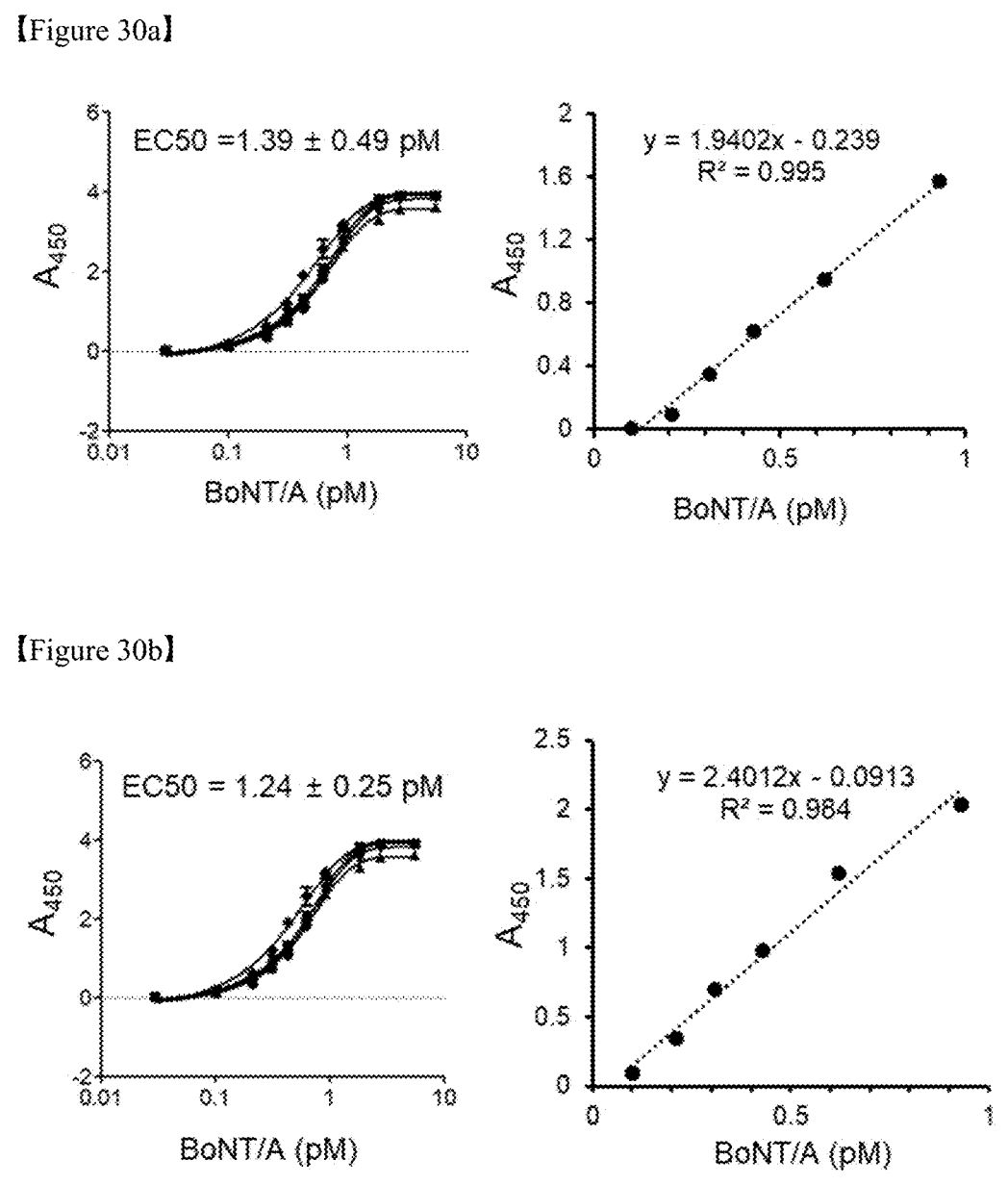
Figures 30C, 31A:
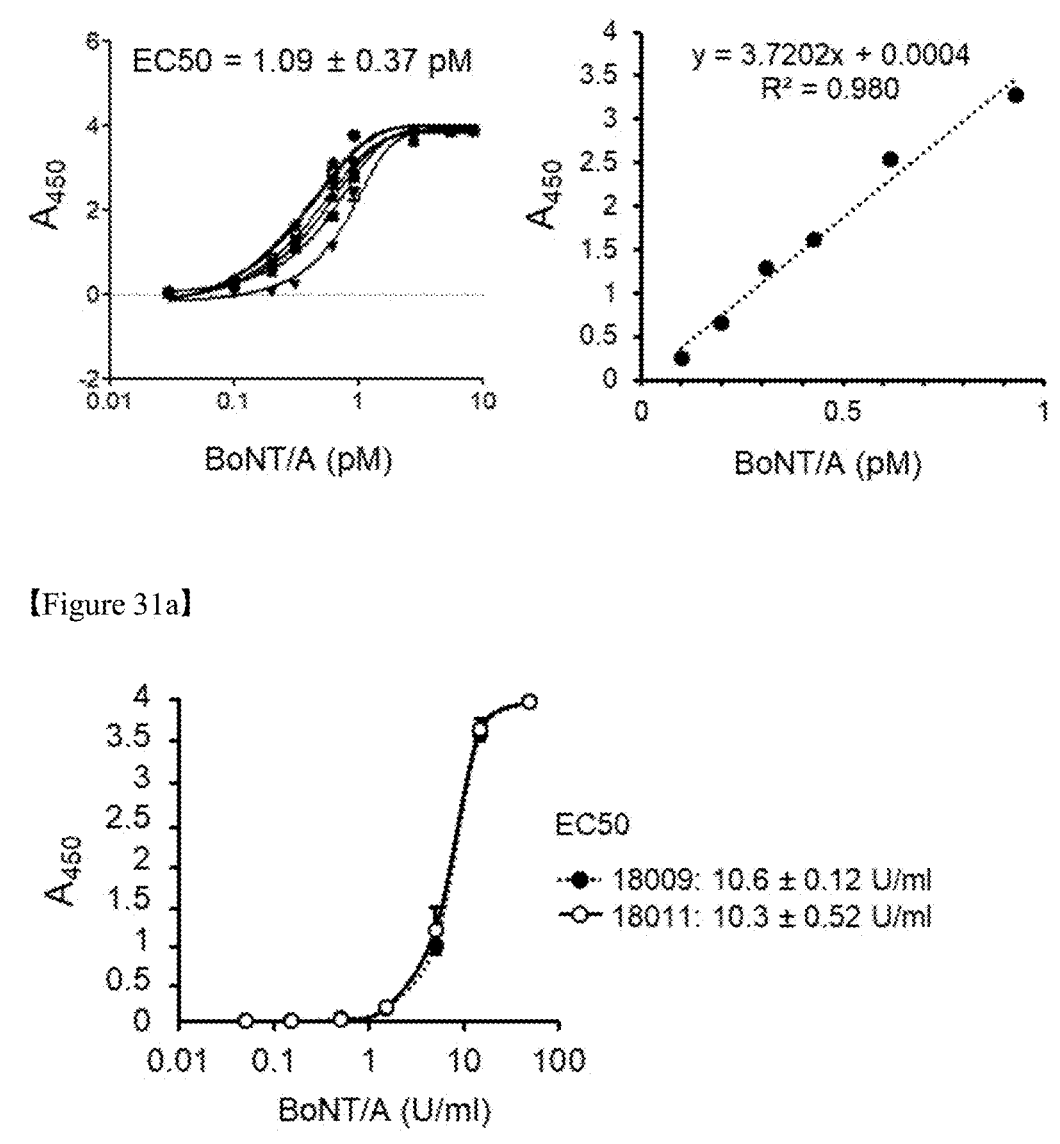

A total of 18 CBPA were performed by three operators following Protocol B. N2-42F cells were treated with varying concentrations (0, 0.03, 0.1, 0.2, 0.31, 0.62, 0.93, 2.78, 5.55, 8.33 pM) of BoNT/A in 2× intoxication medium (FIG. 30*a*) or 2× intoxication medium containing 3×GT1b (FIG. 30*b* & FIG. 30*c*). HRP reaction was carried out for 5 min (FIG. 30*a* & FIG. 30*b*) or 9 min (FIG. 30*c*), and EC50 was determined using Gen5 software. Linear regression analysis was performed with A450 values obtained with N2-42F cells treated with 0.1 to 0.93 pM BoNT/A, and the results are shown in FIG. 30.

The first series of CBPA yielded 1.39 pM of EC50 with 1.5 fM (3.4 mU relative potency/ml) of detection limit (DL) and 4.6 fM of quantitation limit (QL) (Clin Biochem Rev. 2008 August; 29 Suppl 1:S49-52.; Anal Sci. 2007 February; 23(2):215-8). Since the 1.39 pM BoNT/A is equivalent to ~0.3 U relative potency per assay, the first CBPA is sensitive enough to measure the bio-potency of BoNT/A in place of mouse LD50 assay. A slightly lower EC50 value, 1.24 pM, was obtained by a prolonged HRP reaction employed in the second series of CBPA (FIG. 30*b*). The impact of HRP reaction time on EC50 was previously noticed (FIG. 29). The third series of CBPA, performed using the intoxication medium with 3×GT1b, yielded the lowest 1.09 pM of EC50, consistent with the results in FIG. 27.

This result indicates that the quantitation power and detection limit of CBPA, developed in the present research, can be adjusted by modulating HRP reaction time or changing GT1b concentration in the intoxication medium. Linear regression analysis of ELISA signals for N2-42F cells treated with 0.03~0.93 pM BoNT/A revealed an excellent linear correlation between the relative potency of BoNT/A and ELISA signal in all three series of CBPA (FIG. 30). This result indicates that CBPA is not only highly sensitive but also very accurate in measuring the relative potency of BoNT/A between 6.8 mU and 0.2 U per assay.

Example 18-3. Measurement of the Bio-Potency in BOTULAX® Samples

Figures 31B, 31C:
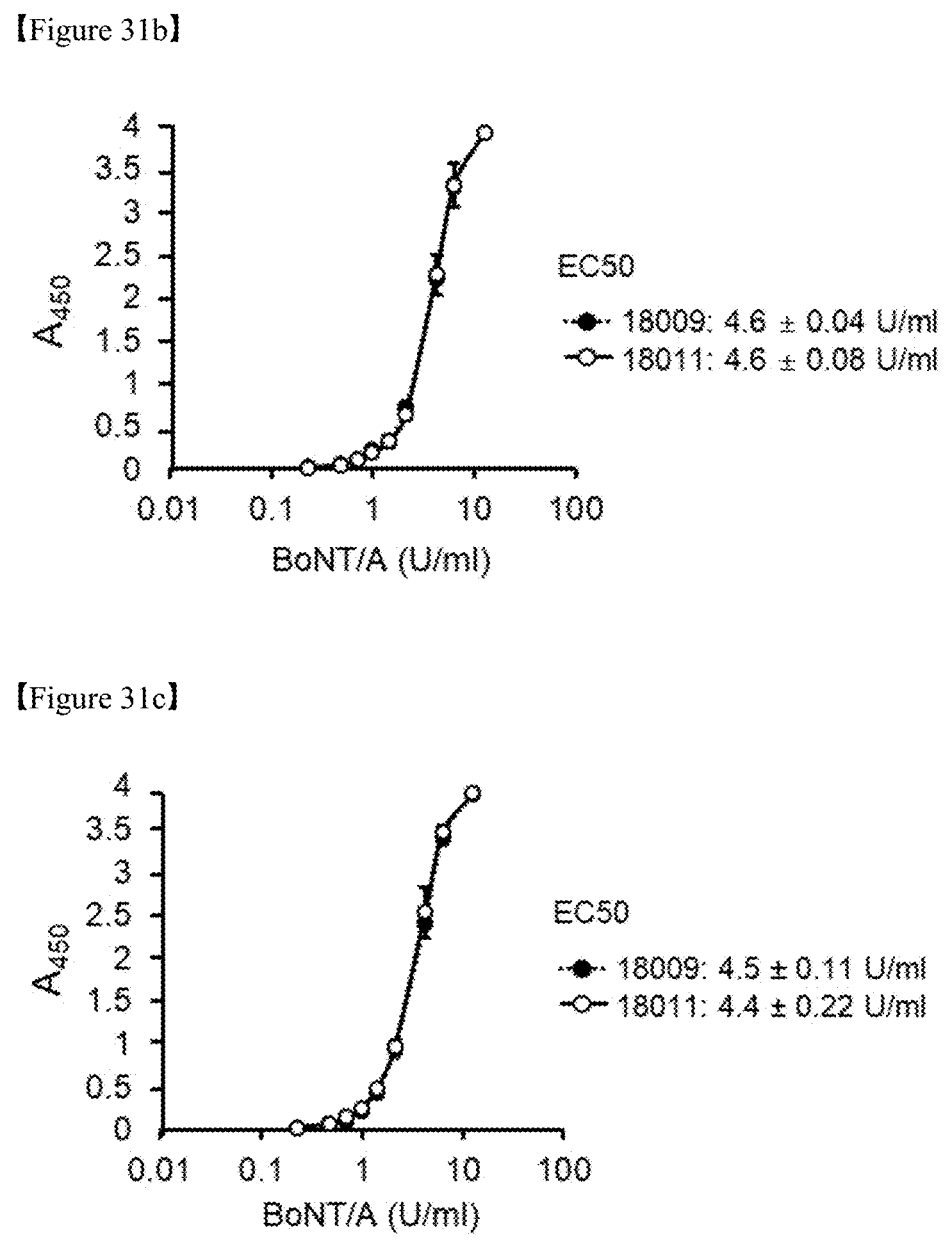

BoNT/A potency in BOTULAX® was determined by mouse LD50. To measure this bio-potency using CBPA, two different lots (HUB 18009 and HUB 18011) of BOTULAX® (200 U per vial) were dissolved in either intoxication medium (matrix a), deionized $H_2O$ (matrix b), or 5 mM arginine, pH 6.0 (matrix c). After 10 min incubation at RT, BOTULAX® dissolved in medium was serially diluted to 0.015, 0.05, 0.15, 0.5, 1.5, 5, 15, and 50 U/ml, but the others were to 0.23, 0.48, 0.70, 0.98, 1.41, 2.11, 4.20, 6.32, and 12.6 U/ml in the optimized intoxication medium. Three different sets of CBPA were carried out using these samples following the standard Protocol B. The EC50 values was determined. As shown in FIG. 31, EC50 values of two lots were 10.6±0.12 and 10.3±0.52 U/ml with matrix a, 4.6±0.04 and 4.6±0.08 U/ml with matrix b, and 4.5±0.11 and 4.4±0.22 U/ml with matrix c. This result indicates that CBPA is sensitive and accurate enough to measure the bio-potency of BOTULAX® and its sensitivity (0.4-0.5 U per well) is equivalent or superior to the mouse bioassay.

Although the present disclosure has been described in detail with reference to the specific features, it will be apparent to those skilled in the art that this description is only of a preferred embodiment thereof, and does not limit the scope of the present invention. Thus, the substantial scope of the present invention will be defined by the appended claims and equivalents thereof.

[Accession Number]
Depository authority: Korea Research Institute of Bioscience and Biotechnology;
Accession number: KCTC13712BP;
Deposit date: Nov. 13, 2018.

N2-42F cell line (accession number: KCTC 13712BP) was deposited with the Korean Collection for Type Cultures (KCTC) at Korea Research Institute of Bioscience and Biotechnology 181, Ipsin-gil, Jeongeup-si, Jeollabuk-do, 56212, Republic of Korea according to the provisions of the Budapest Treaty on the International Recognition of the Deposit of Microorganisms for the Purposes of Patent Procedure, on Nov. 13, 2018. The subject cell line has been deposited under conditions that assure that access to the cell line will be available during the pendency of this patent application to one determined by the Commissioner of Patents and Trademarks to be entitled thereto under 37 CFR 1.14 and 35 U.S.C. 122. The deposit will be 10 available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject deposits will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least thirty (30) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

The invention claimed is:

1. A N2-42F cell line (accession number: KCTC 13712BP).

2. A method for culturing the N2-42F cell line of claim 1, comprising culturing cells of the N2-42F cell line in a culture medium, wherein the culture medium contains ganglioside GT1b trisodium salt (GT1b).

* * * * *